(12) United States Patent
Finley et al.

(10) Patent No.: US 7,705,025 B2
(45) Date of Patent: Apr. 27, 2010

(54) HISTAMINE H3 RECEPTOR AGENTS, PREPARATION AND THERAPEUTIC USES

(75) Inventors: Don Richard Finley, Greenwood, IN (US); Terry Patrick Finn, Geneva (CH); Philip Arthur Hipskind, New Palestine, IN (US); William Joseph Hornback, Fishers, IN (US); Cynthia Darshini Jesudason, Indianapolis, IN (US); Takako Takakuwa, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/574,044

(22) PCT Filed: Aug. 15, 2005

(86) PCT No.: PCT/US2005/029032

§ 371 (c)(1),
(2), (4) Date: Feb. 21, 2007

(87) PCT Pub. No.: WO2006/023462

PCT Pub. Date: Mar. 2, 2006

(65) Prior Publication Data

US 2009/0048225 A1    Feb. 19, 2009

Related U.S. Application Data

(60) Provisional application No. 60/603,628, filed on Aug. 23, 2004.

(51) Int. Cl.
*A61K 31/427*    (2006.01)
*C07D 277/20*    (2006.01)

(52) U.S. Cl. ............... 514/365; 548/200; 548/202; 548/204

(58) Field of Classification Search ........ 548/200, 548/202, 204; 514/365
See application file for complete search history.

(56) References Cited

U.S. PATENT DOCUMENTS

2007/0208024 A1 * 9/2007 Beavers et al. ............ 514/247

FOREIGN PATENT DOCUMENTS

| WO | WO 02/076925 | 10/2002 |
|----|--------------|---------|
| WO | WO 03/064411 | 8/2003 |
| WO | WO 2004/076412 | 9/2004 |
| WO | WO 2005/097740 | 10/2005 |

* cited by examiner

*Primary Examiner*—Kamal A Saeed
*Assistant Examiner*—Samantha L Shterengarts
(74) *Attorney, Agent, or Firm*—Dan L. Wood

(57) ABSTRACT

The present invention provides a novel compound of Formula (I) or a pharmaceutically acceptable salt thereof, having histamine-H3 receptor antagonist or inverse agonist activity, as well as methods for preparing such compounds. In another, embodiment, the invention discloses pharmaceutical compositions comprising compounds of Formula (I) as well as methods of using them to treat obesity, cognitive deficiencies, narcolepsy, and other histamine H3 receptor-related diseases.

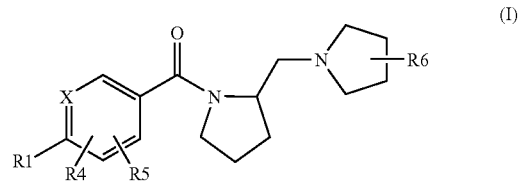

(I)

18 Claims, No Drawings

HISTAMINE H3 RECEPTOR AGENTS, PREPARATION AND THERAPEUTIC USES

This patent application claims the benefit of U.S. Provisional Patent Application No. 60/603,628 filed Aug. 23, 2004.

The present invention relates to novel heteroaromatic aryl compounds, and to the use of these compounds as pharmaceutical compositions, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, H3R inverse agonists or antagonists induce a prolonged wakefulness, improved cognitive function, reduction in food intake, and normalization of vestibular reflexes. Accordingly, the histamine H3 receptor is an important target for new therapeutics in Alzheimer's disease, mood and attention adjustments, cognitive deficiencies, obesity, dizziness, schizophrenia, epilepsy, sleeping disorders, narcolepsy, and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)]. Alternative names for this receptor are PORT3 or H4R. Although relatively selective ligands have been developed for H1R, H2R and H3R, few specific ligands have been developed that can distinguish H3R from H4R. H4R is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently, other imidazole and non-imidazole ligands of the histamine H3 receptor have been described. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of heteroaromatic aryl compounds have a high affinity, selective, and potent activity at the histamine H3 receptor. The subject invention is distinct in the particular structures and their activities.

SUMMARY OF THE INVENTION

The present invention provides a compound structurally represented by Formula I:

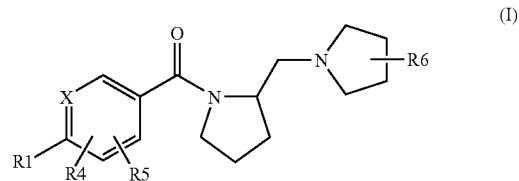

or a pharmaceutically acceptable salt thereof wherein:

X independently represents carbon (substituted with hydrogen or the optional substituents indicated herein), or nitrogen;

R1 is independently -HET (optionally substituted on carbon, independently, one to three times with R2, and optionally once substituted on nitrogen with R3), or -Benzofused heterocycle (optionally substituted on carbon, independently, one to three times with R2, and optionally once substituted on nitrogen with R3);

R2 is independently at each occurrence
—H, -halogen, —($C_1$-$C_7$)alkyl (optionally substituted with one to three halogens), —CN, —C(O)R7, —C(O)OR7, —C(O)($C_3$-$C_5$)cycloalkyl (optionally substituted with one to three halogens), —C(O)NR7R8, —OR7, —$NO_2$, —NR7R8, —$NR9SO_2R7$, —NR9C(O)R7, —$NR9CO_2R7$, —NR9C(O)NR7R8, —SR7, —$SO_2R7$, —$SO_2NR7R8$, —S(O)R7, -phenyl-R9, —C(H)=NO—R7, -pyridinyl, -HET-R9, or —($C_1$-$C_7$)alkyl-NHC(O)R7 (provided that not more than one occurrence of R2 is -HET-R9 or -phenyl-R9);

R3 is independently at each occurrence
—H, —($C_1$-$C_7$)alkyl (optionally substituted with one to three halogens), —$SO_2R7$, —C(O)R7, —C(O)NR7R8, or —C(O)OR7;

R4 and R5 are independently
—H, —OH, -halogen, —($C_1$-$C_3$)alkyl (optionally substituted with one to three halogens), or —OR9, provided that when X is nitrogen, then R4 and R5 are not attached to X;

R6 is independently
H, -halogen, —($C_1$-$C_3$)alkyl (optionally substituted with one to three halogens), —$NH_2$, —NR7R8, —OH, or —OR7;

R7 and R8 are independently
—H, -phenyl, —($C_1$-$C_7$)alkyl (optionally substituted with one to three halogens); or R7 and R8 combine with the atom to which they are attached to form a 4 to 7 membered ring;

R9 is
—H, -halogen, —($C_1$-$C_3$)alkyl (optionally substituted with one to three halogens), or —OR7.

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R. The term "H3R" means the histamine H3 receptor that inhibits the release of a number of monoamines, including histamine. The term "H1R" means the histamine H1 receptor subtype. The term "H2R" means the histamine H2 receptor subtype.

The term "H3R antagonists" is defined as a compound with the ability to block forskolin-stimulated cAMP production in response to agonist R-(−)α methylhistamine. The term "H3R inverse agonist" is defined as a compound with the ability to inhibit the constitutive activity of H3R. "Selective H3R antagonists or inverse agonists" means a compound of the present invention having a greater affinity for H3 histamine receptor than for GPRv53 histamine receptor.

In the formulae of the present document, the general chemical terms have their usual meanings unless otherwise indicated. For example;

"($C_1$-$C_3$) Alkyl" are one to three carbon atoms such as methyl, ethyl, propyl, and the like, optionally substituted with one to three halogens, and "($C_1$-$C_4$)alkyl" are one to four carbon atoms such as methyl, ethyl, propyl, butyl and the like, optionally substituted with one to three halogens, and "($C_1$-$C_7$)Alkyl" are one to seven carbon atoms such as methyl, ethyl, propyl, butyl, pentyl, hexyl, heptyl, and the like, optionally substituted with one to three halogens. As defined herein "alkyl" includes branched or isomeric forms.

"($C_3$-$C_5$)Cycloalkyl" means a ring with three to five carbon atoms such as cyclopropyl, cyclobutyl, and cyclopentyl.

The term "HET" represents a stable aromatic heterocyclic ring, containing five atoms of which one to four are heteroatoms, that are the same, or different, selected from N, O, and S. The heterocyclic ring of "HET" may be attached at any point which affords a stable structure. Representative "HET" rings include furan, imidazole, isothiazole, isoxazole, oxadiazole, oxazole, pyrazole, pyrrole, tetrazole, thiadiazole, thiazole, thiophene, and triazole, and the like. Further specific examples of five membered heterocycles are described below, and further described in the Preparations and Examples sections.

The term "Benzofused heterocycle" includes benzofused heterocyclic rings optionally substituted one to three times, independently at each occurrence, by R2 as defined herein, or R3 as defined herein, and representative benzofused heterocyclic rings include benzoxazole, benzimidazole, benzofuran, benzothiophene, benzothiazole, azaindole, indole, and phthalimide, and the like. Further specific examples of benzofused heterocycles are described below, and further described in the Preparations and Examples sections.

"Halogen" or "halo" means fluoro, chloro, bromo, and iodo.

The term "optionally substituted" as used herein means that the groups in question are either unsubstituted or substituted with one or more of the substituents specified. When the groups in question are substituted with more than one substituent, the substituents may be the same or different. Furthermore, when using the terms "independently", "independently are", and "independently selected from" it should be understood that the groups in question may be the same or different.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating", and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s), Formula I, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

In one embodiment, the present invention provides compounds of Formula I as described in detail above. While all of the compounds of the present invention are useful, certain of the compounds are particularly interesting and are preferred. The following listing sets out several groups of preferred compounds. It will be understood that each of the listings may be combined with other listings to create additional groups of preferred embodiments.

In another embodiment the invention provides a compound structurally represented by Formula I wherein X represents carbon (substituted with hydrogen or the optional substituents indicated herein).

In another embodiment the invention provides a compound structurally represented by Formula I wherein X represents nitrogen.

In another embodiment the invention provides a compound structurally represented by Formula I, or a pharmaceutically acceptable salt thereof, wherein: R1 is independently

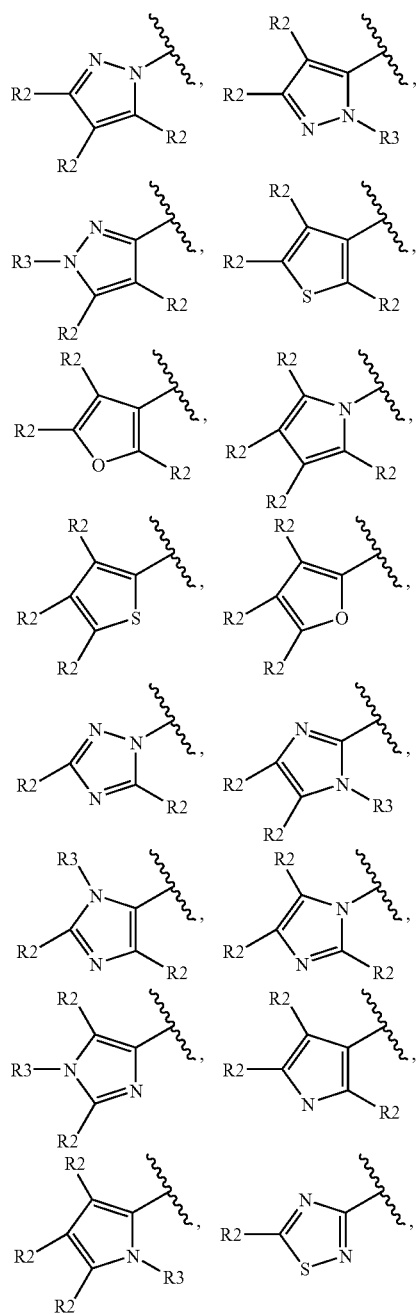

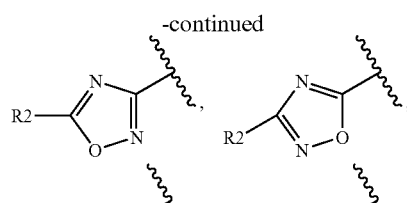

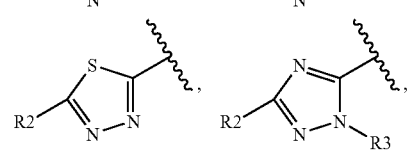

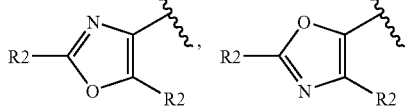

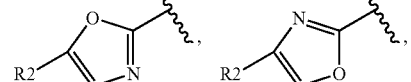

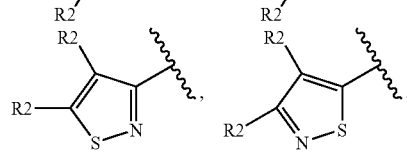

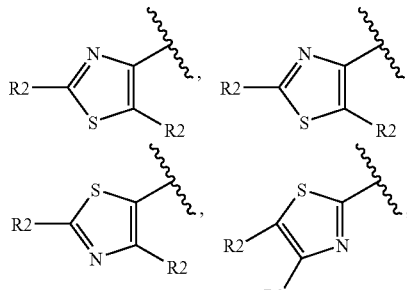

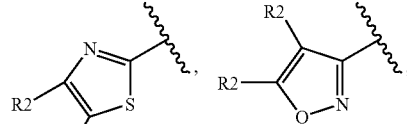

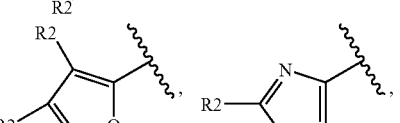

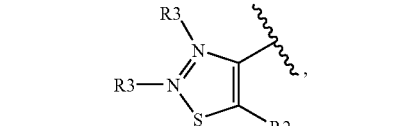

wherein the bond directed to the zig-zag lines indicates the point of attachment to the position indicated by R1 in Formula I.

In another embodiment the invention provides a compound structurally represented by Formula I, or a pharmaceutically acceptable salt thereof, wherein: R1 is independently

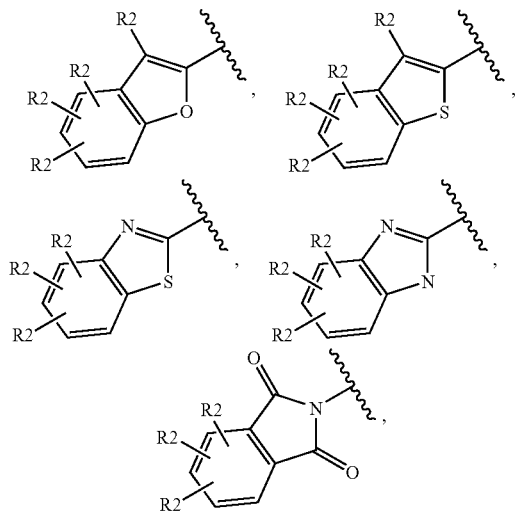

wherein the bond directed to the zig-zag lines indicates the point of attachment to the position indicated by R1 in Formula I.

In another embodiment the invention provides a compound structurally represented by Formula I, or a pharmaceutically acceptable salt thereof, wherein R1 is selected from the group consisting of

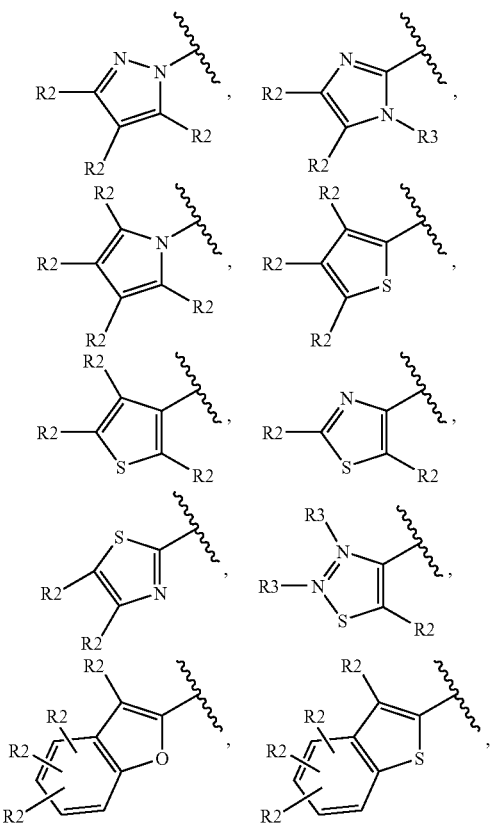

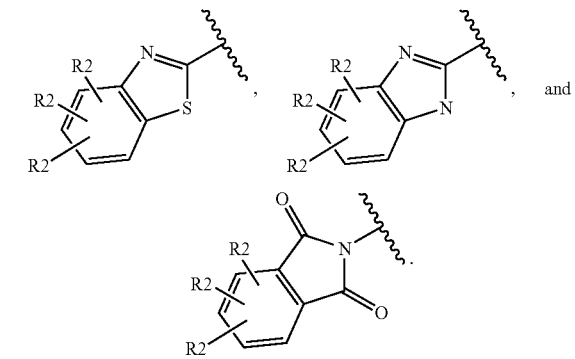

In another embodiment the invention provides a compound structurally represented by Formula I, or a pharmaceutically acceptable salt thereof, wherein R1 is selected from the group consisting of

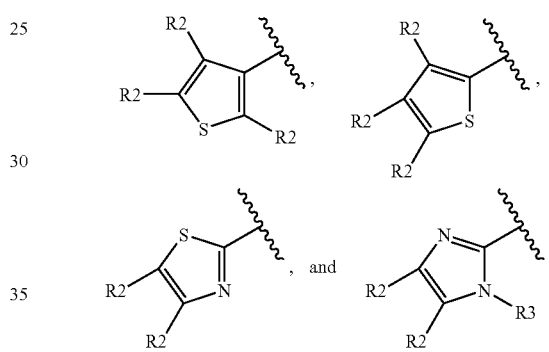

wherein the bond directed to the zig-zag lines indicates the point of attachment to the position indicated by R1 in Formula I.

In another embodiment the invention provides a compound structurally represented by Formula I, or a pharmaceutically acceptable salt thereof, wherein R6 is —($C_1$-$C_3$)alkyl (optionally substituted with one to three halogens);

In another embodiment the invention provides a compound structurally represented by Formula I, or a pharmaceutically acceptable salt thereof, wherein R6 is —$CH_3$.

In another embodiment the invention provides a compound structurally represented by Formula I, or a pharmaceutically acceptable salt thereof, wherein: X independently represents carbon (substituted with hydrogen or the optional substituents indicated herein), or nitrogen;

R1 is independently

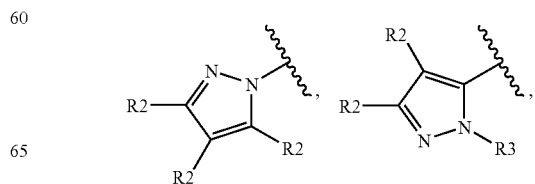

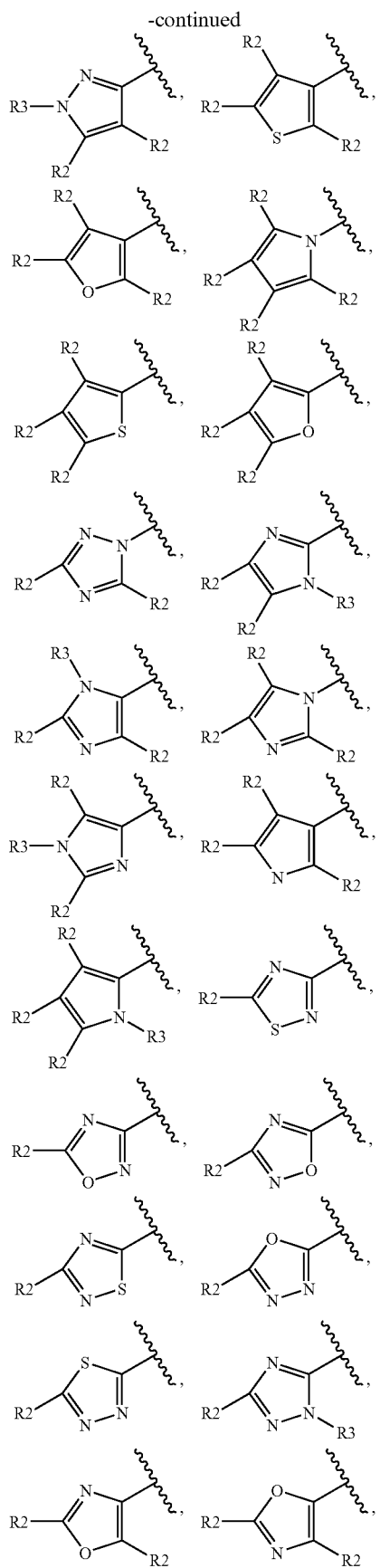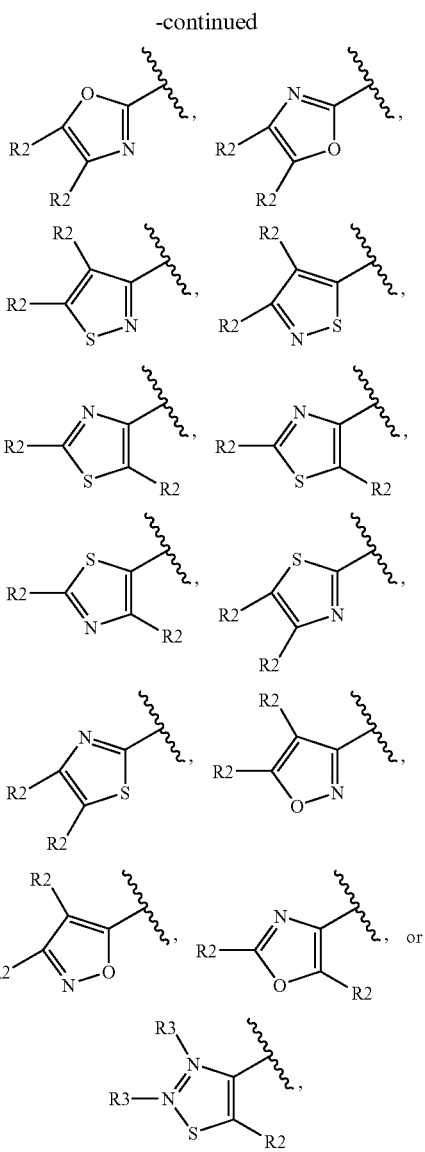
wherein the bond directed to the zig-zag lines indicates the point of attachment to the position indicated by R1 in Formula I, or
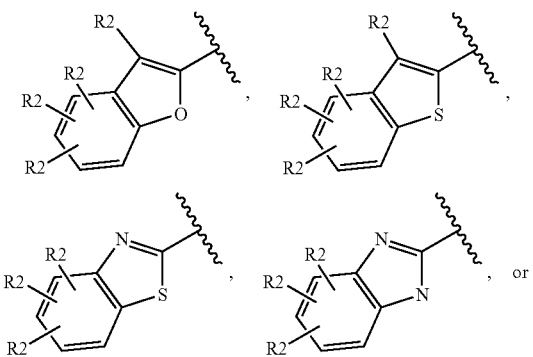

-continued

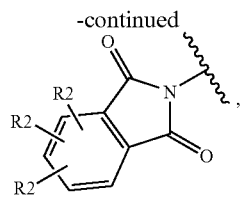

wherein the bond directed to the zig-zag lines indicates the point of attachment to the position indicated by R1 in Formula I;

R2 is independently at each occurrence
—H, -halogen, —($C_1$-$C_7$)alkyl (optionally substituted with one to three halogens), —CN, —C(O)R7, —C(O)OR7, —C(O)($C_3$-$C_5$)cycloalkyl, —C(O)NR7R8, —OR7, —$NO_2$, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -phenyl-R9, —C(H)=NO—R7, -pyridinyl, -HET-R9, or —($C_1$-$C_7$)alkyl-NHC(O)R7 (provided that not more than one occurrence of R2 is -HET-R9, -phenyl-R9, or -pyridinyl);

R3 is independently at each occurrence
—H, —($C_1$-$C_3$)alkyl (optionally substituted with one to three halogens), —$SO_2$R7, —C(O)R7, —C(O)NR7R8, or —C(O)OR7;

R4 and R5 are independently
—H, —OH, -halogen, —$CH_3$, —$CF_2$H, —$CF_3$, or —$OCH_3$, provided that when X is nitrogen, then R4 and R5 are not attached to X;

R6 is independently
—H, -halogen, or —($C_1$-$C_3$)alkyl (optionally substituted with one to three halogens);

R7 and R8 are independently
—H, —($C_1$-$C_4$)alkyl (optionally substituted with one to three halogens); or
R7 and R8 combine with the atom to which they are attached to form a 4 to 6 membered ring;

R9 is
—H, -halogen, —($C_1$-$C_3$)alkyl (optionally substituted with one to three halogens), or —OR7.

In another embodiment the invention provides a compound structurally represented by Formula I, or a pharmaceutically acceptable salt thereof, wherein; X independently represents carbon (substituted with hydrogen or the optional substituents indicated herein), or nitrogen; R1 is

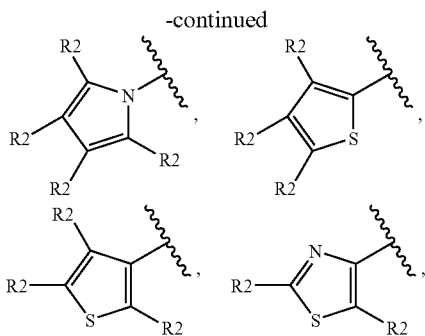

-continued

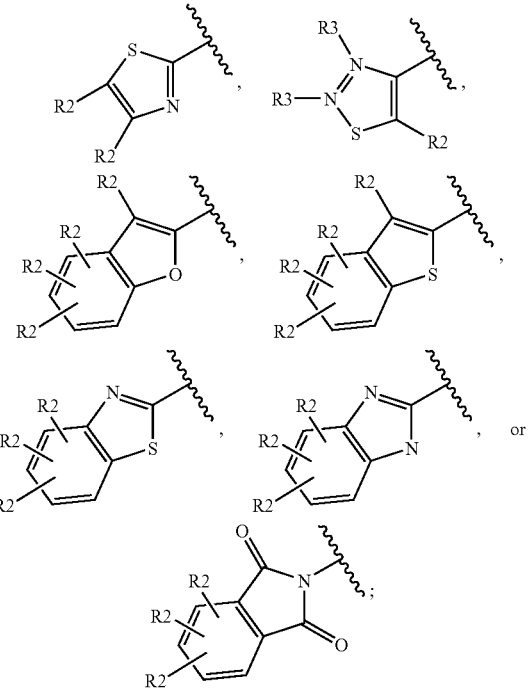

R2 is —H, -halogen, —($C_1$-$C_7$)alkyl, —CN, —C(O)R7, —C(O)OR7, —C(O)NR7R8, —OR7, SR7, —$SO_2$R7, —$SO_2$NR7R8, —C(H)=NO—R7, -pyridinyl, -HET-R9, or —($C_1$-$C_7$)alkyl-NHC(O)R7; R3 is -hydrogen or —($C_1$-$C_7$)alkyl; R4 is -hydrogen and R5 is -hydrogen or -halogen; R6 is hydrogen or —($C_1$-$C_3$)alkyl; R7 and R8 are independently hydrogen, -phenyl, —($C_1$-$C_7$)alkyl, or R7 and R8 combine with the nitrogen atom to which they are attached to form a 4 to 6 membered ring; and R9 is -hydrogen, -halogen, —($C_1$-$C_3$)alkyl, or —OR7.

In another embodiment the invention provides a compound structurally represented by Formula I, or a pharmaceutically acceptable salt thereof, wherein: R1 is selected from the group consisting of

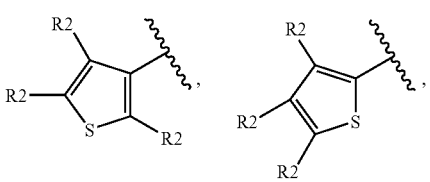

-continued

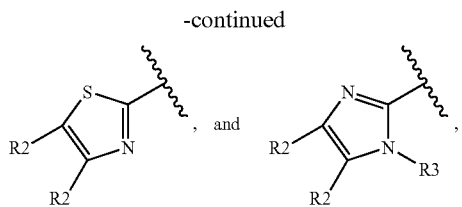, and wherein the bond directed to the zig-zag lines indicates the point of attachment to the position indicated by R1 in Formula I; R2 is -hydrogen, —CN, —C(O)R7, —C(O)NR7R8, —SO$_2$R7, —SO$_2$NR7R8, or —C(H)=NO—R7; R3 is -hydrogen or —(C$_1$-C$_7$)alkyl; R4 is hydrogen and R5 is hydrogen or halogen; R6 is —H or —(C$_1$-C$_3$)alkyl; R7 and R8 are independently -hydrogen, —(C$_1$-C$_7$)alkyl, or R7 and R8 combine with the nitrogen atom to which they are attached to form a 4 to 6 membered ring;

In another embodiment the invention provides a compound structurally represented by Formula I, or a pharmaceutically acceptable salt thereof, wherein: X is carbon substituted with hydrogen; R1 is selected from the group consisting of

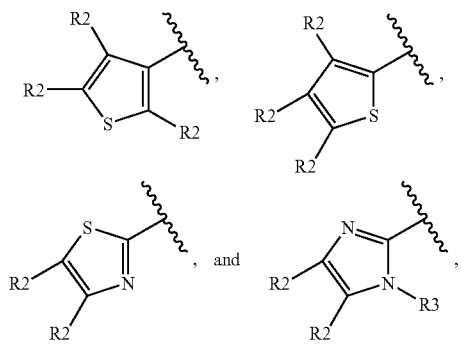, and wherein the bond directed to the zig-zag lines indicates the point of attachment to the position indicated by R1 in Formula I; R2 is -hydrogen, —CN, —C(O)R7, —C(O)NR7R8, —SO$_2$R7, —SO$_2$NR7R8, or —C(H)=NO—R7; R3 is -hydrogen, or —(C$_1$-C$_7$) alkyl; R4 is hydrogen and R5 is hydrogen or halogen; R6 is —H, or —(C$_1$-C$_3$)alkyl; R7 and R8 are -hydrogen, —(C$_1$-C$_7$)alkyl, or R7 and R8 combine with the nitrogen atom to which they are attached to form a 4 to 6 membered ring.

In another embodiment the invention provides a compound structurally represented by Formula I, or a pharmaceutically acceptable salt thereof, wherein: X independently represents carbon (substituted with hydrogen or the optional substituents indicated herein), or nitrogen; R1 is

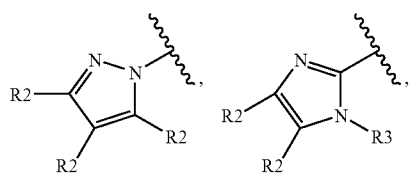

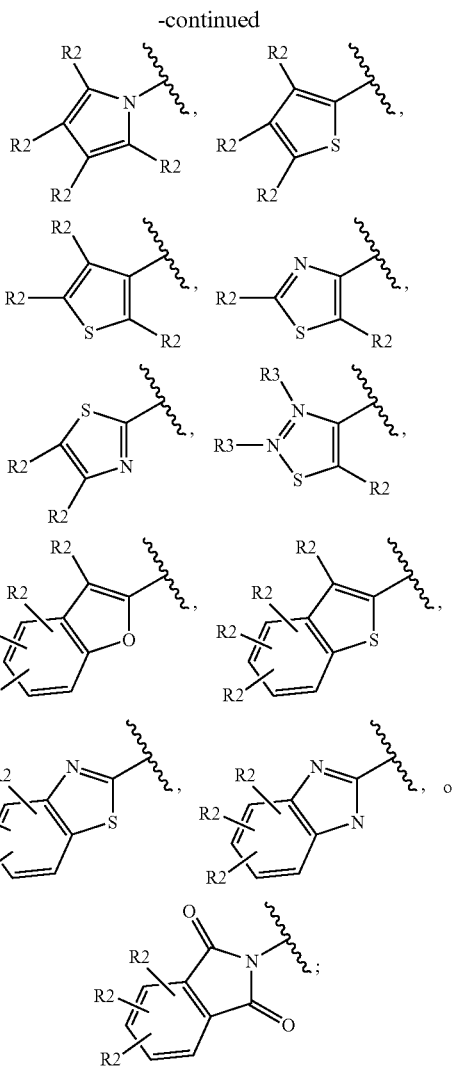

R2 is —H, —Br, —Cl, —CH$_3$, —CN, —C(O)CH$_3$, —C(O)CH(CH$_3$)$_2$, —C(O)OCH$_2$CH$_3$, —C(O)NH$_2$, —C(O)N(CH$_3$)$_2$, —C(O)-pyrrolidinyl, —C(O)N-azetidinyl, —C(O)N-piperidinyl, —OCH$_3$, —SCH$_3$, —SO$_2$CH$_3$, —SO$_2$CH$_2$CH$_3$, —SO$_2$NH$_2$, -oxazolyl, -phenyl, -3-ethoxyphenyl, -4-chlorophenyl, -4-pyridinyl, -3-pyridinyl, —N-isopropylacetamide, —N-isopropylbenzamide, or -2-carbaldehyde-O-methyl-oxime; R3 is -hydrogen or —CH$_3$; R4 is -hydrogen and R5 is -hydrogen or —F; and R6 is hydrogen or —CH$_3$.

The following listing sets out several groups of preferred embodiments. It will be understood that each of the listings may be combined with other listings to create additional groups of preferred embodiments. Thus, in additional preferred embodiments the invention provides a compound structurally represented by the formulae of the above embodiments, or a pharmaceutically acceptable salt thereof, wherein:

1. wherein X is carbon (substituted with hydrogen or the optional substituents indicted herein).
2. wherein X is nitrogen.

3. wherein R1 is selected from the group consisting of

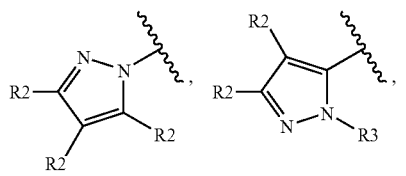
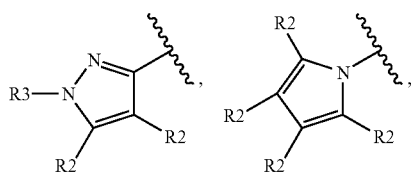
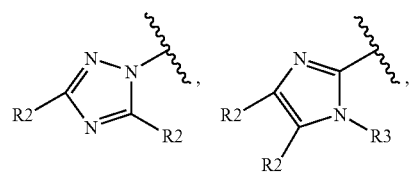
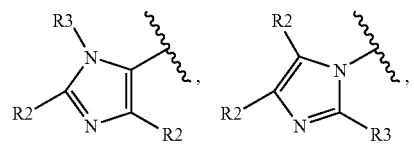
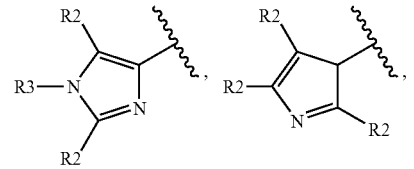
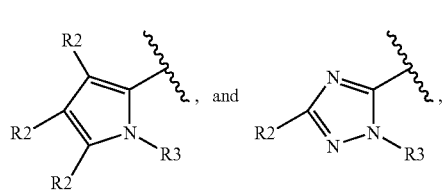
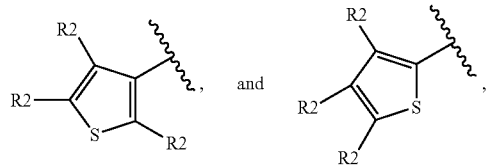

wherein the bond directed to the zig-zag lines indicates the point of attachment to the position indicated by R1 in Formula I.

4. wherein R1 is selected from the group consisting of

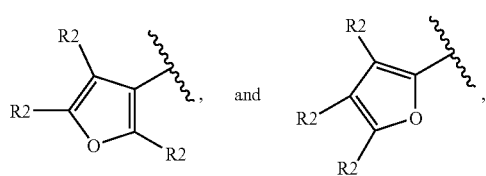

wherein the bond directed to the zig-zag lines indicates the point of attachment to the position indicated by R1 in Formula I.

5. wherein R1 is selected from the group consisting of

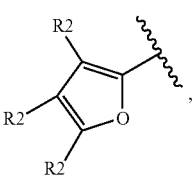

wherein the bond directed to the zig-zag lines indicates the point of attachment to the position indicated by R1 in Formula I.

6. wherein R1 is selected from the group consisting of

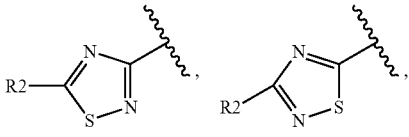
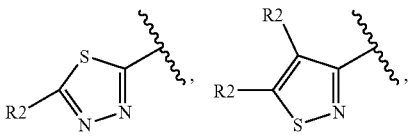
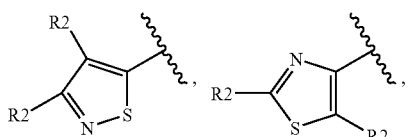
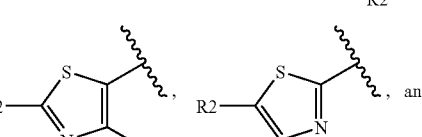
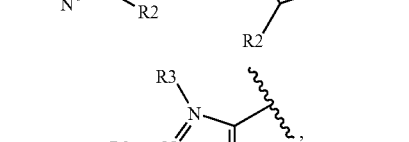
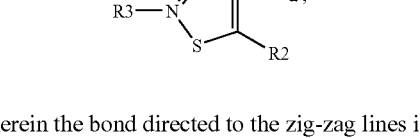

wherein the bond directed to the zig-zag lines indicates the point of attachment to the position indicated by R1 in Formula I.

7. wherein R1 is selected from the group consisting of

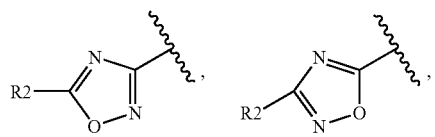
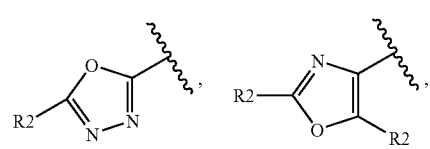
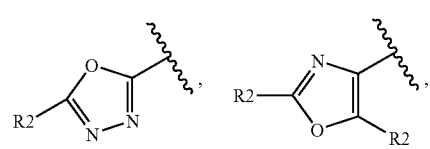

-continued

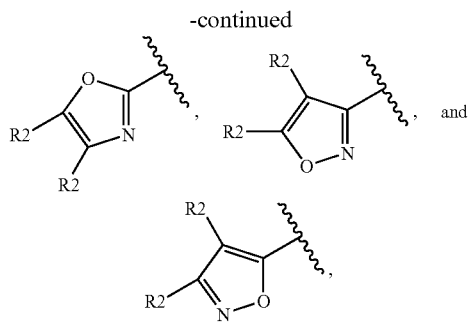

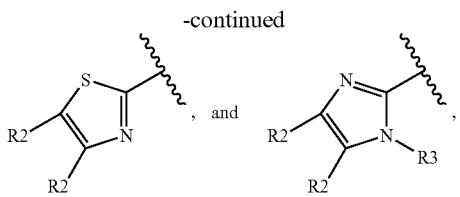

wherein the bond directed to the zig-zag lines indicates the point of attachment to the position indicated by R1 in Formula I.

8. wherein R2 is selected from the group consisting of —H, -halogen, —($C_1$-$C_7$)alkyl, —CN, —C(O)R7, —C(O)OR7, —C(O)NR7R8, —OR7, —SR7, —$SO_2$R7, —$SO_2$NR7R8, —C(H)=NO—R7, -pyridinyl, -HET-R9, and —($C_1$-$C_7$)alkyl-NHC(O)R7.

9. wherein R2 is selected from the group consisting of —H, —Br, —Cl, —$CH_3$, —CN, —C(O)$CH_3$, —C(O)CH($CH_3$)$_2$, —C(O)O$CH_2CH_3$, —C(O)$NH_2$, —C(O)N($CH_3$)$_2$, —C(O)-pyrrolidinyl, —C(O)N-azetidinyl, —C(O)N-piperidinyl, —O$CH_3$, —S$CH_3$, —$SO_2CH_3$, —$SO_2CH_2CH_3$, —$SO_2NH_2$, -oxazolyl, -phenyl, -3-ethoxyphenyl, -4-chlorophenyl, -4-pyridinyl, -3-pyridinyl, —N-isopropylacetamide, —N-isopropylbenzamide, and -2-carbaldehyde-O-methyl-oxime.

10. wherein R3 is -hydrogen or —($C_1$-$C_7$)alkyl.

11. wherein R3 is -hydrogen or —$CH_3$.

12. wherein R4 is —OH, -halogen, —$CF_2$H, —$CF_3$, —($C_1$-$C_3$)alkyl, or —OR9, provided that when X is nitrogen, then R4 and R5 are not attached to X.

13. wherein R4 is -hydrogen and R5 is -hydrogen or -halogen.

14. wherein R4 is -hydrogen and R5 is -hydrogen or —F.

15. wherein R6 is -halogen, —$CF_3$, or —($C_1$-$C_3$)alkyl.

16. wherein R6 is hydrogen or —($C_1$-$C_3$)alkyl.

17. wherein R6 is hydrogen or —$CH_3$.

18. wherein R7 and R8 are independently -hydrogen, -phenyl, —($C_1$-$C_7$)alkyl, or R7 and R8 combine with the nitrogen atom to which they are attached to form a 3 to 7 membered ring.

19. wherein R7 and R8 are -hydrogen, -phenyl, —($C_1$-$C_7$)alkyl, or R7 and R8 combine with the nitrogen atom to which they are attached to form a 4 to 6 membered ring.

20. R9 is -hydrogen, -halogen, —($C_1$-$C_3$)alkyl, or —OR7.

21. wherein R1 is selected from the group consisting of

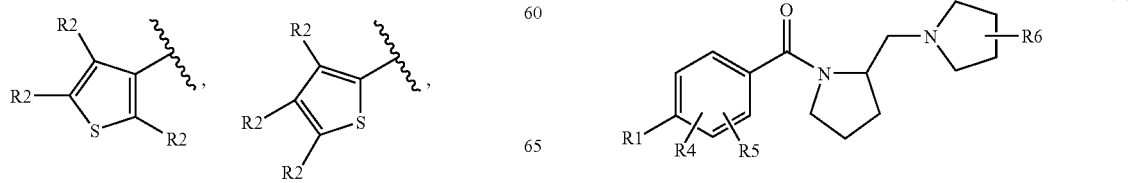

wherein the bond directed to the zig-zag lines indicates the point of attachment to the position indicated by R1 in Formula I; R2 is selected from the group consisting of -hydrogen, —CN, —C(O)R7, —C(O)NR7R8, —$SO_2$R7, —$SO_2$NR7R8, and —C(H)=NO—R7; R3 is -hydrogen, or —($C_1$-$C_7$)alkyl; R4 is hydrogen and R5 is hydrogen, or halogen; R6 is —H or —($C_1$-$C_3$)alkyl; R7 and R8 are -hydrogen, —($C_1$-$C_7$)alkyl, or R7 and R8 combine with the nitrogen atom to which they are attached to form a 4 to 6 membered ring.

In another embodiment the invention provides a compound structurally represented by Formula I

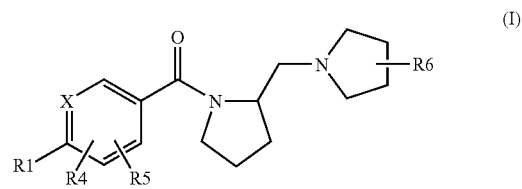

or pharmaceutically acceptable salts thereof wherein: X independently represents carbon or nitrogen: R1 is independently -HET, or -Benzofused heterocycle; R2 is independently at each occurrence —H, -halogen, —($C_1$-$C_7$)alkyl, —CN, —C(O)R7, —C(O)OR7, —C(O)($C_3$-$C_5$)cycloalkyl, —C(O)NR7R8, —O$CF_3$, —OR7, —$NO_2$, —NR7R8, —NR9$SO_2$R7, —NR9C(O)R7, —NR9$CO_2$R7, —NR9C(O)NR7R8, —SR7, —$SO_2$R7, —$SO_2CF_3$, —$SO_2$NR7R8, —S(O)R7, or -phenyl-R9; R3 is independently at each occurrence —H, —($C_1$-$C_7$)alkyl, -phenyl, -benzyl, —$SO_2$R7, —C(O)R7, —C(O)NR7R8, or —C(O)OR7; R4 and R5 are independently —H, —OH, -halogen, —$CF_2$H, —$CF_3$, —($C_1$-$C_3$)alkyl, or —OR9, provided that when X is nitrogen, then neither R4 or R5 are attached to X; R6 is independently —H, -halogen, —CF3, —($C_1$-$C_3$)alkyl, —$NH_2$, —NR7R8, —OH, —OR7; R7 and R8 are independently —H, ($C_1$-$C_7$)alkyl, wherein R7 and R8 can combine with the atom to which they are attached to form a 3 to 7 membered ring; R9 is —H, —($C_1$-$C_3$)alkyl.

In another embodiment the invention provides a compound structurally represented by Formula II or pharmaceutically acceptable salts thereof wherein:

R1 is independently HET; R2 is independently at each occurrence —H, -halogen, —($C_1$-$C_7$)alkyl, —CN, —C(O)R7, —C(O)OR7, —C(O)($C_3$-$C_5$)cycloalkyl, —C(O)NR7R8, —OCF$_3$, —OR7, —NO$_2$, —NR7R8, —NR9SO$_2$R7, —NR9C(O)R7, —NR9CO$_2$R7, —NR9C(O)NR7R8, —SR7, —SO$_2$R7, —SO$_2$CF$_3$, —SO$_2$NR7R8, —S(O)R7, or -phenyl-R9; R3 is independently at each occurrence —H, —($C_1$-$C_7$)alkyl, -phenyl, -benzyl, —SO$_2$R7, —C(O)R7, —C(O)NR7R8, or —C(O)OR7; R4 and R5 are independently —H, —OH, -halogen, —CF$_2$H, —CF$_3$, —($C_1$-$C_3$) alkyl, or —OR9, provided that when X is nitrogen, then neither R4 or R5 are attached to X; R6 is independently —H, -halogen, —CF3, —($C_1$-$C_3$)alkyl, —NH$_2$, —NR7R8, —OH, or —OR7; R7 and R8 are independently —H, ($C_1$-$C_7$)alkyl, wherein R7 and R8 can combine with the atom to which they are attached to form a 3 to 7 membered ring; R9 is —H, or —($C_1$-$C_3$)alkyl.

In preferred embodiments the invention provides a compound structurally represented by Formulae X1 to X57, including racemates and enantiomers, or a pharmaceutically acceptable salt thereof:

| Formula Number | Structure |
|---|---|
| X1 | 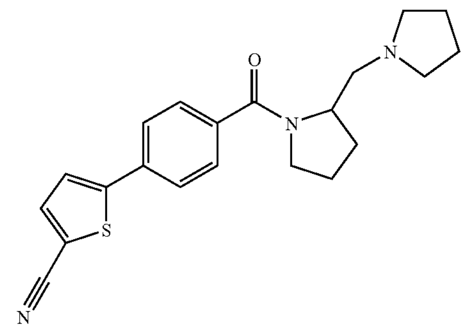 |
| X2 | 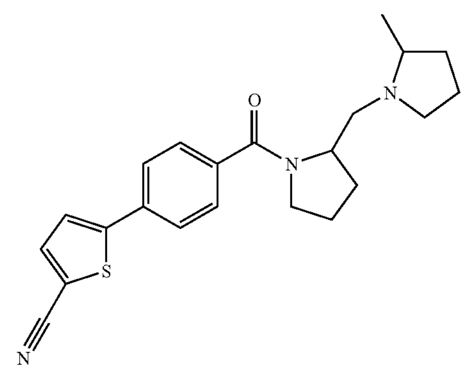 |
| X3 | 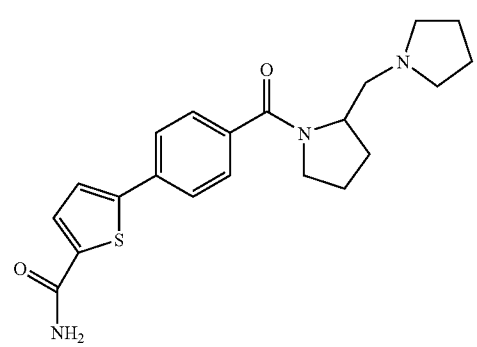 |

-continued
| Formula Number | Structure |
|---|---|
| X4 | 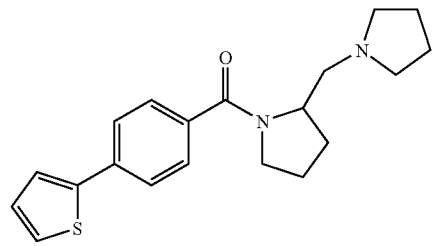 |
| X5 | 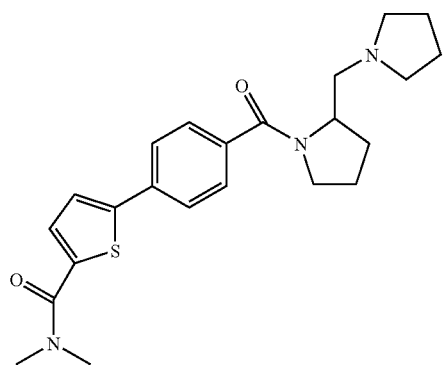 |
| X6 | 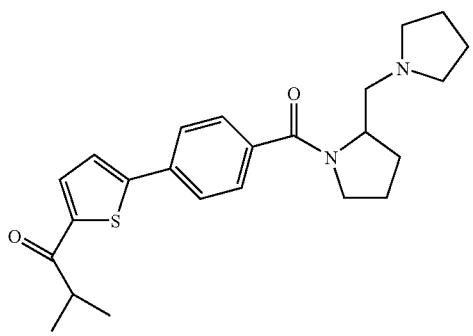 |
| X7 | 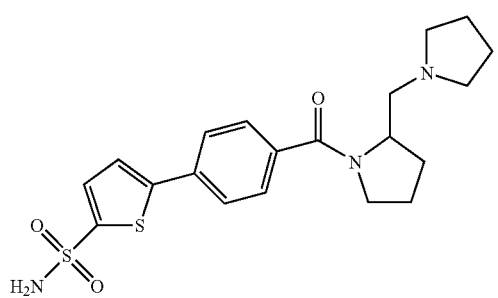 |

-continued
| Formula Number | Structure |
|---|---|
| X8 | 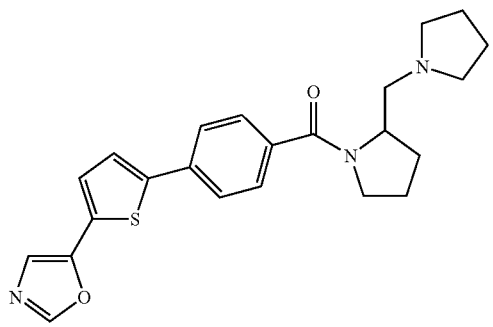 |
| X9 | 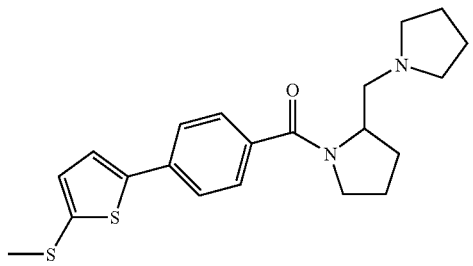 |
| X10 | 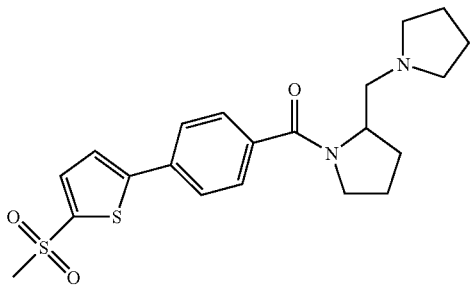 |
| X11 | 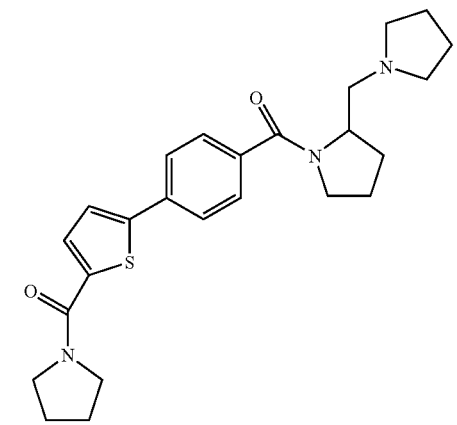 |

-continued
| Formula Number | Structure |
|---|---|
| X12 | 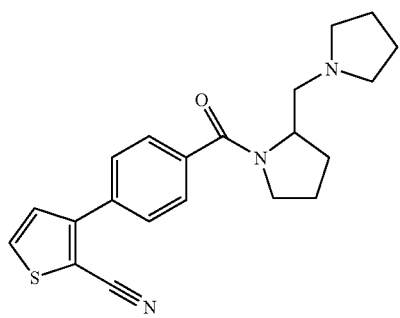 |
| X13 | 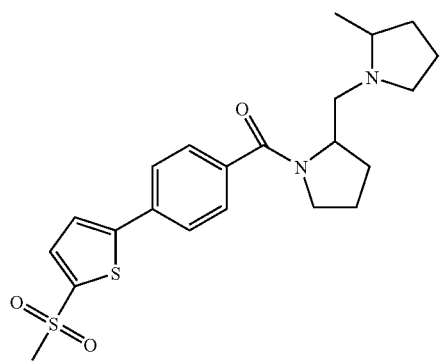 |
| X14 | 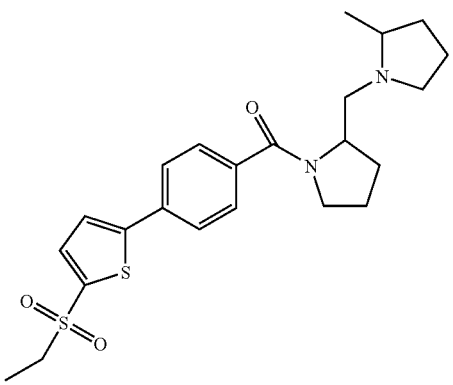 |
| X15 | 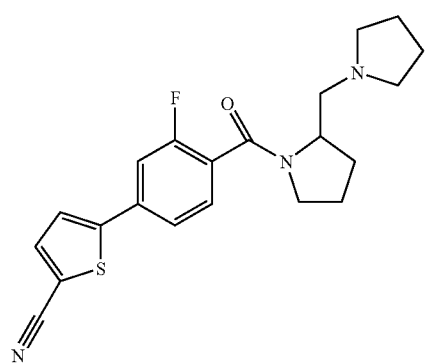 |

-continued
| Formula Number | Structure |
|---|---|
| X16 | 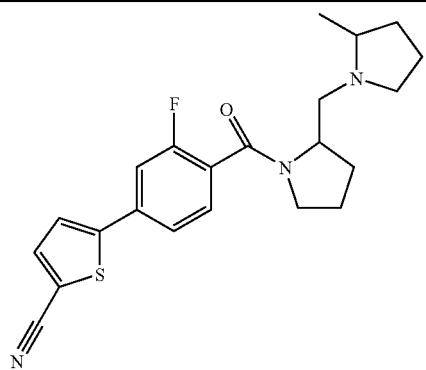 |
| X17 | 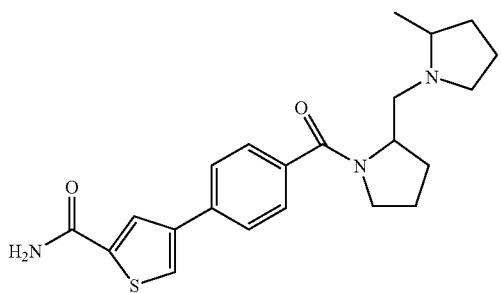 |
| X18 | 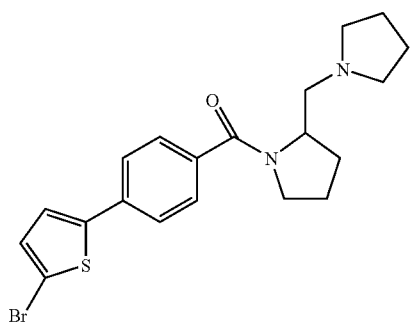 |
| X19 | 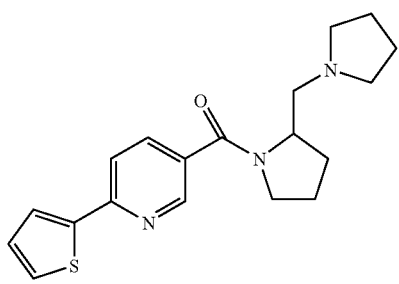 |
| X20 | 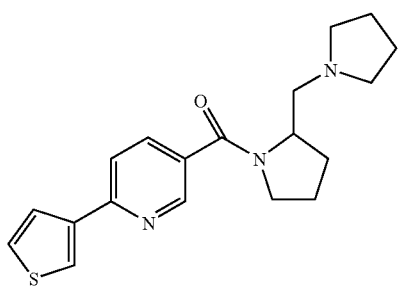 |

-continued
| Formula Number | Structure |
|---|---|
| X21 | 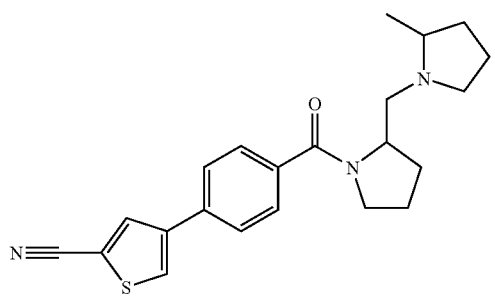 |
| X22 | 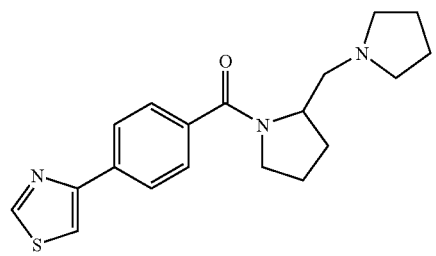 |
| X23 | 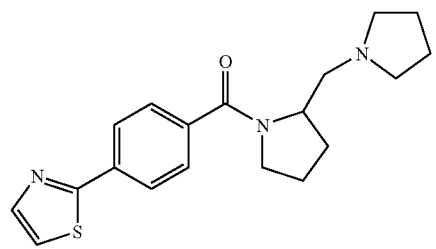 |
| X24 | 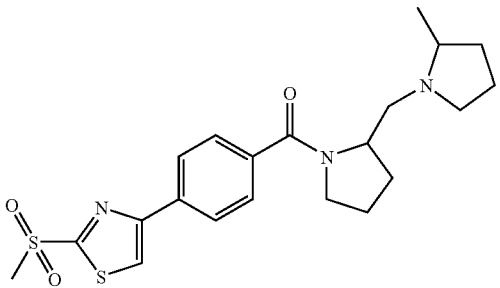 |
| X25 | 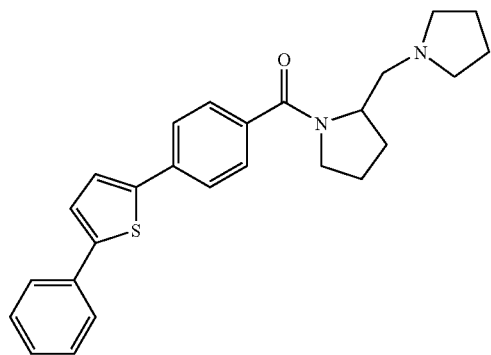 |

-continued
| Formula Number | Structure |
|---|---|
| X26 | 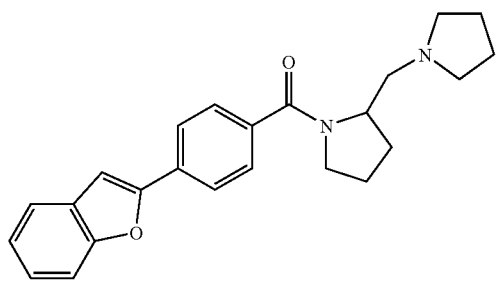 |
| X27 | 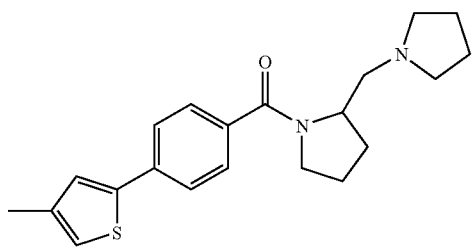 |
| X28 | 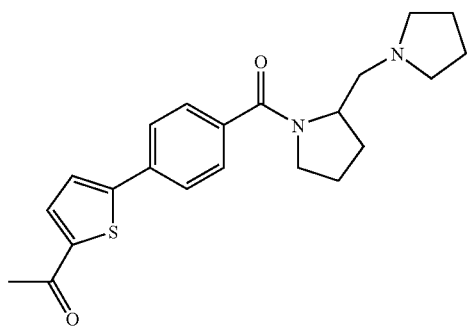 |
| X29 | 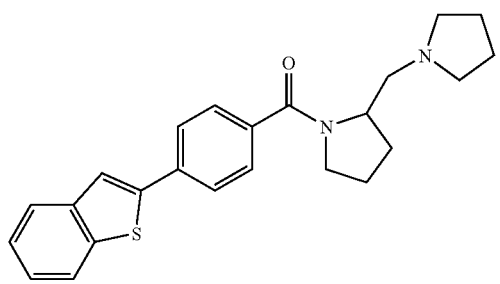 |
| X30 | 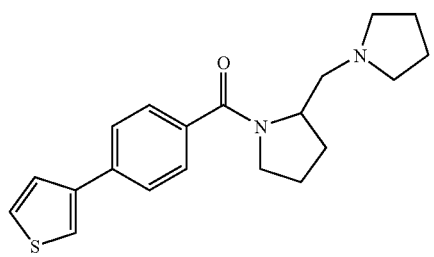 |

-continued
| Formula Number | Structure |
|---|---|
| X31 | 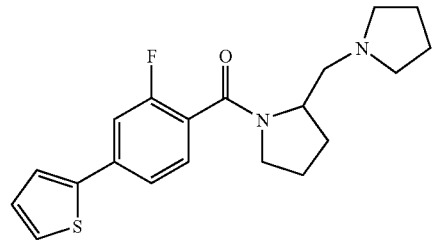 |
| X32 | 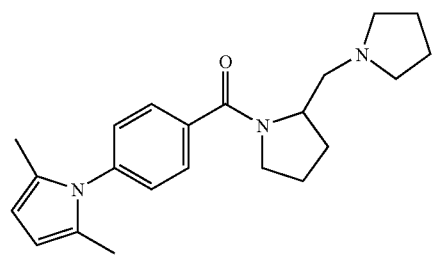 |
| X33 | 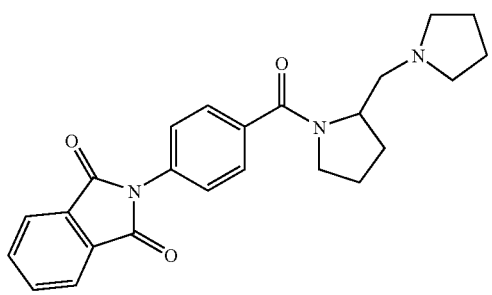 |
| X34 | 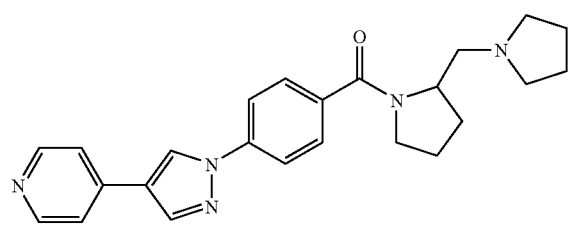 |
| X35 | 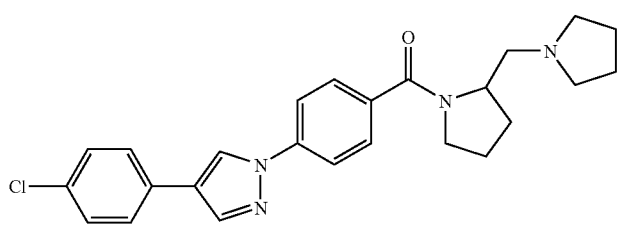 |
| X36 | 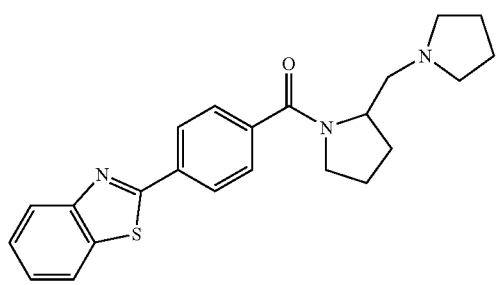 |

-continued
| Formula Number | Structure |
|---|---|
| X37 | 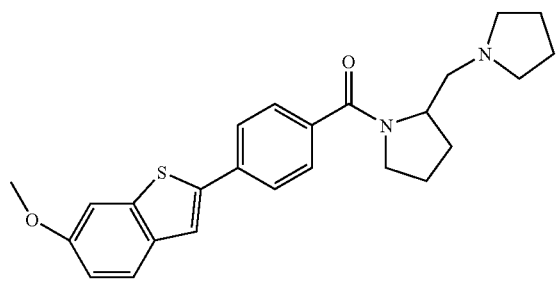 |
| X38 | 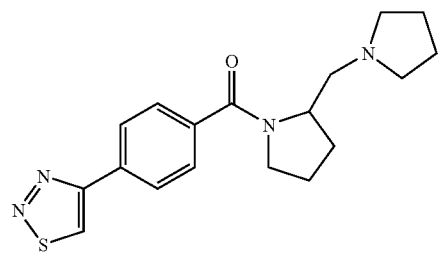 |
| X39 | 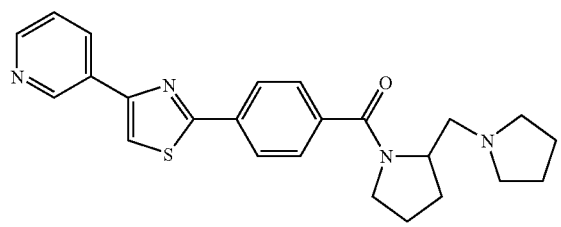 |
| X40 | 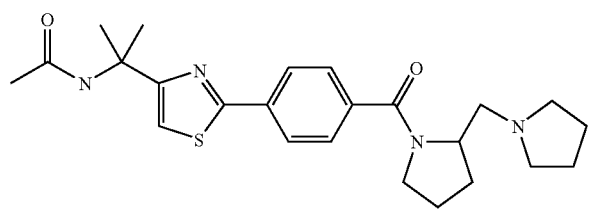 |
| X41 | 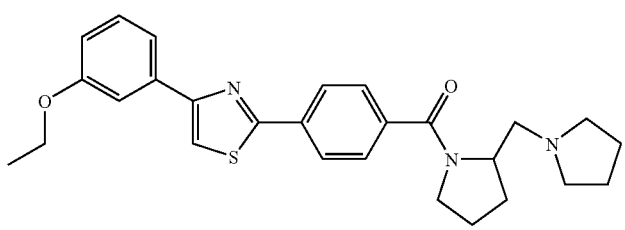 |

-continued
| Formula Number | Structure |
|---|---|
| X42 | 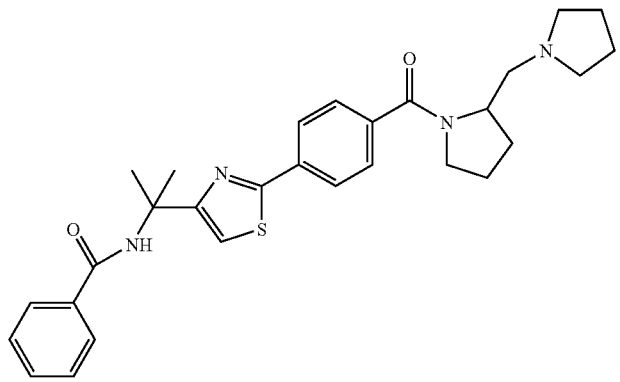 |
| X43 | 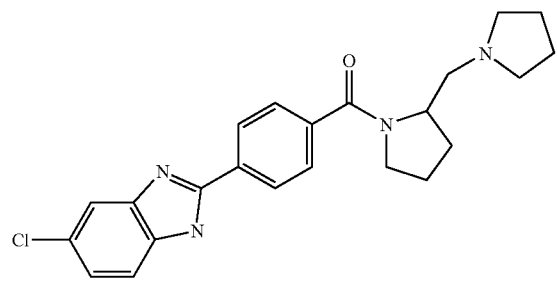 |
| X44 | 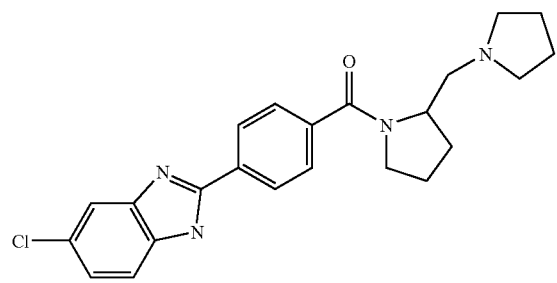 |
| X45 | 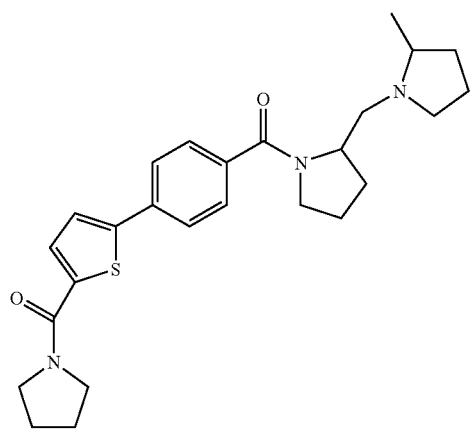 |

-continued
| Formula Number | Structure |
|---|---|
| X46 | 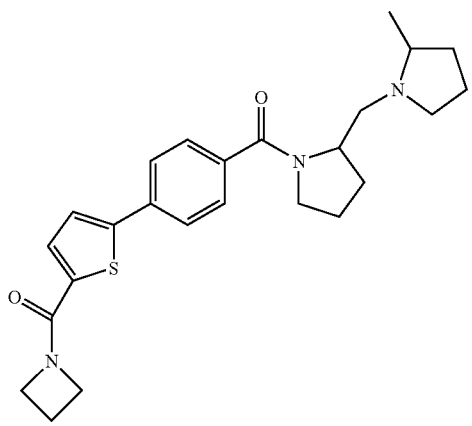 |
| X47 | 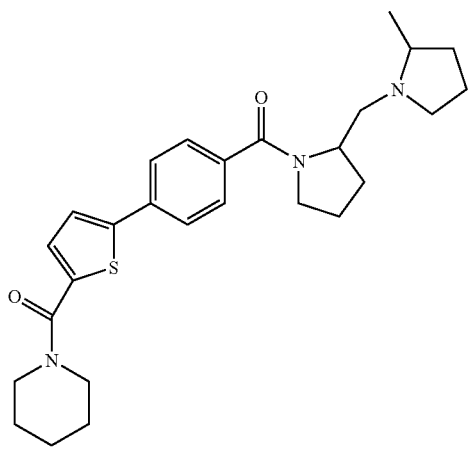 |
| X48 | 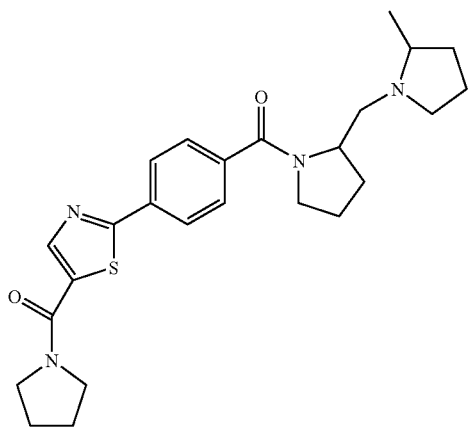 |

-continued
| Formula Number | Structure |
|---|---|
| X49 | 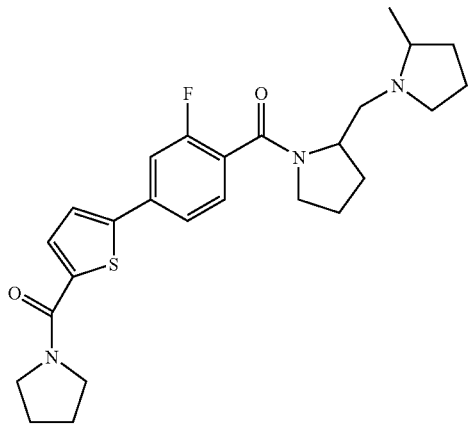 |
| X50 | 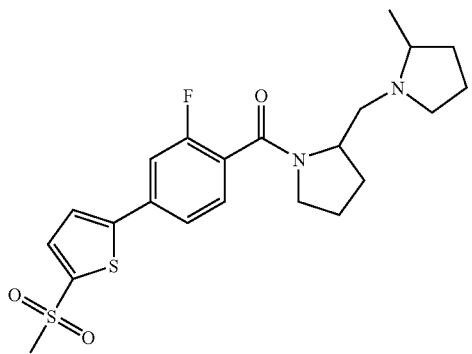 |
| X51 | 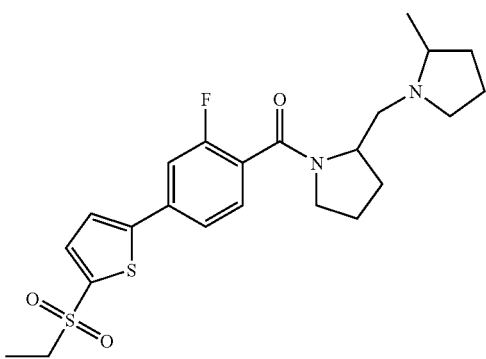 |
| X52 | 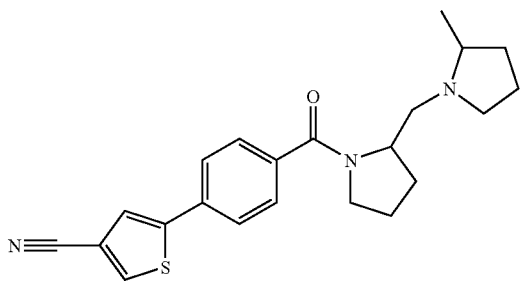 |

-continued
| Formula Number | Structure |
|---|---|
| X53 | 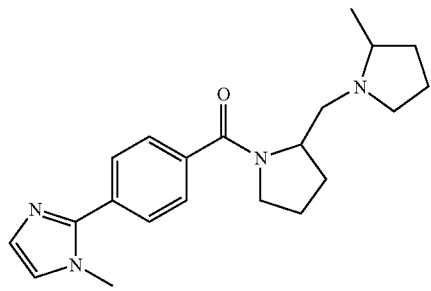 |
| X54 | 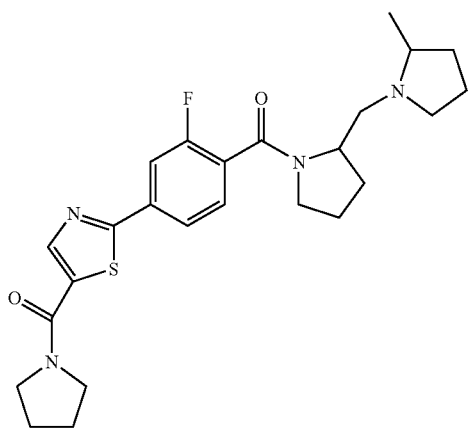 |
| X55 | 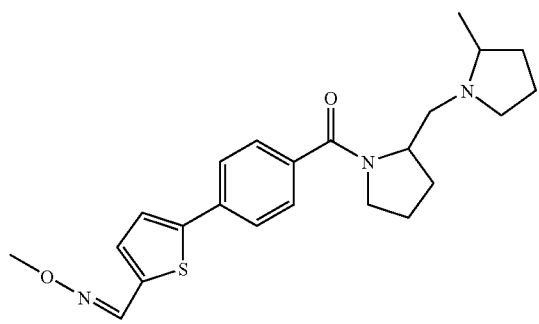 |
| X56 | 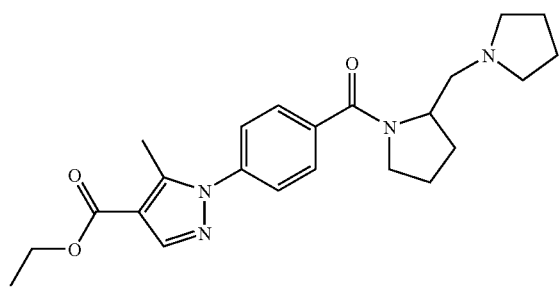 |

-continued

| Formula Number | Structure |
|---|---|
| X57 | 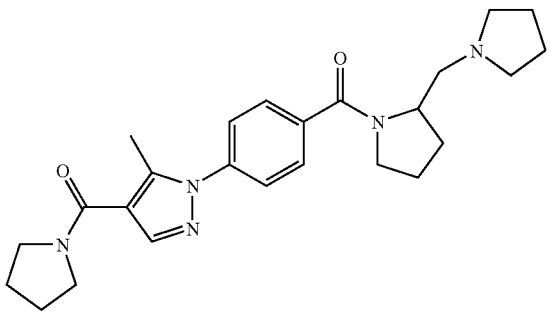 |

Due to their interaction with the histamine H3 receptor, the present compounds are useful in the treatment of a wide range of conditions and disorders in which an interaction with the histamine H3 receptor is beneficial. Thus, the compounds may find use for example to prevent, treat and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders which include but are not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like.

The present invention also provides a pharmaceutical composition which comprises a compound of Formula I or Formula II and a pharmaceutically acceptable carrier. Pharmaceutical formulations of Formula I or Formula II can provide a method of selectively increasing histamine levels in cells, or increasing histamine release by cells, by contacting the cells with an antagonist or inverse agonist of the histamine H3 receptor, the antagonist or inverse agonist being a compound of Formula I or Formula II. Thus, the methods of this invention encompass a prophylactic and therapeutic administration of a compound of Formula I or Formula II.

The present invention further provides an antagonist or inverse agonist of Formula I or Formula II which is characterized by having little or no binding affinity for the histamine receptor GPRv53.

Thus, a pharmaceutical preparation of Formula I or Formula II can be useful in the treatment or prevention of obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, which comprises administering to a subject in need of such treatment or prevention an effective amount of a compound of Formula I or Formula II. In addition, a pharmaceutical preparation of Formula I or Formula II can be useful in the treatment or prevention of a disorder or disease in which modulation of histamine H3 receptor activity has a beneficial effect or the treatment or prevention of eating disorders which comprises administering to a subject in need of such treatment or prevention an effective amount of a compound of Formula I or Formula II. In yet another aspect, the present invention provides compounds, pharmaceutical compositions, and methods useful in the treatment of nervous system and other disorders associated with histamine. H3 receptor.

In addition, the present invention relates to a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity; and for use in treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo. Thus, the uses and methods of this invention encompass a prophylactic and therapeutic administration of a compound of Formula I or II.

The present invention is further related to the use of a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

The present invention further provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formula I or II or a pharmaceutically acceptable salt thereof, or a pharmaceutical composition which comprises a compound of Formula I or II, or a pharmaceutical salt thereof, and a pharmaceutically acceptable carrier, diluent, or excipient.

The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formula I or II, or a pharmaceutical salt thereof, and a pharmaceutically acceptable carrier, diluent, or excipient. In addition, a pharmaceutical composition of Formula I or II can be useful in the treatment or prevention of a disorder or disease in which modulation of histamine H3 receptor activity has a beneficial effect. The present invention further provides an antagonist or inverse agonist of Formula I or II which is characterized by having greater affinity for the histamine H3 receptor as compared to the affinity for the histamine H1R, H2R, or H4R receptors. In addition the embodiments of the present invention include the synthesis of the examples named herein by methods included herein, and supplemented by methods known in the art, to create positron emission topography (PET) ligands that bind to histamine H3 receptors and are useful for PET imaging.

The invention includes tautomers, enantiomers, and other stereoisomers of the compounds. Thus, as one skilled in the art knows, certain aryls may exist in tautomeric forms. Such variations are contemplated to be within the scope of the invention. It will be understood that, as used herein, references to the compounds of Formula I or Formula II are meant to also include enantiomers and racemic mixtures, and the pharmaceutical salts thereof.

As used herein, the term "stereoisomer" refers to a compound made up of the same atoms bonded by the same bonds but having different three-dimensional structures. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or Formula II can be prepared by one of ordinary skill in the art utilizing well known techniques and processes, such as those disclosed by J. Jacques, et al., "*Enantiomers, Race-* mates, and Resolutions," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers, and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation "⎯" refers to a bond that protrudes forward out of the plane of the page. The designation "‖‖‖" refers to a bond that protrudes backward out of the plane of the page. The designation "⤳" refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I or Formula II which are substantially non-toxic to living organisms. See, e.g., Berge, S. M, Bighley, L. D., and Monkhouse, D. C., "Pharmaceutical Salts," *J. Pharm. Sci.*, 66:1, 1977. Typical pharmaceutical salts include those salts, prepared by reaction of the compounds of Formula I or Formula II with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or Formula II prepared by reaction of a compound of Formula I or Formula II with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I or Formula II with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I or Formula II prepared by reaction of a compound of Formula I or Formula II with a mineral or organic base. For exemplification of pharmaceutical base addition salts see, e.g., Berge, S. M, Bighley, L. D., and Monkhouse, D. C., *J. Pharm. Sci.*, 66:1, 1977. The present invention also contemplates pharmaceutical base addition salts of compounds of Formula I or Formula II. The skilled artisan would appreciate that some compounds of Formula I or Formula II may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I or Formula II.

The compounds of Formula I or Formula II, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I or Formula II may be obtained by stereospecific synthesis using optically pure starting materials or reagents of known configuration or through enantioselective synthesis.

The compounds of Formula I or Formula II can be prepared by one of ordinary skill in the art following a variety of procedures, some of which are illustrated in the procedures and schemes set forth below. The particular order of steps required to produce the compounds of Formula I or Formula II is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS (FD)" refers to field desorption mass spectrometry, "MS (IS)" refers to ion spray mass spectrometry, "MS (FIA)" refers to flow injection analysis mass spectrometry, "MS (FAB)" refers to fast atom bombardment mass spectrometry, "MS (EI)" refers to electron impact mass spectrometry, "MS (ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

"HOBt" is 1-hydrobenzotriazole. "PS-Carbodiimide" or "PS-CDI" is N-Cyclohexylcarbodiimide-N'-propyloxymethyl polystyrene. "EDC" is 1-Ethyl-3-[3-dimethylaminopropyl]carbodiimide hydrochloride. "HATU" is O-(7-azabenzotriazol-1-yl)-N—N—N'—N'-tetramethyluronium hexafluorophosphate. "TBTU" is 1H-Benzotriazolium, 1-[bis(dimethylamino)methylene]-, tetrafluoroborate(1-), 3-oxide O-(Benzotriazol-1-yl)-N,N,N',N'-tetramethyluronium tetrafluoroborate. "THF" is tetrahydrofuran. "DMF" is dimethylformamide. "EtOH" is ethyl alcohol or ethanol. "EtOAc" is ethyl acetate. "DIEA" is diisopropylethyl amine. "SCX" is strong cation exchange. "MeOH" is methyl alcohol or methanol. "DCC" is dicyclohexylcarbodiimide. "DME" is ethylene glycol dimethyl ether.

General Schemes

Compounds of the present invention have been formed as specifically described in the examples. Further, many compounds are prepared using the general schemes described below. Unless otherwise indicated, all variables are defined as in the summary of the invention and as otherwise defined herein, or as for analogously positioned variables in the summary of the invention. Alternative synthesis methods may also be effective and known to the skilled artisan.

SCHEME A

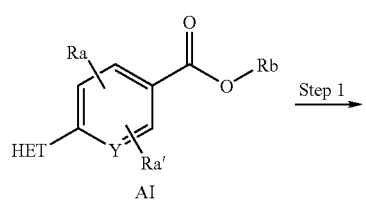

-continued

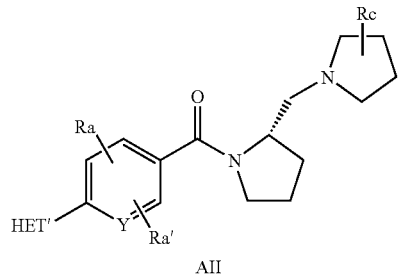

In Scheme A, $R_a$ and $R_{a'}$, are each independently but not limited to F, Cl, $CF_3$, alkyl and can include disubstituted compounds; $R_b$ is H, or the corresponding salts; $R_c$ can be but is not limited to alkyl, amino, hydroxy, HET' is any 5-membered heteroaromatic ring or "benzofused" heterocycles not limited to furan, imidazole, isothiazole, isoxazole, oxadiazole, oxazole, pyrazole, pyrrole, tetrazole, thiadiazole, thiazole, thiophene and triazole, benzoxazole, benzimidazole, benzofuran, benzothiophene, benzothiazole, azaindole, and indole, indazole, as well as the structures indicated as R1 herein, and Y can be nitrogen or carbon. In Scheme A, Step 1, the carboxylic acids of formula AI or the lithium, sodium or potassium salt of the acid where $R_b$ can be H, Li, Na or K are converted to the corresponding amides of formula AII using a number of different methods known in the literature. Some of these methods can be found described in a review of coupling reagents in peptide synthesis by Klausner & Bodansky, Synthesis, 1972, 9, 453-463.

For example, 4-(thiophen-2-yl)-benzoic acid (where HET'=thiophen-2-yl) or the corresponding lithium or sodium salt is suspended a suitable organic solvent such as dichloromethane, DMF or mixtures thereof. A suitable amide coupling agent i.e. EDC, DCC, TBTU, etc., is added followed by HOBt, HATU, etc., at room temperature. Diisopropylethyl amine and suitable amine in this case, (S)(+)-1-(2-pyrrolidinylmethyl)pyrrolidine are added to the mixture. The mixture is stirred at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt of formula I using thionyl chloride or oxalyl chloride and a few drops DMF, in a suitable solvent, e.g. THF, toluene, dichloromethane, or chloroform, by stirring within a temperature range of 10 to 100° C. for a period of 0.5 to 24 hours. The reaction is concentrated and the crude acid chloride is treated with a suitable amine and a proton scavenger, e.g. triethylamine, pyridine etc., to give the desired amide (AII).

For example, sodium-4-(4-pyridin-3-yl-thiazol-2-yl)-benzoic acid is slurried in a suitable solvent such as toluene with oxalyl chloride, and catalytic dimethylformamide. The mixture is heated to reflux for 2 minutes and then allowed to stir at ambient temperature for 2 hours. The reaction is concentrated, triturated with dichloromethane, and is concentrated to give the acid chloride intermediate which is used without purification. The acid chloride is dissolved in dichloromethane and added to a mixture of (S)-(+)-1-(2-pyrrolidinyl-methyl)pyrrolidine and pyridine and stirred for 20 minutes. The resulting mixture may be concentrated, extracted, and purified according to techniques well known in the art.

SCHEME B

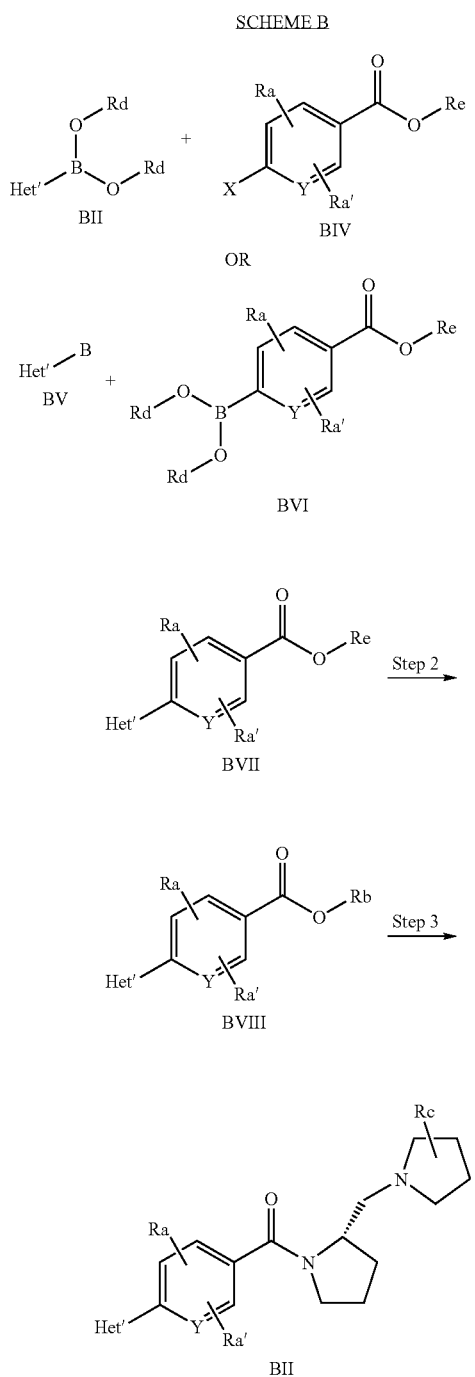

In Scheme B, $R_a$, $R_{a'}$, $R_b$, $R_c$, Het', and Y are as defined previously. $R_d$ can be H, alkyl or cycloalkyl; $R_e$ can be and is not limited to H or the corresponding methyl, ethyl, benzyl esters. In Scheme B (step 1), aryl esters or acids of formula BIV (wherein $R_e$=Methyl, Ethyl, H) substituted with halogen X, where X can be Cl, Br, or I combined with an heteroaromatic boronic acid of formula BIII (wherein $R_d$=H) or ester (wherein $R_d$=pinacol) are converted to the corresponding heteroaromatic-aryl compound of formula BVII. Alternatively, in Scheme B (step 1), heteroaromatic chlorides, bromides or iodides of formula BV can be combined with aryl acid or ester substituted boronates (wherein $R_d$=pinacol) or boronic acids of formula BVI (wherein $R_d$=H) to give the corresponding heteroaromatic-aryl compound of formula BVII. Both routes to these heteroaromatic-aryl compounds (BVII) can be achieved by a variety of palladium catalyzed Suzuki reaction methods as described in Section IV-14 of the following review (Hassan, Jwanro; Sevignon, Marc; Gozzi, Christel; Schulz, Emmanuelle; Lemaire, Marc; Aryl-Aryl Bond Formation One Century after the Discovery of the Ullmann Reaction. Chemical Reviews (Washington, D.C.) (2002), 102 (5), 1359-1469). For example, 5-Bromo-thiophene-2-sulfonic acid amide and 4-methoxycarbonylphenyl boronic acid are dissolved in a suitable organic solvent such as dioxane, acetonitrile, DME, THF, Ethanol, or mixtures thereof. A suitable palladium catalyst such as tetrakis-(triphenylphosphine) palladium (0), palladium (II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4 to 24 hours. The reaction is concentrated and purified according to techniques well known in the art.

Alternatively, the heteroaromatic-aryl compound (BVII) formation (step 1) can also be performed using microwave assisted Suzuki couplings. For example 1-(5-bromothiophen-2-yl)-2-methyl-propan-1-one and 4-methoxycarbonylphenyl boronic acid are dissolved in a suitable organic solvent such as dioxane, acetonitrile, DME, THF, Ethanol, or mixtures thereof. A suitable palladium catalyst such as tetrakis-(triphenylphosphine) palladium (0), palladium (II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is run in a CEM® or MARS® microwave reactor for 10 to 40 minutes, at 90 to 120° C., with 75 W power and cooling control on to maintain temperature range. The reaction is concentrated and purified according to techniques well known in the art.

In Scheme B, Step 2, the resulting esters (BVII) (wherein $R_e$=Methyl, Ethyl, Benzyl etc.), can be saponified using standard conditions to yield the corresponding heteroaromatic-aryl carboxylic acids or the lithium, sodium or potassium salt of the acid of the corresponding formula BVIII where $R_b$ can be H, Li, Na or K. For example 4-(5-isobutyryl-thiophen-2-yl)-benzoic acid methyl ester is dissolved in a suitable solvent such as methanol or dioxane and aqueous LiOH is added. The reaction mixture is stirred at room temperature overnight or can be heated to 50° C. for 30 min to 18 hours. The solvent is removed in vacuo and the acid or salt isolated according to techniques well known in the art.

In Scheme B (step 3), the carboxylic acids or the corresponding lithium, sodium or potassium salts (BVIII) (wherein $R_b$=H, Li, Na, K are converted to the amides (BII) by the methods described in Scheme A (step 1).

SCHEME C

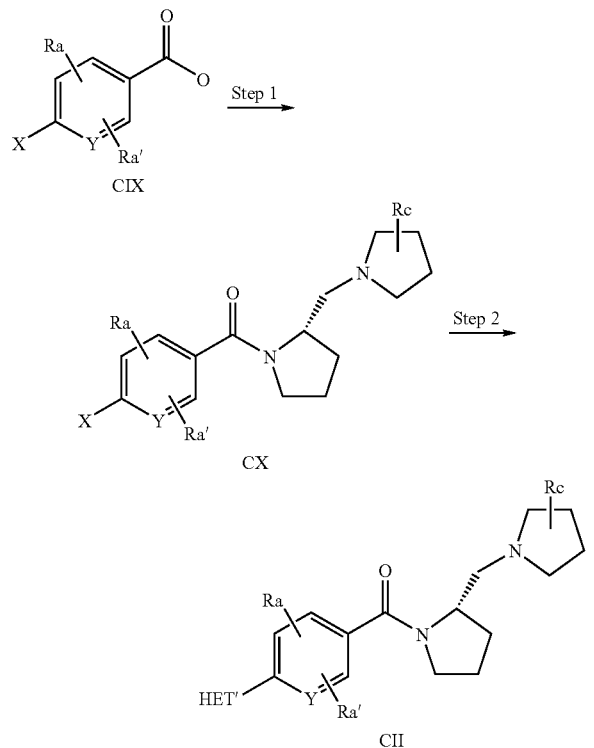

SCHEME D

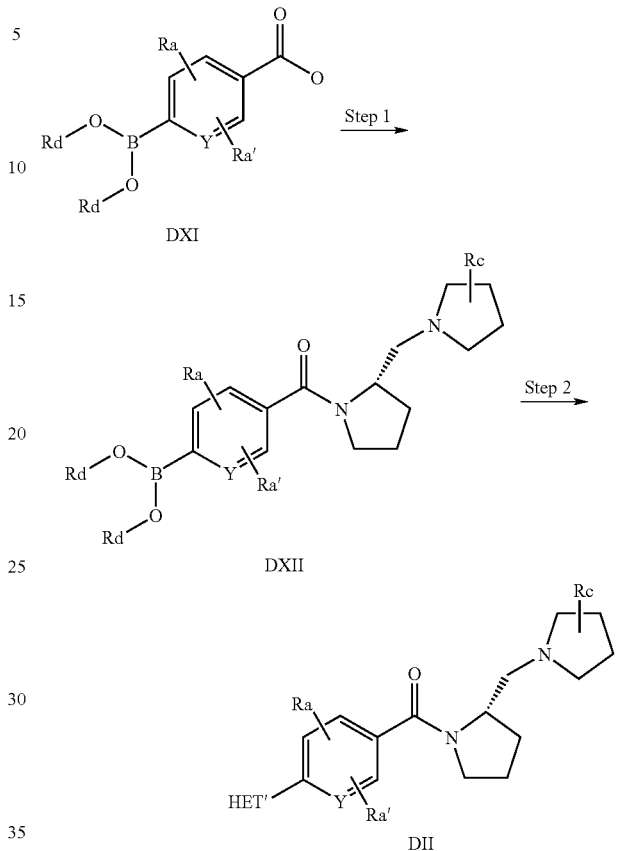

In Scheme C, $R_a$, $R_{a'}$, $R_c$, Ar, X and Y are as defined previously. In Scheme C (step 1), the carboxylic acids of formula CIX are converted to the amides of formula CX by the methods described in Scheme A (step 1).

For example, 4-bromobenzoic acid-2,5-dioxo-pyrrolidin-1-yl ester [which can be prepared from 4-bromobenzoic acid and N-hydroxy succinamide by standard conditions (C. Mitsos, Chem Pharm Bull 48(2), 211-214 (2000)] in a suitable solvent such as tetrahydrofuran, is added a suitable amine in this case (S)-(+)-1-(2-pyrrolidinylmethyl)pyrrolidine and the reaction mixture is heated to reflux for a period of 1-12 hours. The reaction is concentrated and purified according to techniques well known in the art.

In Scheme C (step 2) these heteroaromatic-aryl amides (CII) can be achieved by a variety of palladium catalyzed Suzuki reaction methods as described under Scheme B. For example, 4-(2-pyrrolidin-1-ylmethyl-pyrrolidine-1-carbonyl)-phenyl bromide and 5-phenyl-2-thienyl boronic acid are dissolved in a suitable organic solvent such as dioxane, acetonitrile, DME, THF, Ethanol, or mixtures thereof. A suitable palladium catalyst such as tetrakis-(triphenylphosphine) palladium (0), palladium(II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4 to 24 hours, alternatively reaction is run in a CEM® or MARS® microwave reactor for 10 to 40 minutes, at 90 to 110° C., with 75 W power and cooling control on to maintain temperature range. The reaction is concentrated and purified according to techniques well known in the art.

In Scheme D, $R_a$, $R_{a'}$, $R_c$ and $R_d$, Y and HET' are as previously defined. In Scheme D (step 1), pyrrolidinylmethylpyrrolidine or methylpyrrolidinylmethylpyrrolidine amides (DXII) of commercially available (Aldrich) 4-(4,4,5,5-Tetramethyl-[1,3,2]dioxaborolan-2-yl)-benzoic acid can be prepared by the acid chloride procedure in Scheme A, step 1. For example, 4-(4,4,5,5-tetramethyl-[1,3,2]dioxaborolan-2-yl)-benzoic acid is dissolved in 10 mL of $CH_2Cl_2$ with 4-5 drops of DMF and stirred while oxalyl chloride is added. Reaction is refluxed for a period of 1-12 hours and excess oxalyl chloride is removed in vacuo. The residue is dissolved in a suitable solvent in this case $CH_2Cl_2$ to make acid chloride solution and is added to a solution of a suitable amine in this case 2-(R)-methyl-1-(2-(S)-pyrrolidinylmethyl)pyrrolidine and a proton scavenger i.e. triethylamine in $CH_2Cl_2$. The mixture is stirred at room temperature for a period of 30 minutes to 12 hours. The resulting mixture may be concentrated, extracted, and purified according to techniques well known in the art.

In Scheme D (step 2) the boronic ester (DXII) formed in Scheme D (step 1) can be converted to heteroaromatic-aryl amide (DII) using the Suzuki coupling methods described in Schemes B and C. For example, 4-bromo-thiophene-2-carbonitrile and [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone are dissolved in a suitable organic solvent such as dioxane, acetonitrile, DME, THF, EtOH (ethanol), or mixtures thereof. A suitable palladium catalyst such as tetrakis-(triphenylphosphine) palladium (0), palladium (II) dichloride (dppf) complex with dichloromethane, dichloropalladium di-triphenylphosphine etc., is added followed by a suitable base such as aqueous sodium or potassium carbonate, anhydrous cesium or potassium fluoride, anhydrous potassium or cesium carbonate etc. The reaction is the reaction is heated within a temperature range of 70 to 100° C. for a period of 4 to 24 hours, or alternatively run in a CEM® or MARS® microwave reactor for 10 to 40 minutes, at 90 to 120° C., with 75 W power and cooling control on to maintain temperature range. The reaction is concentrated and purified according to techniques well known in the art.

SCHEME E

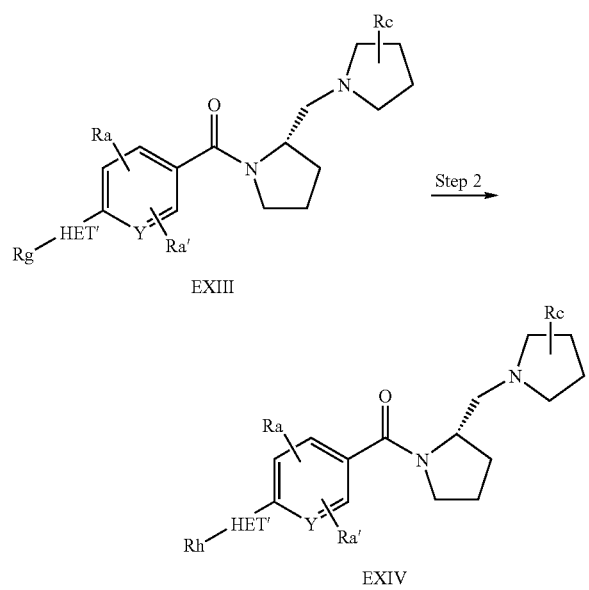

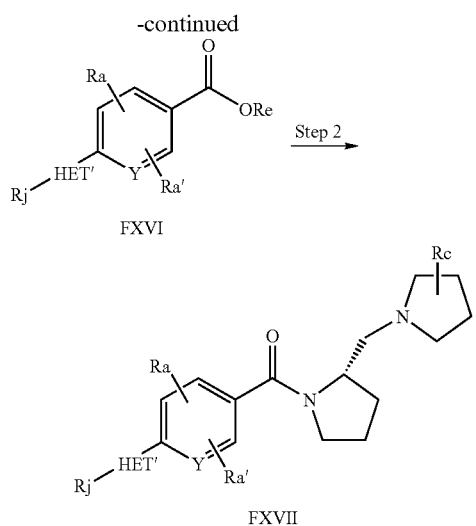

In Scheme E, $R_a$, $R_{a'}$, $R_c$ and Y are as previously defined. $R_g$ is any functional group that can be further modified to $R_h$ via alkylation, acylation, oxidation, reduction, sulfonylation etc. In Scheme E (step 1), wherein $R_g$=nitrile, $R_g$ can be converted to a primary amide using known oxidation conditions. For example, 1.5 mL DMSO solution of 5-[4-(2(S)-pyrrolidin-1-ylmethyl-pyrrolidine-1-carbonyl)-phenyl]-thiophene-2-carbonitrile ($R_g$=CN) is stirred at room temperature while $K_2CO_3$ (55 mg, 0.4 mmol) and 0.2 mL $H_2O$ is added, then 30% $H_2O_2$ and is stirred one hour. The reaction is concentrated and purified according to techniques well known in the art.

SCHEME F

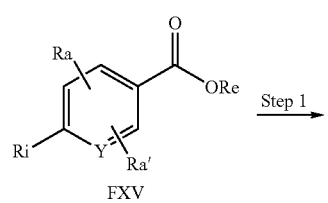

In Scheme F, $R_a$, $R_{a'}$, $R_e$ and Y are as previously defined. $R_i$ is any functional group that can be further cyclized with suitable reagents to form a heterocycle not limited to acid chloride, acid, amide, urea, thiourea etc and $R_j$ can be but is not limited to alkyl, aryl, cyano, sulfone, sulfonamide, amide etc. For example, in Scheme F, Step 1, 4-thiocarbamoyl-benzoic acid ethyl ester ($R_i$=thioamide) is heated with 2-bromo-1-pyridin-3-yl-ethanone; hydrobromide to provide the corresponding thiazole (FXVI, where $R_j$=pyridine). The reaction is concentrated and purified according to techniques well known in the art. In Scheme F (step 2), the compounds (FXVI) are converted to the amides (FXVII) by the methods described in Scheme A & B Procedures:

General Procedure A: Suzuki Type Coupling A

A mixture of the aryl halide (1 eq), the boronic acid or boronic ester (1.1-1.2 eq.), tetrakis (triphenylphosphine) palladium (0) (0.05-0.1 eq.), and 2M $Na_2CO_3$ (2.2 eq.) in 0-20% EtOH/dioxane (degassed by vacuum, then $N_2$ purge) is stirred 8-48 hours at 80-90° C. Reaction is allowed to cool, diluted with an organic solvent, e.g. $CH_2Cl_2$ or EtOAc, washed with aq. $NaHCO_3$ and brine, dried ($Na_2SO_4$) and concentrated in vacuo. The crude mixture is purified by chromatography to give the desired product.

General Procedure B: Suzuki Type Coupling B

A mixture of the aryl halide (1 eq), the boronic acid or boronic ester (1.1-1.2 eq.), tetrakis (triphenylphosphine) palladium (0) (0.05-0.1 eq.), and 2M $Na_2CO_3$ (2.2 eq.) in 0-20% EtOH/dioxane is stirred in a CEM® Microwave Reactor 30-40 minutes at 80-90° C. Microwave session is repeated until aryl halide is consumed. Reaction is diluted with an organic solvent, e.g. $CH_2Cl_2$ or EtOAc, washed with aq. $NaHCO_3$ and brine, dried ($Na_2SO_4$) and concentrated in vacuo. The crude mixture is purified by chromatography to give the desired product.

General Procedure C: Methyl Ester Hydrolysis

A mixture of the methyl ester and lithium hydroxide monohydrate is stirred in 10-25% aqueous dioxane or 10-25% aqueous tetrahydrofuran for 4-96 hours until the methyl ester is consumed. The reaction mixture is concentrated and dried in vacuo. The carboxylic acid lithium salt is used without further purification or is converted to the carboxylic acid by adding H$_2$O, washing with diethylether, adjusting the aqueous layer pH to ~2.0 with 1 N HCl, then filtering and drying the free acid in vacuo.

General Procedure D: Amide Formation

The carboxylic acid or carboxylic acid Lithium salt (1.1-1.2 eq.) is stirred in 0-50% DMF/CH$_2$Cl$_2$ as the EDC-HCl (1.5 eq.) is added portionwise, then the HOBt (1.5 eq.) and reaction is stirred at room temperature for 30-60 minutes. The DIEA (2.5 eq) and amine (1 eq.) is added and reaction stirred 8-72 hours. Reaction is diluted with CH$_2$Cl$_2$, washed with aq. NaHCO$_3$ and brine, dried (Na$_2$SO$_4$) and concentrated in vacuo. The crude mixture is purified by SCX chromatography (MeOH wash, then elution with 2M NH$_3$/MeOH) and/or silica gel column chromatography (gradient: 100% CH$_2$Cl$_2$ to 10% 2M NH$_3$ in MeOH/CH$_2$Cl$_2$) to give the desired product.

General Procedure E: Amide Formation

The carboxylic acid (1.1 eq.) in CH$_2$Cl$_2$ is stirred at room temperature under N$_2$, a few drops DMF are added, and the oxalyl chloride (2.5 eq) is added dropwise. Reaction is stirred at 22-40° C. for 30-120 minutes, then concentrated, redissolved in CH$_2$Cl$_2$, and concentrated. A CH$_2$Cl$_2$ solution of the crude acid chloride is added dropwise to a CH$_2$Cl$_2$ solution of the amine (1 eq.) and triethylamine (2.1 eq.) and stirred at room temperature for 4-24 hours. Reaction is diluted with CH$_2$Cl$_2$, washed with aq. NaHCO$_3$ and brine, dried (Na$_2$SO$_4$) and concentrated in vacuo. The crude mixture is purified by SCX chromatography (MeOH wash, then elution with 2M NH$_3$/MeOH) and/or silica gel column chromatography (gradient: 100% CH$_2$Cl$_2$ to 10% 2M NH$_3$ in MeOH/CH$_2$Cl$_2$) to give the desired product.

General Procedure: Chromatography Purification

SCX chromatography—(MeOH wash, then elution with 2M NH$_3$/MeOH).

Silica gel column chromatography—(gradient: 100% CH$_2$Cl$_2$ to 10% 2M NH$_3$ in MeOH/CH$_2$Cl$_2$); (gradient: 100% hexane to 50% EtOAC/hexane); or (gradient: 100% CH$_2$Cl$_2$ to 20% EtOAC/CH$_2$Cl$_2$).

Intermediate Preparation 1

2-(R)-Methyl-1-(2-(S)-pyrrolidinylmethyl)pyrrolidine

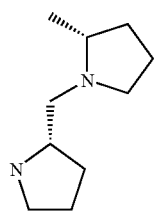

(S) BOC proline (CAS 15761-39-4) and 2-(R)-Methyl-pyrrolidine hydrochloride (CAS 135324-85-5) are coupled in a manner substantially analogous to General Procedure D in dichloromethane to give 2(S)-(2(R)-Methyl-pyrrolidine-1-carbonyl)-pyrrolidine-1-carboxylic acid tert-butyl ester (233179). The material is deprotected by stirring in dichloromethane at 5-10° C. while trifluoroacetic acid (10 eq) is added and then stirred at room temperature for 18 hours. Reaction is concentrated and dissolved in H$_2$O. The pH is adjusted to 8-9 with K$_2$CO$_3$, and the aqueous layer is extracted several times with CH$_2$Cl$_2$. The extracts are combined, dried (Na$_2$SO$_4$) and concentrated in vacuo to give (2(R)-Methyl-pyrrolidin-1-yl)-pyrrolidin-2-yl-methanone.

A 1 M Lithium Aluminum Hydride/THF solution (3 eq.) is diluted with an equal volume of THF and stirred under N$_2$. A THF solution of (2(R)-methyl-pyrrolidin-1-yl)-pyrrolidin-2-yl-methanone is added dropwise, allowing the reaction to mildly exotherm. The reaction is stirred at 40° C. for 45 minutes, then at room temperature 18 hours. Reaction is cooled in an ice bath and is quenched with H$_2$O (3 eq.), 4 N NaOH (3 eq.), then H$_2$O (9 eq.) while keeping reaction temperature less than 15° C. Reaction is stirred overnight, is filtered and the precipitate is washed three times with THF. The filtrate and washes are combined and concentrated to give 2-(R)-methyl-1-(2-(S)-pyrrolidinylmethyl)pyrrolidine. MS (ES+) 169.3 (M+H)$^+$ Intermediate is used as such or is purified by SCX chromatography or distillation.

Intermediate Preparation 2

4-(5-Dimethylcarbamoyl-thiophen-2-yl)-benzoic acid methyl ester

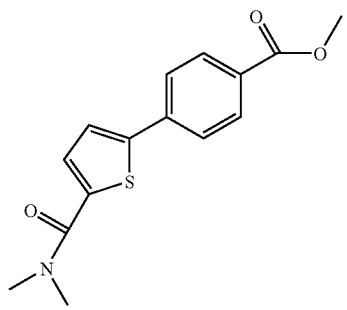

The title intermediate is prepared in a manner substantially analogous General Procedure B in 6 mL dioxane using a mixture of the 5-bromo-thiophene-2-carboxylic acid dimethylamide (CAS 474711-51-8) (163 mg, 1.0 mmol), 4-methoxycarbonylphenyl boronic acid (198, 1.1 mmol), tetrakis(triphenylphosphine)palladium (0) (58 mg, 0.05 mmol), and 2M Na$_2$CO$_3$ (1.1 mL, 2.20 mmol) in two consecutive 30 minute microwave sessions to give the desired intermediate. (150 mg, 52% yield) MS (ES+) 290.3 (M+H)$^+$ Intermediate Preparation 3

4-(5-Dimethylcarbamoyl-thiophen-2-yl)-benzoic acid

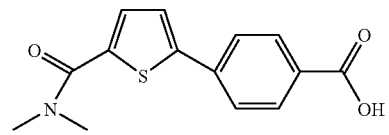

The title intermediate is prepared in a manner substantially analogous General Procedure C in 6 mL 20% aqueous dioxane using a mixture of the 4-(5-dimethylcarbamoyl-thiophen-2-yl)-benzoic acid methyl ester (130 mg, 0.45 mmol) and lithium hydroxide monohydrate (23 mg, 1.2 mmol). The lithium salt is converted to the free carboxylic acid to give the title intermediate (100 mg, 80% yield). MS (ES+) 276.2 (M+H)$^+$ Intermediate Preparation 4

4-(5-Isobutyryl-thiophen-2-yl)-benzoic acid methyl ester

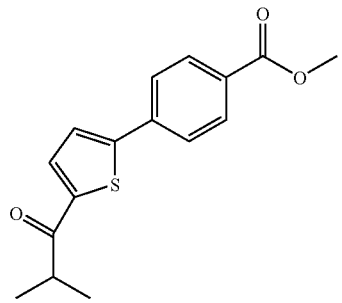

The title intermediate is prepared in a manner substantially analogous General Procedure B in 4 mL dioxane using a mixture of the 1-(5-Bromo-thiophen-2-yl)-2-methyl-propan-1-one (CAS 32412-45-6) (124 mg, 0.53 mmol), 4-methoxycarbonylphenyl boronic acid (115, 0.64 mmol), tetrakis(triphenylphosphine)palladium (0) (30 mg, 0.03 mmol), and 2M Na$_2$CO$_3$ (0.6 mL, 1.20 mmol) in three consecutive 30 minute microwave sessions to give the desired intermediate. (110 mg, 72% yield) MS (ES+) 289.2 (M+H)$^+$ Intermediate Preparation 5

4-(5-Isobutyryl-thiophen-2-yl)-benzoic acid, Lithium salt

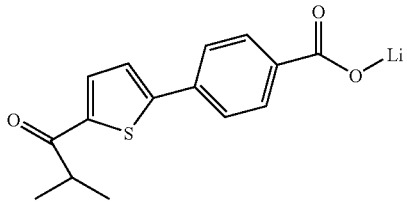

The title intermediate is prepared in a manner substantially analogous General Procedure C in 3 mL 20% aqueous dioxane using a mixture of the 4-(5-Isobutyryl-thiophen-2-yl)-benzoic acid methyl ester (101 mg, 0.35 mmol) and lithium hydroxide monohydrate (17 mg, 0.41 mmol) to give the lithium salt (98 mg, 100% yield). MS (ES+) 275.3 (M+H)$^+$ Intermediate Preparation 6

4-(5-Sulfamoyl-thiophen-2-yl)-benzoic acid, lithium salt

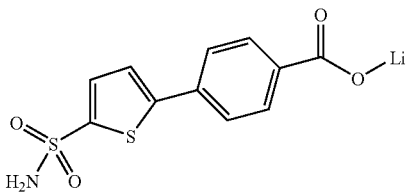

The title intermediate is prepared in a manner substantially analogous General Procedure A, followed by General Procedure C using of the 5-Bromo-thiophene-2-sulfonic acid amide (CAS 53595-65-6) and 4-methoxycarbonylphenyl boronic acid to give the desired intermediate. (180 mg) MS (ES−) 282.0 (M−H)$^−$ Intermediate Preparation 7

4-(5-Oxazol-5-yl-thiophen-2-yl)-benzoic acid

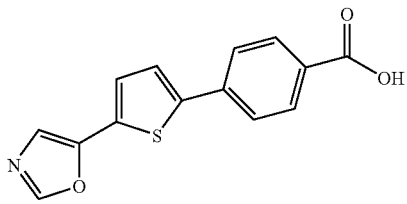

The title intermediate is prepared in a manner substantially analogous General Procedure B, followed by General Procedure C using 5-(5-Bromo-thiophen-2-yl)-oxazole (CAS 321309-25-5) and 4-methoxycarbonylphenyl boronic acid to give the desired intermediate. (140 mg) MS (ES−) 270.0 (M−H)$^−$ Intermediate Preparation 8

4-(5-Methylsulfanyl-thiophen-2-yl)-benzoic acid, Lithium salt

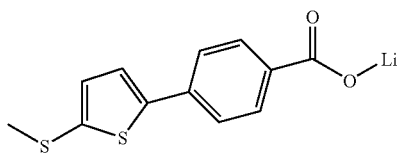

Procedure F: A 5 mL THF solution of 4-thiophen-2-yl-benzoic acid methyl ester (CAS 17595-86-7) (109 mg, 0.5 mmol) is stirred under N$_2$ at −70° C. while 1.5 M lithium diisopropylamide in cyclohexane (0.38 mL, 0.6 mmol) is added and reaction temperature allowed to warm to −30° C. Reaction is cooled back down to −70° C. and stirred 1 hour. Methyl disulfide (0.3 mL, 6.6 mmol) is added, stirred 20 minutes, and then allowed to warm to 10-15° C. The reaction is cooled to 0° C., diluted with EtOAc and quenched with aq. NaHCO₃. The organic layer is separated, washed with brine, dried (Na₂SO₄) and concentrated in vacuo. The crude mixture is purified by silica-gel column chromatography (gradient: 0-25% EtOAc/hexane) to give the desired methyl ester. The lithium salt is prepared in a manner substantially analogous to General Procedure D. (51 mg) MS (ES−) 249.10 (M−H)⁻

Intermediate Preparation 9

4-(5-Methanesulfonyl-thiophen-2-yl)-benzoic acid, Lithium salt

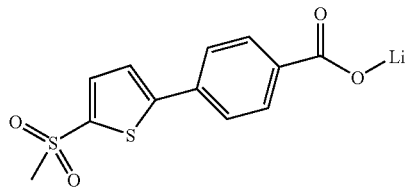

A 10 mL dichloromethane solution of 4-(5-methanesulfonyl-thiophen-2-yl)-benzoic acid methyl ester (103 mg, 0.39 mmol) is stirred while 50-55% m-chloroperoxybenzoic acid (1000 mg, 2.9 mmol) is added portionwise. After 18 hours, the reaction is diluted with EtOAc washed with aq. NaHCO₃, 1 N NaOH, brine, dried (Na₂SO₄) and concentrated in vacuo to give the sulfone. The lithium salt is prepared in a manner substantially analogous to General Procedure D. (94 mg).

MS (ES−) 281.0 (M−H)⁻

Intermediate Preparation 10

4-[5-(Pyrrolidine-1-carbonyl)-thiophen-2-yl]-benzoic acid

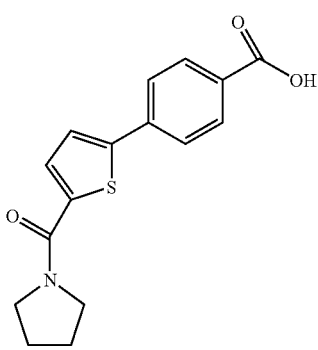

The title intermediate is prepared in a manner substantially analogous General Procedure B, followed by General Procedure C using (5-Bromo-thiophen-2-yl)-pyrrolidin-1-yl-methanone (CAS 326875-64-3) and 4-methoxycarbonylphenyl boronic acid to give the desired intermediate. (125 mg) MS (ES−) 300.0 (M−H)⁻

Intermediate Preparation 11

4-(2-Cyano-thiophen-3-yl)-benzoic acid, lithium salt

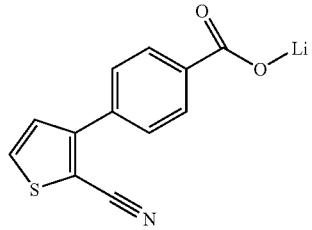

The title intermediate is prepared in a manner substantially analogous General Procedure A, followed by General Procedure C using 3-bromo-thiophene-2-carbonitrile and 4-methoxycarbonylphenyl boronic acid to give the desired intermediate. (390 mg) MS (ES−) 228.2 (M−H)⁻

Intermediate Preparation 12

4-(5-Ethanesulfonyl-thiophen-2-yl)-benzoic acid, lithium salt

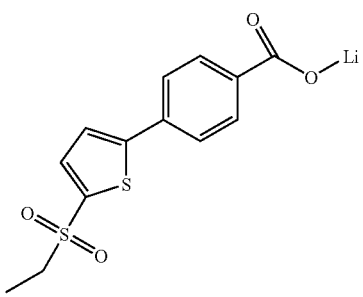

The title intermediate is prepared in a manner substantially analogous to Procedure F using 4-thiophen-2-yl-benzoic acid methyl ester and ethyldisulfide, followed by Procedure O to give the ethyl sulfone, and then General Procedure C to give the lithium salt (118 mg). MS (ES−) 295.0 (M−H)⁻

Intermediate Preparation 13

4-(5-Cyano-thiophen-2-yl)-2-fluoro-benzoic acid

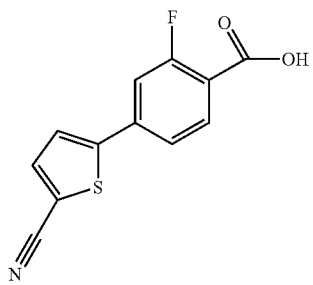

The title intermediate is prepared in a manner substantially analogous General Procedure A using 5-bromo-thiophene-2- carbonitrile and 4-carboxy-3-fluorophenyl boronic acid to give the desired intermediate. (440 mg) MS (ES−) 246.0 (M−H)⁻

Intermediate Preparation 14

4-(5-Carbamoyl-thiophen-3-yl)-benzoic acid

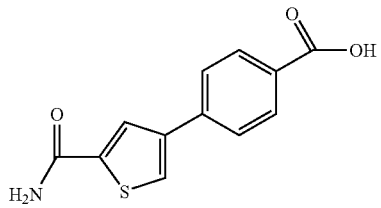

The title intermediate is prepared in a manner substantially analogous General Procedure A using 4-Bromo-thiophene-2-carbonitrile (CAS 18791-99-6) and 4-methoxycarbonylphenyl boronic acid, followed by General Procedure C that converts the nitrile to the primary amide as well as the ester to the acid to give the intermediate as a mixture. (360 mg) MS (ES−) 246.0 (M−H)⁻

Intermediate Preparation 15

6-Thiophen-3-yl-nicotinic acid

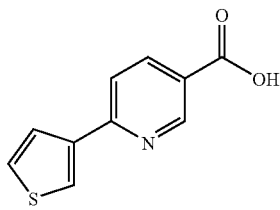

Procedure V: 6-Thiophen-3-yl-pyridine-3-carbaldehyde (0.475 g, 2.5 mmol) is suspended in formic acid (3.5 mL), and the solution is placed in an ice bath. Hydrogen peroxide is added (0.875 mL, 7.5 mmol), and the reaction vessel is placed in the refrigerator and is allowed to stand for 1 day. On addition of water, a white solid is precipitated, which is filtered, washed with cold water and dried in a vacuum oven to give the desired product (0.35 g, 68%). MS (ES−) 204.1.

Intermediate Preparation 16

[2-(S)-(2-(R)-Methyl-pyrrolidin-1-ylmethyl)-pyrrolidin-1-yl]-[4-(4,4,5,5-tetramethyl-[1,3,2]dioxaborolan-2-yl)-phenyl]-methanone

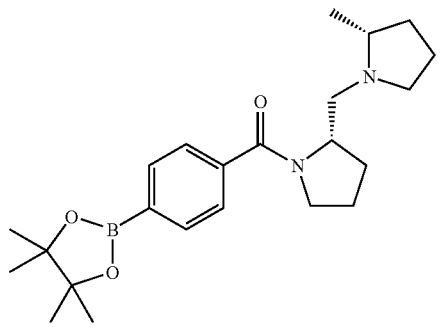

The title intermediate is prepared in a manner substantially analogous General Procedure E using 2-(R)-methyl-1-(2-(S)-pyrrolidinylmethyl)pyrrolidine and 4-(4,4,5,5-tetramethyl-[1,3,2]dioxaborolan-2-yl)-benzoic acid (CAS 180516-87-4). The crude product is confirmed by NMR and used without further purification.

Intermediate Preparation 17

4-Thiazol-4-yl-benzoic acid methyl ester

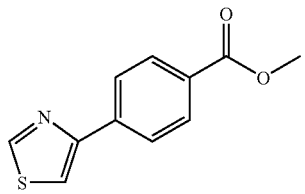

Procedure M: A suspension of 4-bromothiazole (1.13 g, 6.89 mmol), 4-methoxycarbonylphenylboronic acid (1.85 g, 10.3 mmol) and Tetrakis (triphenylphosphine) palladium (0) (0.35 g, 0.30 mmol) in dioxane (45 mL) and 2M $Na_2CO_3$ (17.2 mL) is heated to reflux for 18 h. The reaction is allowed to cool and filtered. The filtrate is evaporated in vacuo, and the residue is dissolved in ethyl acetate and washed with water (2×) and brine (2×). The combined organic layers are dried over $Na_2SO_4$, and concentrated in vacuo. The crude material is purified by flash chromatography (100% hexanes-40% ethyl acetate/hexanes) to give 4-thiazol-4-yl-benzoic acid methyl ester as a white solid (0.68 g, 45%) MS (ES+) 220.2

Intermediate Preparation 18

4-Thiazol-4-yl-benzoic acid, lithium salt

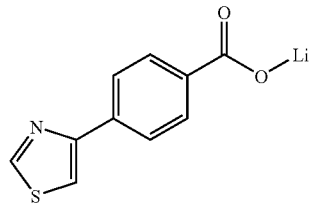

Procedure N: 4-Thiazol-4-yl-benzoic acid methyl ester (0.68 g, 3.11 mmol) is dissolved in dioxane (30 mL) and lithium hydroxide monohydrate (0.14 g, 3.43 mmol), followed by water (10 mL) is added. The reaction is sonicated to dissolve the lithium hydroxide, and the reaction mixture is stirred at room temperature overnight. The solvent is removed in vacuo to give the title compound, which is used without further purification (0.66, 100%). MS (ES−) 204.2

Intermediate Preparation 19

4-(2-Methylsulfanyl-thiazol-4-yl)-benzoic acid methyl ester

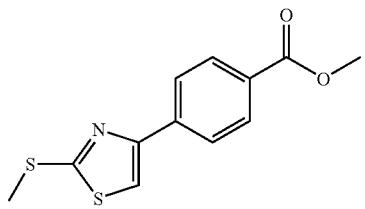

The title compound is prepared in a manner substantially analogous to Procedure M starting from 4-Bromo-2-methylsulfanyl-thiazole (CAS 204513-62-2) and 4-methoxycarbonylphenylboronic acid. MS (ES+) 266.2.

Intermediate Preparation 20

4-(2-Methanesulfonyl-thiazol-4-yl)-benzoic acid methyl ester

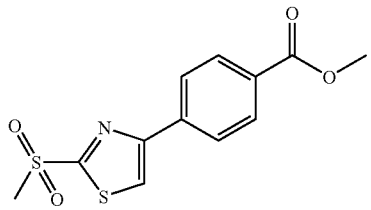

Procedure O: A solution of 4-(2-Methylsulfanyl-thiazol-4-yl)-benzoic acid methyl ester (0.68 g, 3.77 mmol) in MeOH (5 mL), THF (10 mL), and water (5 mL) at 0° C. is treated with solid oxone (potassium mono persulfate, 6.95 g, 11.30 mmol) in one portion. The ice cold bath is removed, the reaction allowed to warm to room temperature and stirred for 3 hours. Water and ethyl acetate are added, the layers separated and the aqueous layer extracted with ethyl acetate (2×. The combined organic layers are washed with brine, dried over $Na_2SO_4$, and concentrated to give a white solid. The crude solid was triturated with ether, and filtered to give the title compound (0.67 g, 88%). MS (ES+) 298.3.

Intermediate Preparation 21

4-(4-Pyridin-3-yl-thiazol-2-yl)-benzoic acid ethyl ester

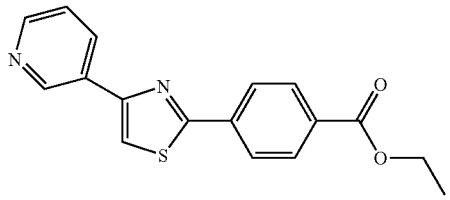

4-Thiocarbamoyl-benzoic acid ethyl ester (CAS 78950-31-9) (0.4 g, 1.91 mmol), and 2-Bromo-1-pyridin-3-yl-ethanone; hydrobromide (CAS 17694-68-7) (0.537 g, 1.91 mmol) is placed in a 100 mL flask and dissolved in 20 mL of isopropyl alcohol. The mixture is heated to reflux for 1.5 hours and cooled and diluted with 40 mL of diethyl ether. The resulting solid is filtered and dissolved in a mixture of dichloromethane and saturated sodium bicarbonate solution. The organics are separated, dried over sodium sulfate, filtered and concentrated to provide 0.565 g of the titled compound. MS (m/e) 311.1 (M+1)

Intermediate Preparation 22

Sodium-4-(4-Pyridin-3-yl-thiazol-2-yl)-benzoic acid

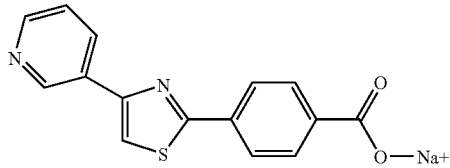

4-(4-Pyridin-3-yl-thiazol-2-yl)-benzoic acid ethyl ester (0.560 g, 1.8 mmol) is placed in a 100 mL flask and dissolved in a mixture of 5 mL tetrahydrofuran and 5 mL of ethanol. 2N NaOH (0.95 mL, 1.89 mmol) is added and the mixture is heated to reflux for 4 hours. The reaction is concentrated to dryness to give 528 mg of the titled compound. MS (m/e) 281 (M−1), 283 (M+1).

Intermediate Preparation 23

4-[4-(1-Amino-1-methyl-ethyl)-thiazol-2-yl]-benzoic acid ethyl ester:hydrobromide

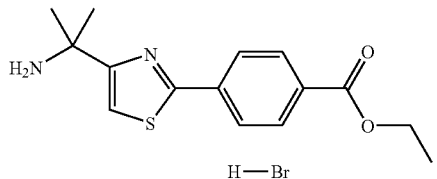

4-Thiocarbamoyl-benzoic acid ethyl ester (0.802 g, 3.83 mmol), and 1-bromo-3-tert-butylamino-3-methyl-butane-2-one; hydrobromide (1.0 g, 3.83 mmol) [which can be prepared by the method of W. Hargrove, U.S. Pat. No. 3,494,964] is placed in a 100 mL flask and dissolved in 30 mL of isopropyl alcohol. The mixture is heated to reflux for 1.5 hours and cooled and diluted with 60 mL of diethyl ether. The resulting solid is filtered and dried to give 1.23 g of the titled compound. MS (m/e) 291.1 (M+1)

Intermediate Preparation 24

4-[4-(1-Acetylamino-1-methyl-ethyl)-thiazol-2-yl]-benzoic acid ethyl ester

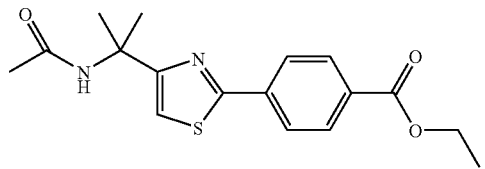

4-[4-(1-Amino-1-methyl-ethyl)-thiazol-2-yl]-benzoic acid ethyl ester:hydrobromide (0.208 g, 0.56 mmol) is placed in a 50 mL flask and dissolved in 5 mL dichloromethane. Pyridine (4.48 mmol, 0.362 mL), and acetyl chloride (1.79 mmol, 0.128 mL) are added and stirred for 20 minutes. The reaction is diluted with ethyl acetate and washed successively with 0.1N HCl and sodium bicarbonate solution. The organics are separated and dried over sodium sulfate, filtered, and concentrated to provide the titled compound as an oil. MS (m/e) 333.2 (M+1)

Intermediate Preparation 25

4-[4-(1-Acetylamino-1-methyl-ethyl)-thiazol-2-yl]-benzoic acid

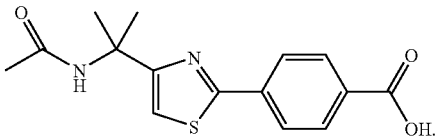

4-[4-(1-Acetylamino-1-methyl-ethyl)-thiazol-2-yl]-benzoic acid ethyl ester (0.13 g, 0.39 mmol) is dissolved in 2 mL tetrahydrofuran and 2 mL ethanol. 2N sodium hydroxide (1.17 mmol, 0.587 mL) is added and the mixture is heated to reflux for 1 hour. The reaction is concentrated to dryness and the resulting residue is dissolved in 95:5 dichloromethane/isopropanol layered with 0.1N HCl. The organics are separated and dried over sodium sulfate, filtered, and concentrated to give 0.106 g of the pure titled compound. MS (m/e) 303.2 (M−H)⁻

Intermediate Preparation 26

4-[4-(1-Benzoylamino-1-methyl-ethyl)-thiazol-2-yl]-benzoic acid ethyl ester

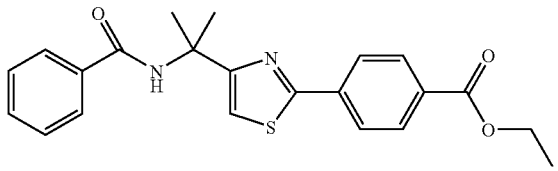

To a stirring solution of 4-[4-(1-Amino-1-methyl-ethyl)-thiazol-2-yl]-benzoic acid ethyl ester:hydrobromide (11.0 mmol) and n-methylmorpholine (2.0 mmol) in dichloromethane (0.10M), add benzoyl chloride (1.0 mmol) diluted in 2 mL dichloromethane. Stir at room temperature for 20 minutes. Wash the reaction with water while extracting with dichloromethane. Dry the organic layer with sodium sulfate, filter and concentrate in vacuo. Purify via radial chromatography eluting with ethyl acetate and hexane. MS (m/e): 395.2 (M+H)⁺

Intermediate Preparation 27

Sodium-4-[4-(1-Benzoylamino-1-methyl-ethyl)-thiazol-2-yl]-benzoic acid

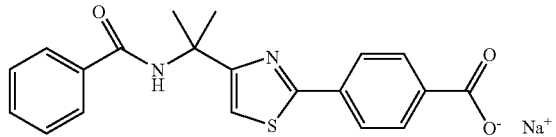

The titled compound is prepared substantially in accordance with the procedure of Intermediate Preparation 2 using the titled compound from 4-[4-(1-Benzoylamino-1-methyl-ethyl)-thiazol-2-yl]-benzoic acid ethyl ester.

MS (me): 367.2 (M+1), 365.2 (M−H)⁻

Intermediate Preparation 28

4-(5-Chloro-1H-benzoimidazol-2-yl)-benzoyl chloride

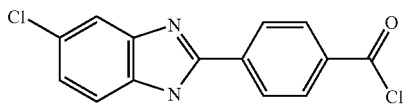

To a stirring solution of 4-(5-chloro-1H-benzoimidazol-2-yl)-benzoic acid (1.0 mmol) (CAS 204514-08-9) and oxalyl chloride (2.0 mmol) in dichloromethane (0.10M), add 2 drops of dimethylformamide as a catalyst. Stir at room temperature for 2 hours. After this time, concentrate the reaction in vacuo. Assume total conversion to the acid chloride.

Intermediate Preparation 29

[2-Fluoro-4-(4,4,5,5-tetramethyl-[1,3,2]dioxaborolan-2-yl)-phenyl]-[2-(S)-(2-(R)-methyl-1-pyrrolidin-1-ylmethyl)-pyrrolidin-1-yl]-methanone

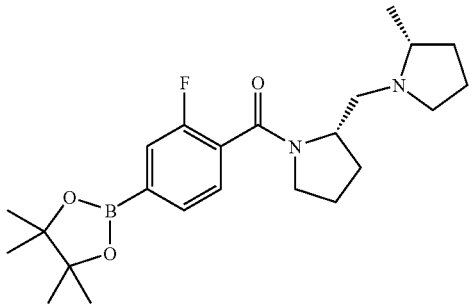

A 100 mL toluene/EtOH mixture of commercially available 4-carboxy-3-phenyl boronic acid and pinacol is stirred at 75-80° C. for 2 hours, then concentrated, slurried in toluene, concentrated, and dried in vacuo to give 2-Fluoro-4-(4,4,5,5-tetramethyl-[1,3,2]dioxaborolan-2-yl)-benzoic acid that is used without further purification. The title intermediate is prepared in a manner substantially analogous. General Procedure E using 2-(R)-methyl-1-(2-(S)-pyrrolidinylmethyl) pyrrolidine and 2-Fluoro-4-(4,4,5,5-tetramethyl-[1,3,2]dioxaborolan-2-yl)-benzoic acid. The crude product is confirmed by NMR and MS (MS+) 417.5 (M+H)⁺ then used without further purification.

Intermediate Preparation 30

Azetidin-1-yl-(5-bromo-thiophen-2-yl)-methanone

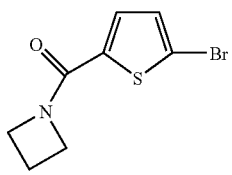

The title intermediate is prepared in a manner substantially analogous General Procedure E using 5-bromo-thiophene-2-carboxylic acid (CAS 7311-63-9) and azetidine to give the crude intermediate. This material is then purified by silica-gel column chromatography (gradient: 0-20% EtOAc/CH₂Cl₂) to give clean product. The product is confirmed by NMR.

Intermediate Preparation 31

(2-Bromo-thiazol-5-yl)-pyrrolidin-1-yl-methanone

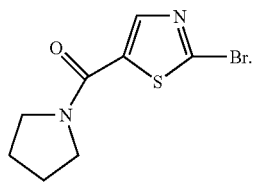

The title intermediate is prepared in a manner substantially analogous General Procedure D using 2-Bromo-thiazole-5- carboxylic acid (CAS 54045-76-0) and pyrrolidine to give the crude intermediate. This material is then purified by silica-gel column chromatography (gradient: 0-20% EtOAc/CH$_2$Cl$_2$) to give clean product. The product is confirmed by NMR.

Intermediate Preparation 32

2-Bromo-5-ethanesulfonyl-thiophene

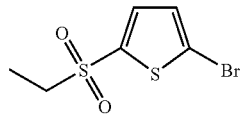

A 25 mL THF/MeOH (2:1) solution of 2-Bromo-5-ethylsulfanyl-thiophene (CAS 19991-60-7) is stirred at 0-10° C. while 8 mL H$_2$O, then 3 equivalents of Oxone are added. The reaction mixture is stirred three hours at room temperature, then is diluted with CH$_2$Cl$_2$, filtered, washed with aq. NaHCO$_3$ and brine, dried (Na$_2$SO$_4$) and concentrated in vacuo. The crude mixture is purified by silica gel column chromatography (gradient: 0-20% EtOAc/CH$_2$Cl$_2$) to give title intermediate that is confirmed by NMR.

Intermediate Preparation 33

2-Bromo-thiazole-5-carbaldehyde O-methyl-oxime

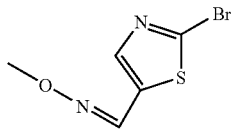

Methoxylamine HCl (1 equivalent) is added portionwise to a stirred pyridine (1 equivalent) solution of 5-bromo-2-thiophene carboxaldehyde (1 equivalent) (CAS 4701-17-1). After 18 hours, reaction is diluted with CH$_2$Cl$_2$ and washed with brine, dried (Na$_2$SO$_4$) and concentrated in vacuo. The crude mixture is purified by silica gel column chromatography (gradient: 0-20% EtOAc/hexanes) to give title intermediate that is confirmed by NMR.

Example 1

5-[4-(2(S)-Pyrrolidin-1-ylmethyl-pyrrolidine-1-carbonyl)-phenyl]-thiophene-2-carbonitrile

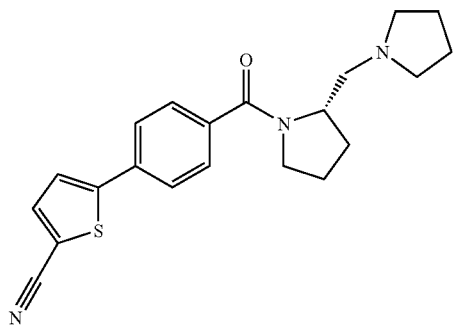

The title compound is prepared in a manner substantially analogous to General Procedure D in 100 mL 10% DMF/dichloromethane using 4-(5-cyano-thiophen-2-yl)-benzoic acid (CAS 402765-55-9) (2.75 g, 12.0 mmol), EDC-HCl (3.44 g, 18.0 mmol), HOBt (2.43 g, 18.0 mmol), DIEA (5.22 mL, 30 mmol) and (S)(+)-1-(2-pyrrolidinylmethyl)pyrrolidine (1.54 g, 10.0 mmol) to give the title compound (2.33 g, 64% yield). MS (ES+) 366.2 (M+H)$^+$ Example 2

5-{4-[2-(2(S)-(2-(R)-methyl-pyrrolidin-1-ylmethyl)-pyrrolidine-1-carbonyl]-phenyl}-thiophene-2-carbonitrile

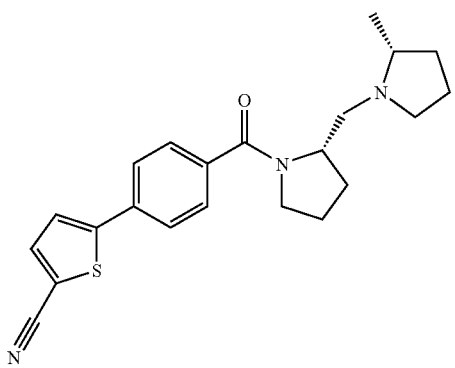

The title compound is prepared in a manner substantially analogous to General Procedure D in 10 mL 10% DMF/dichloromethane using 4-(5-cyano-thiophen-2-yl)-benzoic acid (CAS 402765-55-9) (360 mg, 1.57 mmol), EDC-HCl (451 mg, 2.36 mmol), HOBt (319 mg, 2.36 mmol), DIEA (1.14 mL, 6.5 mmol) and 2-(R)-Methyl-1-(2-(S)-pyrrolidinylmethyl)pyrrolidine di HCl (314 mg, 1.31 mmol) to give the title compound (60 mg, 13% yield). MS (ES+) 380.3 (M+H)$^+$ Example 3

5-[4-(2(S)-Pyrrolidin-1-ylmethyl-pyrrolidine-1-carbonyl)-phenyl]-thiophene-Z-carboxylic acid amide

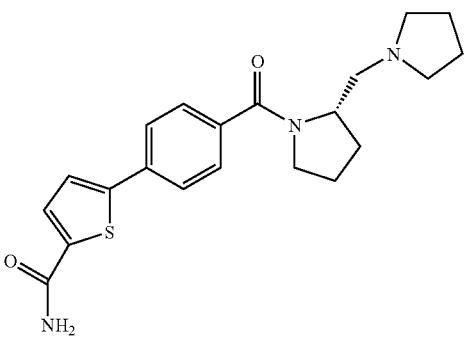

A 1.5 mL DMSO solution of 5-[4-(2(S)-pyrrolidin-1-ylmethyl-pyrrolidine-1-carbonyl)-phenyl]-thiophene-2-carbonitrile (102 mg, 0.28 mmol) is stirred at room temperature while K$_2$CO$_3$ (55 mg, 0.4 mmol) and 0.2 mL H$_2$O is added, then 30% H$_2$O$_2$ (40 mg, 0.33 mmol) and is stirred one hour. The reaction mixture is diluted with MeOH and put on an SCX column ((MeOH wash, then elution with 2M NH$_3$/MeOH) and concentrated to give partially purified material. This material is then purified by silica-gel column chromatography (gradient: 0-4% (2M NH$_3$/MeOH) in CH$_2$Cl$_2$ to give the title compound (60 mg, 56%). MS (ES+) 384.2.

Example 4

(2(S)-Pyrrolidin-1-ylmethyl-pyrrolidin-1-yl)-(4-thiophen-2-yl-phenyl)-methanone

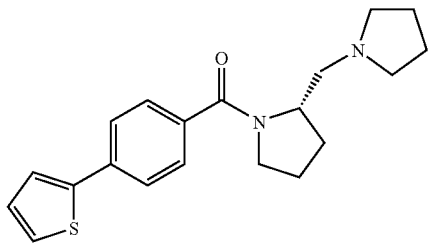

The title compound is prepared in a manner substantially analogous to General Procedure D in 10 mL 10% DMF/dichloromethane using 4-(thiophen-2-yl)-benzoic acid (CAS 29886-62-2) (182 mg, 0.89 mmol), EDC-HCl (254 mg, 1.33 mmol), HOBt (180 mg, 1.33 mmol), DIEA (0.39 mL, 2.22 mmol) and (S)(+)-1-(2-pyrrolidinylmethyl)pyrrolidine (116 mg, 10.0 mmol) to give the title compound (90 mg, 35% yield). MS (ES+) 341.2 (M+H)$^+$

Example 5

5-[4-(2(S)-Pyrrolidin-1-ylmethyl-pyrrolidine-1-carbonyl)-phenyl]-thiophene-2-carboxylic acid dimethylamide

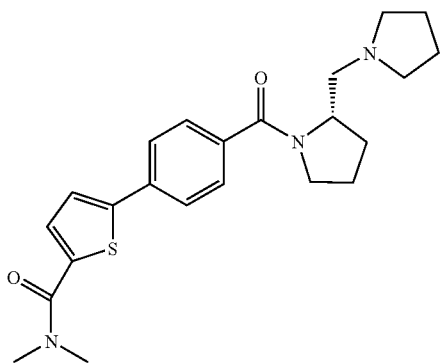

The title compound is prepared in a manner substantially analogous to General Procedure D in 10 mL 10% DMF/dichloromethane using 4-(5-dimethylcarbamoyl-thiophen-2-yl)-benzoic acid (88 mg, 0.32 mmol), EDC-HCl (86 mg, 0.45 mmol), HOBt (61 mg, 0.45 mmol), DIEA (0.14 mL, 0.80 mmol) and (S)(+)-1-(2-pyrrolidinylmethyl)pyrrolidine (46 mg, 0.30 mmol) to give the title compound (100 mg, 81% yield). MS (ES+) 412.3 (M+H)$^+$

Example 6

2-Methyl-1-{5-[4-(2(S)-pyrrolidin-1-ylmethyl-pyrrolidine-1-carbonyl)-phenyl]-thiophen-2-yl}-propan-1-one

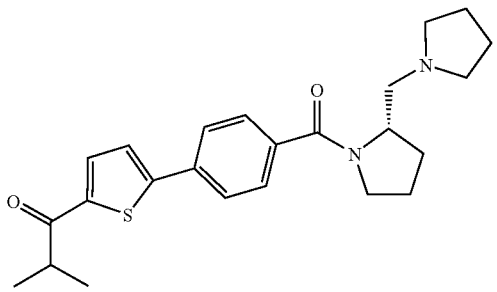

The title compound is prepared in a manner substantially analogous to General Procedure D in 10 mL 50% DMF/dichloromethane using 4-(5-isobutyryl-thiophen-2-yl)-benzoic acid, lithium salt (96 mg, 0.34 mmol), EDC-HCl (97 mg, 0.51 mmol), HOBt (69 mg, 0.51 mmol), DIEA (0.09 mL, 0.51 mmol) and (S)(+)-1-(2-pyrrolidinylmethyl)pyrrolidine (48 mg, 0.31 mmol) to give the title compound (90 mg, 71% yield). MS (ES+) 411.2 (M+H)$^+$

Example 7

5-[4-(2(S)-Pyrrolidin-1-ylmethyl-pyrrolidine-1-carbonyl)-phenyl]-thiophene-2-sulfonic acid amide

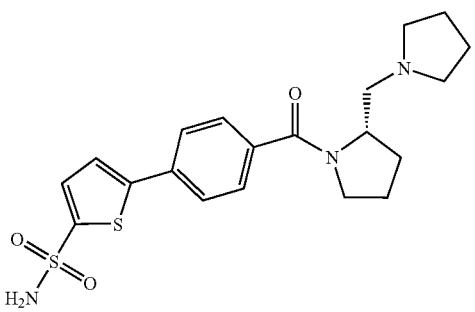

The title compound is prepared in a manner substantially analogous to General Procedure D in 9 mL 50% DMF/dichloromethane using 4-(5-Sulfamoyl-thiophen-2-yl)-benzoic acid, lithium salt (173 mg, 0.61 mmol), EDC-HCl (174 mg, 0.91 mmol), HOBt (123 mg, 0.91 mmol), DIEA (0.26 mL, 1.5 mmol) and (S)(+)-1-(2-pyrrolidinylmethyl)pyrrolidine (79 mg, 0.51 mmol) to give the title compound (74 mg, 34% yield). MS (ES+) 420.2 (M+H)$^+$

Example 8

[4-(5-Oxazol-5-yl-thiophen-2-yl)-phenyl]-(2(S)-pyrrolidin-1-ylmethyl-pyrrolidin-1-yl)-methanone

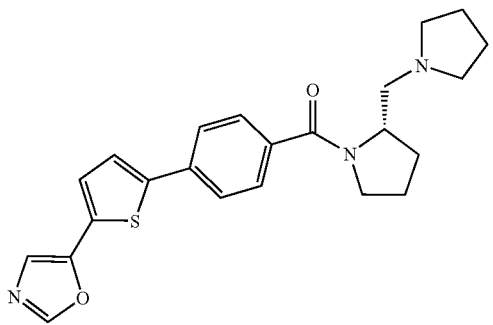

The title compound is prepared in a manner substantially analogous to General Procedure D in 9 mL 50% DMF/dichloromethane using 4-(5-oxazol-5-yl-thiophen-2-yl)-benzoic acid (133 mg, 0.49 mmol), EDC-HCl (143 mg, 0.75 mmol), HOBt (101 mg, 0.75 mmol), DIEA (0.22 mL, 1.5 mmol) and (S)(+)-1-(2-pyrrolidinylmethyl)pyrrolidine (63 mg, 0.41 mmol) to give the title compound (80 mg, 48% yield). MS (ES+) 408.3 (M+H)$^+$

Example 9
[4-(5-Methylsulfanyl-thiophen-2-yl)-phenyl]-(2(S)-pyrrolidin-1-ylmethyl-pyrrolidin-1-yl)-methanone

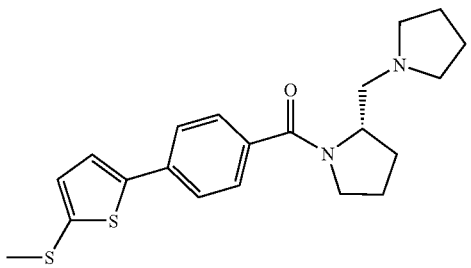

The title compound is prepared in a manner substantially analogous to General Procedure D in 8 mL 37% DMF/dichloromethane using 4-(5-methylsulfanyl-thiophen-2-yl)-benzoic acid, Lithium salt (51 mg, 0.20 mmol), EDC-HCl (57 mg, 0.30 mmol), HOBt (41 mg, 0.30 mmol), DIEA (0.09 mL, 0.5 mmol) and (S)(+)-1-(2-pyrrolidinylmethyl)pyrrolidine (28 mg, 0.18 mmol) to give the title compound (50 mg, 71% yield). MS (ES+) 387.7 (M+H)+

Example 10
[4-(5-Methanesulfonyl-thiophen-2-yl)-phenyl]-(2(S)-pyrrolidin-1-ylmethyl-pyrrolidin-1-yl)-methanone

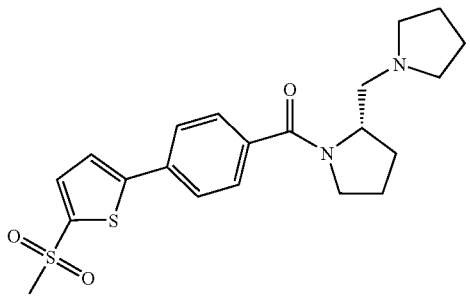

The title compound is prepared in a manner substantially analogous to General Procedure D in 8 mL 37% DMF/dichloromethane using 4-(5-methanesulfonyl-thiophen-2-yl)-benzoic acid, Lithium salt (92 mg, 0.32 mmol), EDC-HCl (92 mg, 0.48 mmol), HOBt (65 mg, 0.48 mmol), DIEA (0.14 mL, 0.8 mmol) and (S)(+)-1-(2-pyrrolidinylmethyl)pyrrolidine (45 mg, 0.29 mmol) to give the title compound (60 mg, 57% yield). MS (ES+) 419.2 (M+H)+

Example 11
{4-[5-(Pyrrolidine-1-carbonyl)-thiophen-2-yl]-phenyl}-(2(S)-pyrrolidin-1-ylmethyl-pyrrolidin-1-yl)-methanone

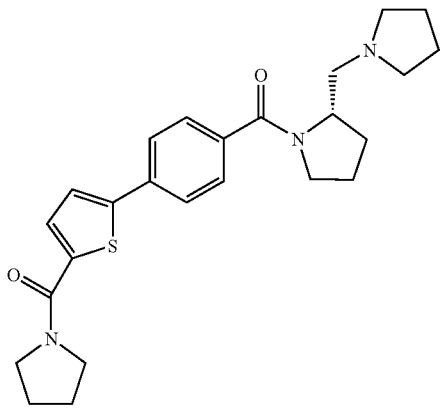

The title compound is prepared in a manner substantially analogous to General Procedure D in 5 mL 20% DMF/dichloromethane using 4-[5-(Pyrrolidine-1-carbonyl)-thiophen-2-yl]-benzoic acid (121 mg, 0.40 mmol), EDC-HCl (115 mg, 0.60 mmol), HOBt (81 mg, 0.60 mmol), DIEA (0.17 mL, 1.0 mmol) and (S)(+)-1-(2-pyrrolidinylmethyl)pyrrolidine (52 mg, 0.34 mmol) to give the title compound (85 mg, 57% yield). MS (ES+) 438.3 (M+H)+

Example 12
3-[4-(2(S)-Pyrrolidin-1-ylmethyl-pyrrolidine-1-carbonyl)-phenyl]-thiophene-2-carbonitrile

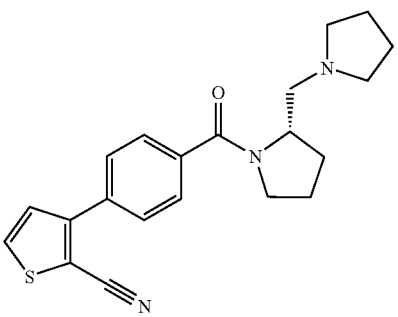

The title compound is prepared in a manner substantially analogous to General Procedure D in 5 mL 20% DMF/dichloromethane using 4-(2-cyano-thiophen-3-yl)-benzoic acid, lithium salt (141 mg, 0.60 mmol), EDC-HCl (143 mg, 0.75 mmol), HOBt (101 mg, 0.75 mmol), DIEA (0.24 mL, 1.4 mmol) and (S)(+)-1-(2-pyrrolidinylmethyl)pyrrolidine (77 mg, 0.50 mmol) to give the title compound (120 mg, 66% yield). MS (ES+) 366.3 (M+H)+

Example 13
[4-(5-Methanesulfonyl-thiophen-2-yl)-phenyl]-[2-(S)-(2-(R)-methyl-pyrrolidin-1-ylmethyl)-pyrrolidin-1-yl]-methanone, HCl salt

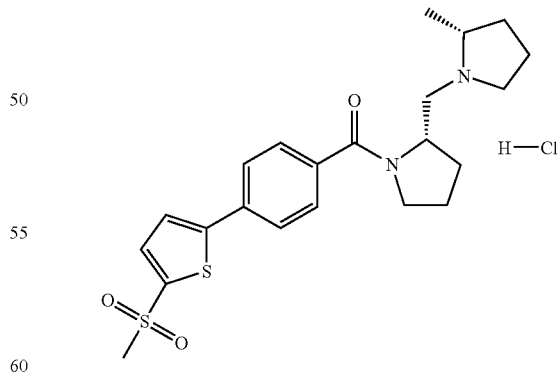

The title compound is prepared in a manner substantially analogous to General Procedure D in 5 mL 50% DMF/dichloromethane using 4-(5-methanesulfonyl-thiophen-2-yl)-benzoic acid, Lithium salt (119 mg, 0.42 mmol), EDC-HCl (115 mg, 0.60 mmol), HOBt (81 mg, 0.60 mmol), DIEA (0.19 mL, 1.1 mmol) and 2-(R)-Methyl-1-(2-(S)-pyrrolidinylmethyl)

pyrrolidine (64 mg, 0.38 mmol) to give the title compound isolated as the HCl salt (65 mg, 40% yield). MS (ES+) 433.3 (free base) (M+H)+

Example 14

[4-(5-Ethanesulfonyl-thiophen-2-yl)-phenyl]-[2-(S)-(2-(R)-methyl-pyrrolidin-1-ylmethyl)-pyrrolidin-1-yl]-methanone

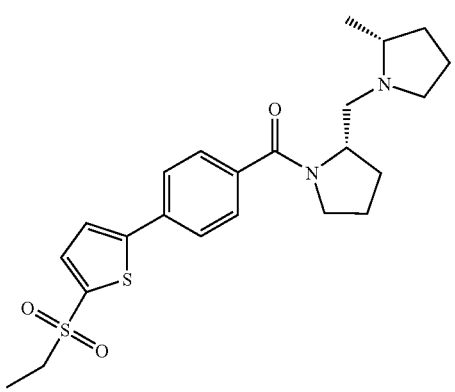

The title compound is prepared in a manner substantially analogous to General Procedure D in 5 mL 50% DMF/dichloromethane using 4-(5-ethanesulfonyl-thiophen-2-yl)-benzoic acid, Lithium salt (118 mg, 0.39 mmol), EDC-HCl (115 mg, 0.60 mmol), HOBt (81 mg, 0.60 mmol), DIEA (0.17 mL, 1.0 mmol) and 2-(R)-Methyl-1-(2-(S)-pyrrolidinylmethyl)pyrrolidine (61 mg, 0.36 mmol) to give the title compound (80 mg, 50% yield). MS (ES+) 447.3 (M+H)+

Example 15

5-[3-Fluoro-4-(2-pyrrolidin-1-ylmethyl-pyrrolidine-1-carbonyl)-phenyl]-thiophene-2-carbonitrile

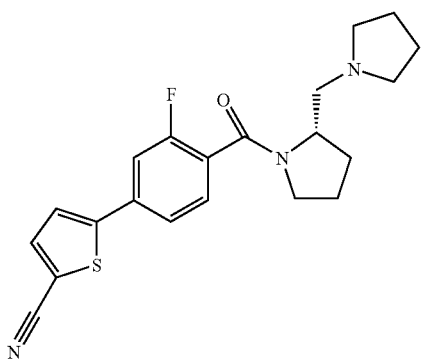

The title compound is prepared in a manner substantially analogous to General Procedure D in 6 mL DMF using 4-(5-Cyano-thiophen-2-yl)-2-fluoro-benzoic acid (248 mg, 1.0 mmol), EDC-HCl (287 mg, 1.5 mmol), HOBt (203 mg, 1.5 mmol), DIEA (0.43 mL, 2.5 mmol) and (S)(+)-1-(2-pyrrolidinylmethyl)pyrrolidine (131 mg, 0.85 mmol) to give the title compound (30 mg, 10% yield). MS (ES+) 384.2 (M+H)+

Example 16

5-{3-Fluoro-4-[2-(S)-(2-(R)-methyl-pyrrolidin-1-ylmethyl)-pyrrolidine-1-carbonyl]-phenyl}-thiophene-2-carbonitrile

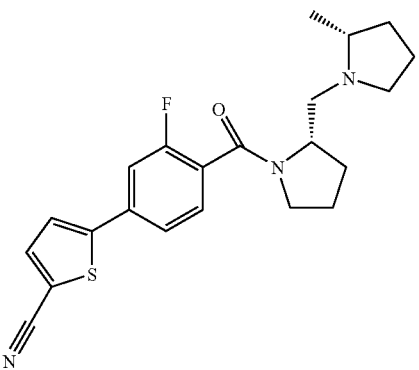

The title compound is prepared in a manner substantially analogous to General Procedure D in 6 mL DMF using 4-(5-cyano-thiophen-2-yl)-2-fluoro-benzoic acid (181 mg, 0.73 mmol), EDC-HCl (210 mg, 1.1 mmol), HOBt (149 mg, 1.1 mmol), DIEA (0.31 mL, 1.8 mmol) and 2-(R)-Methyl-1-(2-(S)-pyrrolidinylmethyl)pyrrolidine (101 mg, 0.60 mmol) to give the title compound (30 mg, 12% yield). MS (ES+) 398.3 (M+H)+

Example 17

4-{4-[2-(S)-(2-(R)-Methyl-pyrrolidin-1-ylmethyl)-pyrrolidine-1-carbonyl]-phenyl}-thiophene-2-carboxylic acid amide

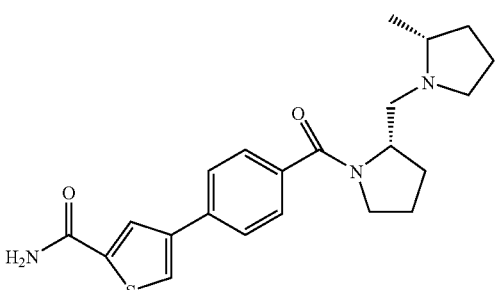

The title compound is prepared in a manner substantially analogous to General Procedure D in 10 mL 30% DMF/CH$_2$Cl$_2$ using 4-(5-Carbamoyl-thiophen-3-yl)-benzoic acid (360 mg, 1.6 mmol), EDC-HCl (439 mg, 2.3 mmol), HOBt (311 mg, 2.3 mmol), DIEA (0.70 mL, 4.0 mmol) and 2-(R)-Methyl-1-(2-(S)-pyrrolidinylmethyl)pyrrolidine (236 mg, 1.4 mmol) to give the title compound (80 mg, 14% yield). MS (ES+) 398.3 (M+H)+

Example 18

[4-(5-Bromo-thiophen-2-yl)-phenyl]-(2(S)-pyrrolidin-1-ylmethyl-pyrrolidin-1-yl)-methanone

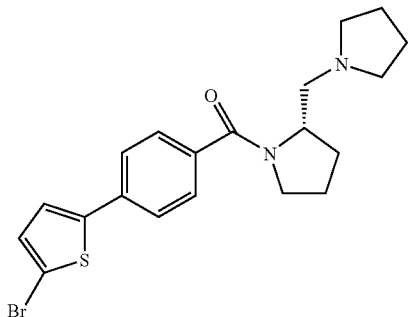

The title compound is prepared in a manner substantially analogous to General Procedure D using 4-(5-Bromo-thiophen-2-yl)-benzoic acid (CAS 1545208-54-4) and (S)(+)-1-(2-pyrrolidinylmethyl)pyrrolidine to give the title compound (5.42 g). MS (ES+) 419.0 (M+H)$^+$

Example 19

(2(S)-Pyrrolidin-1-ylmethyl-pyrrolidin-1-yl)-(6-thiophen-2-yl-pyridin-3-yl)-methanone

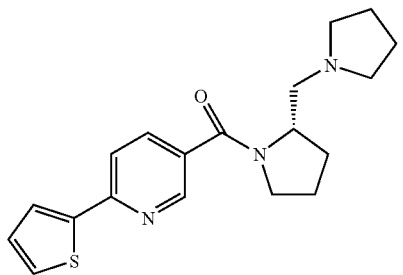

The title compound is prepared in a manner substantially analogous to General Procedure D using 6-thiophen-2-yl-nicotinic acid (CAS 179408-54-9) and (S)(+)-1-(2-pyrrolidinylmethyl)pyrrolidine to give the title compound (58 mg). MS (ES+) 342.1 (M+H)$^+$

Example 20

(2(S)-Pyrrolidin-1-ylmethyl-pyrrolidin-1-yl)-(6-thiophen-3-yl-pyridin-3-yl)-methanone

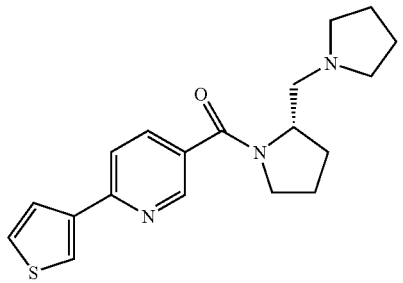

The title compound is prepared in a manner substantially analogous to General Procedure D using 6-thiophen-3-yl-nicotinic acid and (S)(+)-1-(2-pyrrolidinylmethyl)pyrrolidine to give the title compound (35 mg). MS (ES+) 342.1 (M+H)$^+$

Example 21

4-{4-[2-(S)-(2-(R)-methyl-pyrrolidin-1-ylmethyl)-pyrrolidine-1-carbonyl]-phenyl}-thiophene-2-carbonitrile

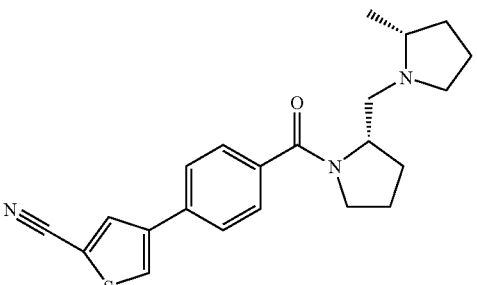

The title compound is prepared in a manner substantially analogous General Procedure A using 4-bromo-thiophene-2-carbonitrile (CAS 18791-99-6) and [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone to give the title compound. (150 mg, 30% yield). MS (ES+) 380.2 (M+H)$^+$

Example 22

(2-(S)-Pyrrolidin-1-ylmethyl-pyrrolidin-1-yl)-(4-thiazol-4-yl-phenyl)-methanone

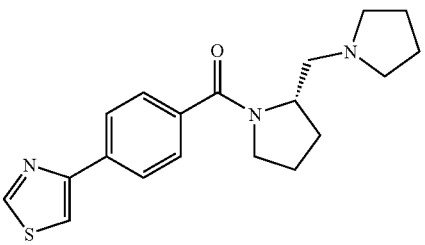

Procedure P: 4-Thiazol-4-yl-benzoic acid, lithium salt (0.10 g, 0.47 mmol) is suspended in dimethylformamide (5 mL). EDC (0.11 g, 0.56 mmol) and HOBt (0.077 g, 0.56 mmol) are added at room temperature in that order. DIEA (0.16 mL, 0.95 mmol) and (S)(+)-1-(2-pyrrolidinylmethyl) pyrrolidine (0.08 g, 0.52 mmol) are added to the mixture. The mixture is stirred at room temperature for overnight. Water and ethyl acetate is added to the mixture. The aqueous layer is washed several times with ethyl acetate. The combined organic layers are washed with brine (2×), dried over $Na_2SO_4$ and evaporated. The crude residue is purified by SCX chromatography (MeOH wash, then elution with 2M $NH_3$/MeOH) to give partially purified material. This material is then purified by silica-gel column chromatography (gradient: 100% $CH_2Cl_2$ to 10% 2M $NH_3$ in MeOH/$CH_2Cl_2$) to give the title compound (84.5 mg, 52%). MS (ES+) 342.3.

Example 23

(2-(S)-Pyrrolidin-1-ylmethyl-pyrrolidin-1-yl)-(4-thiazol-2-yl-phenyl)-methanone

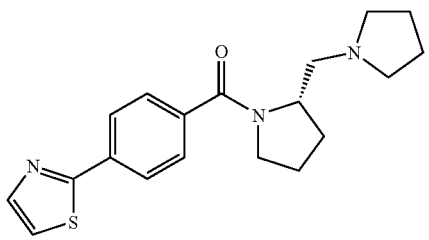

Procedure N: The title compound is prepared in a manner substantially analogous to Procedure P starting from 4-thiazol-2-yl-benzoic acid, lithium salt (CAS 266369-49-7) and (S)(+)-1-(2-pyrrolidinylmethyl)pyrrolidine. MS (ES+) 342.3

Example 24

[4-(2-Methanesulfonyl-thiazol-4-yl)-phenyl]-[2-(S)-(2-(R)-methyl-pyrrolidin-1-ylmethyl)-pyrrolidin-1-yl]-methanone

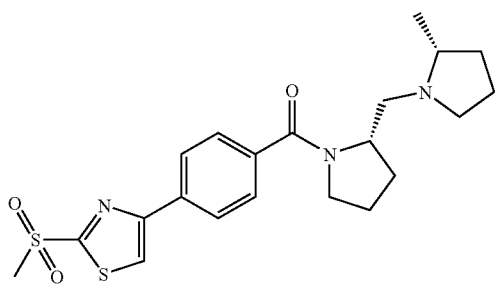

The title compound is prepared in a manner substantially analogous to Procedure N and Procedure P starting from 4-(2-Methanesulfonyl-thiazol-4-yl)-benzoic acid methyl ester and 2-(R)-Methyl-1-(2-(S)-pyrrolidinylmethyl)pyrrolidine. MS (ES+) 434.12.

Example 25

[4-(5-Phenyl-thiophen-2-yl)-phenyl]-((S)-2-pyrrolidin-1-ylmethyl-pyrrolidin-1-yl)-methanone

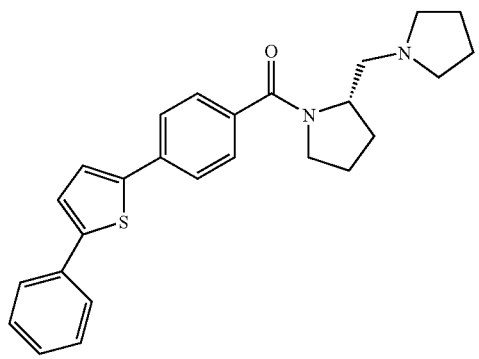

Procedure Q: To a stirred solution of 4-(2-Pyrrolidin-1-ylmethyl-pyrrolidine-1-carbonyl)-phenyl bromide (100 mg, 0.297 mmol), sodium carbonate (94.4 mg, 0.890 mmol) and 5-phenyl-2-thienyl boronic acid, (302 mg, 1.48 mmol) in toluene (5 mL), water (1 mL) and ethanol (1.5 mL) under nitrogen is added Tetrakis(triphenylphosphine)palladium (0) (34.3 mg, 0.030 mmol). The reaction is heated at reflux for 48 h. The reaction is allowed to cool and bound to a SCX-2 cartridge (10 g). The cartridge is washed with two cartridge volumes of dimethylformamide and one volume of methanol. The product is eluted using 2M ammonia in methanol. The ammonia/methanol solution is evaporated on a Genevac® HT4. The sample is further purified by prep-LCMS. The resulting acetonitrile/water fractions are combined and evaporated using a Genevac® to give 15 mg of a colourless oil (12%). MS (ES+) 417.2

Example 26

(4-Benzofuran-2-yl-phenyl)-((S)-2-pyrrolidin-1-ylmethyl-pyrrolidin-1-yl)-methanone

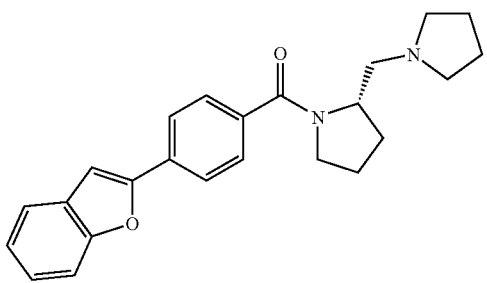

The title compound is prepared in a manner substantially analogous to Procedure Q starting from 2-Benzofuran boronic acid and 4-(2-Pyrrolidin-1-ylmethyl-pyrrolidine-1-carbonyl)-phenyl bromide to give 52 mg (47%). MS (ES+) 375.2

Example 27

[4-(4-Methyl-thiophen-2-yl)-phenyl]-((S)-2-pyrrolidin-1-ylmethyl-pyrrolidin-1-yl)-methanone

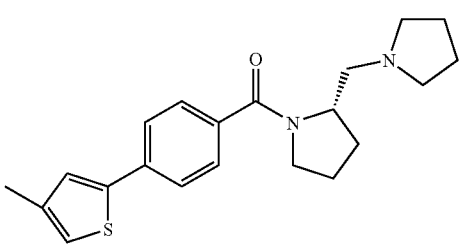

The title compound is prepared in a manner substantially analogous to Procedure Q starting from 4-Methyl-2-thiophene boronic acid and 4-(2-Pyrrolidin-1-ylmethyl-pyrrolidine-1-carbonyl)-phenyl bromide to give 70 mg (67%). MS (ES+) 355.2

Example 28

1-{5-[4-((S)-2-Pyrrolidin-1-ylmethyl-pyrrolidine-1-carbonyl)-phenyl]-thiophen-2-yl}-ethanone

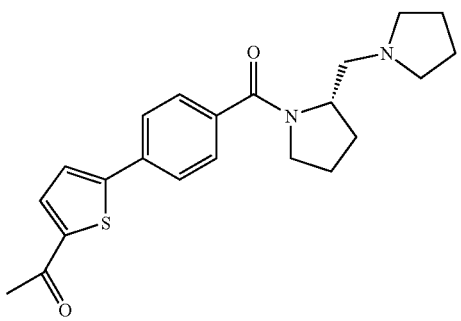

The title compound is prepared in a manner substantially analogous to Procedure Q starting from 5-Acetyl-2-thiophene boronic acid and 4-(2-Pyrrolidin-1-ylmethyl-pyrrolidine-1-carbonyl)-phenyl bromide to give 42 mg (37%). MS (ES+) 383.2

Example 29

4-Benzo[b]thiophen-2-yl-phenyl)-((S)-2-pyrrolidin-1-ylmethyl-pyrrolidin-1-yl)-methanone

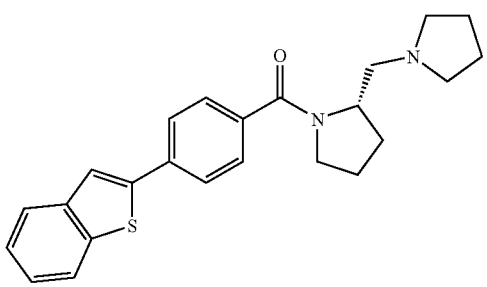

The title compound is prepared in a manner substantially analogous to Procedure Q starting from 2-benzothiophene boronic acid and 4-(2-Pyrrolidin-1-ylmethyl-pyrrolidine-1-carbonyl)-phenyl bromide to give 40 mg (34%). MS (ES+) 391.2

Example 30

((S)-2-Pyrrolidin-1-ylmethyl-pyrrolidin-1-yl)-(4-thiophen-3-yl-phenyl)-methanone

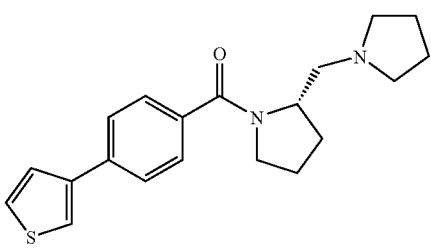

The title compound is prepared in a manner substantially analogous to Procedure Q starting from 3-Thiophene boronic acid and 4-(2-Pyrrolidin-1-ylmethyl-pyrrolidine-1-carbonyl)-phenyl bromide to give 56 mg (56%). MS (ES+) 341.2

Example 31

(2-Fluoro-4-thiophen-2-yl-phenyl)-((S)-2-pyrrolidin-1-ylmethyl-pyrrolidin-1-yl)-methanone

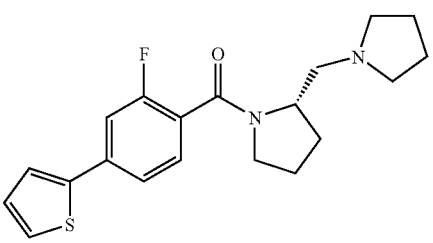

The title compound is prepared in a manner substantially analogous to Procedure Q starting from 2-thiophene boronic acid and (4-Bromo-2-fluoro-phenyl)-((S)-2-pyrrolidin-1-ylmethyl-pyrrolidin-1-yl)-methanone to give 29 mg (58%). MS (ES+) 359.1

Example 32

[4-(2,5-Dimethyl-pyrrol-1-yl)-phenyl]-(2-(S)-pyrrolidin-1-ylmethyl-pyrrolidin-1-yl)-methanone

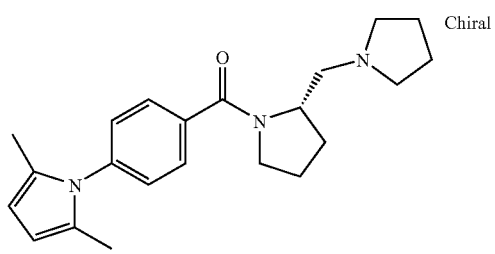

Procedure R: 151 mg of 4-(2,5-dimethyl-pyrrol-1-yl)-benzoic acid (CAS 15898-26-7) (0.7 mmol), 154 mg of (S)(+)-1-(2-pyrrolidinylmethyl)pyrrolidine (1.0 mmol) and 720 mg of PS-carbodiimide (1.0 mmol, mmol/g=1.32) are placed into 7 mL vial with 5.0 mL of 5% DMF in dichloromethane. The vial is capped and shaken at room temperature for overnight. The reaction mixture is filtered and washed by $CH_2Cl_2$. The filtrate is concentrated under $N_2$ gas. The crude product is applied to silica-gel column chromatography ($CH_2Cl_2$: 2M $NH_3$ in MeOH=40:1) to give the product. 68.2 mg. Yield 28%. MS (ES+): 352 (M+H)$^+$.

Example 33

(S)-2-[4-(2-Pyrrolidin-1-ylmethyl-pyrrolidine-1-carbonyl)-phenyl]-isoindole-1,3-dione

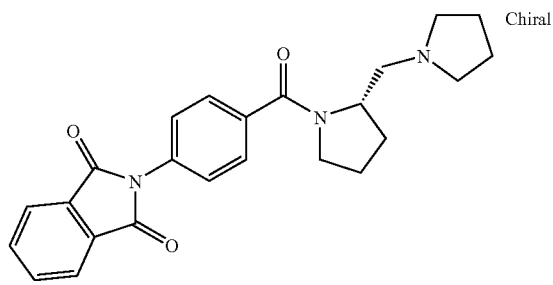

The title compound is prepared from N-(4-carboxyphenyl) phthalimide acid (CAS Registry #5383-82-4) in a manner substantially similar to Procedure R. MS (ES+) 404.

Example 34

(S)-[4-(4-Pyridin-4-yl-pyrazol-1-yl)-phenyl]-(2-pyrrolidin-1-ylmethyl-pyrrolidin-1-yl)-methanone

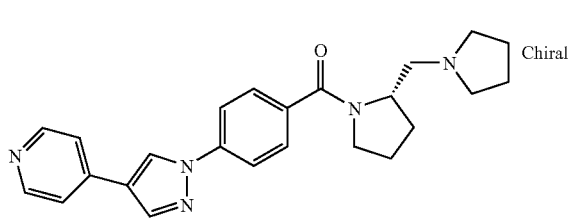

The title compound is prepared from 4-(4-pyridin-4-yl-pyrazol-1-yl)benzoic acid in a manner substantially similar to Procedure R. MS (ES+) 402.

Example 35

(S)-{4-[4-(4-Chloro-phenyl)-pyrazol-1-yl]-phenyl}-(2-pyrrolidin-1-ylmethyl-pyrrolidin-1-yl)-methanone

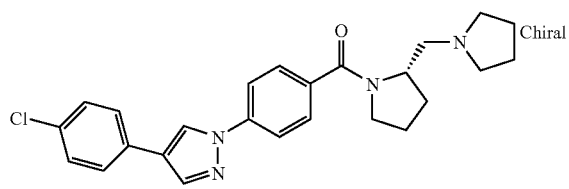

The title compound is prepared from 4-[4-(4-chlorophenyl)-pyrazol-1-yl]benzoic acid in a manner substantially similar to Procedure R. MS (ES+) 435.

Example 36

(S)-(4-Benzothiazol-2-yl-phenyl)-(2-pyrrolidin-1-ylmethyl-pyrrolidin-1-yl)methanone

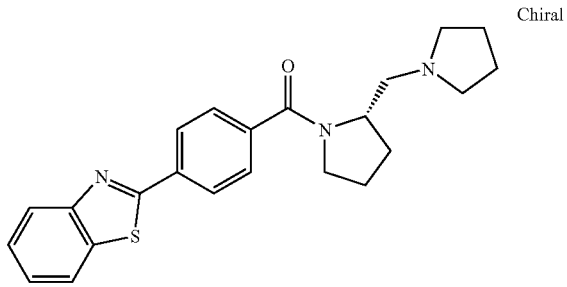

The title compound is prepared from 4-benzothiazol-2-yl-benzoic acid (CAS 2182-78-7) in a manner substantially similar to Procedure R. MS (ES+) 392.

Example 37

(S)-[4-(6-Methoxy-benzo[b]thiophen-2-yl)-phenyl]-(2-pyrrolidin-1-ylmethyl-pyrrolidin-1-yl)-methanone

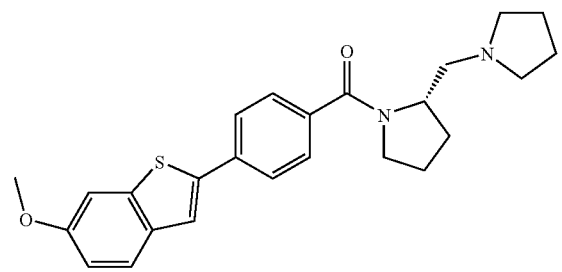

The title compound is prepared 4-(6-methoxy-benzo[b]thiophen-2-yl)-benzoic acid (CAS 588730-73-8) in a manner substantially similar to Procedure R. MS (ES+) 421.

Example 38

(S)-(2-Pyrrolidin-1-ylmethyl-pyrrolidin-1-yl)-(4-[1,2,3]thiadiazol-4-yl-phenyl-methanone

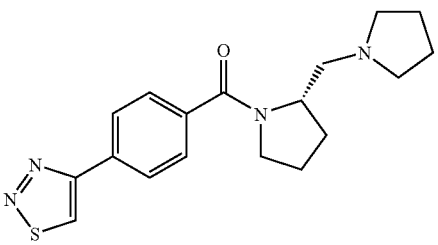

The title compound is prepared 4-(1,2,3-thiadiazol-4-yl) benzoic acid (CAS 18799-31-1) in a manner substantially similar to Procedure R. MS (ES+) 343.

Example 39

[4-(4-Pyridin-3-yl-thiazol-2-yl)-phenyl]-(2-pyrrolidin-1-ylmethyl-pyrrolidin-1-yl)-methanone; dihydrochloride

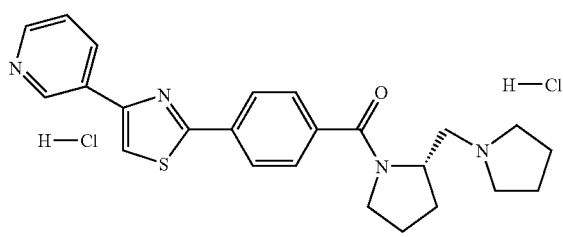

Procedure S: Sodium-4-(4-Pyridin-3-yl-thiazol-2-yl)-benzoic acid (0.201 g, 0.661 mmol) is slurried in 12 mL of toluene with oxalyl chloride (1.322 mmol, 0.116 mL), and 10 microliters of dimethylformamide. The mixture is heated to reflux for 2 minutes and then allowed to stir at ambient temperature for 2 hours. The reaction is concentrated to an oily solid which is triturated with dichloromethane. The dichloromethane is concentrated to the oily acid chloride intermediate which is used without any purification. The acid chloride is dissolved in dichloromethane and added to a mixture of (S)-(+)-1-(2-Pyrrolidinyl-methyl)pyrrolidine (Aldrich) (0.08 mmol, 0.0135 mL), and pyridine (0.2 mmol, 0.017 mL) and stirred for 20 minutes. The reaction is diluted with ethyl acetate and washed with aqueous sodium bicarbonate. The organics are separated and dried over sodium sulfate, filtered and concentrated to an oil. The oil is triturated with 1:1 hexane/diethyl ether to give the solid pure free base. The free base is dissolved in 1 mL of methanol and 0.15 mL of 1M HCl in diethyl ether is added to provide the titled compound after concentration. MS (m/e) 419.2 (M+1)

Example 40

N-(1-Methyl-1-{2-[4-(2-pyrrolidin-1-ylmethyl-pyrrolidine-1-carbonyl)-phenyl]thiazol-4-yl}-ethyl)-acetamide; hydrochloride

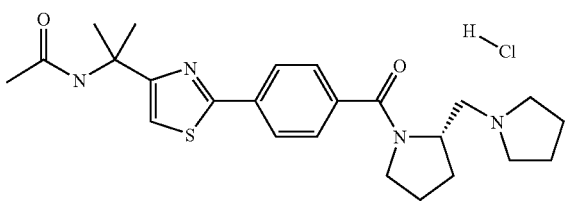

Procedure T: 4-[4-(1-Acetylamino-1-methyl-ethyl)-thiazol-2-yl]-benzoic acid (0.099 g, 0.325 mmol), N-methylmorpholine (1.0 mmol, 0.110 mL), and 2-Chloro-4,6-dimethoxy-[1,3,5]triazine (0.88 g, 0.5 mmol) are placed in a flask and dissolved in 6 mL dichloromethane. The reaction is stirred for 40 minutes and (S)-(+)-1-(2-Pyrrolidinyl-methyl)pyrrolidine (0.069 g, 0.45 mmol) is added and stirred for 1.5 hours. The reaction is diluted with ethyl acetate and washed with aqueous sodium bicarbonate. The organics are separated and dried over sodium sulfate, filtered, and concentrated to a oily residue. The residue is triturated with 3:1 diethyl ether/hexane and dried to give the pure free base. The free base is dissolved in 1 mL of dichloromethane and 1M HCl in diethyl ether is added to precipitate the pure titled compound. MS (m/e) 441.3 (M+1)

Example 41

{4-[4-(3-Ethoxy-phenyl)-thiazol-2-yl]-phenyl}-(2-pyrrolidin-1-ylmethyl-pyrrolidin-1-yl)-methanone; hydrochloride

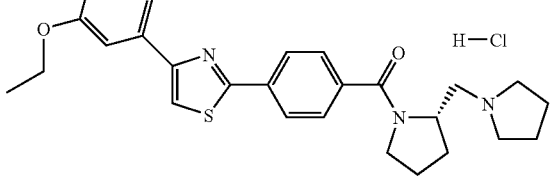

Procedure U: 4-[4-(3-Ethoxy-phenyl)-thiazol-2-yl]-benzoic acid (0.05 g, 0.154 mmol) [which can be obtained in a manner similar to the procedures detailed in Intermediate Preparation 21 and Intermediate Preparation 22 using 2-Bromo-1-(3-ethoxy-phenyl)-ethanone (CAS 103793-40-4) and 4-Thiocarbamoyl-benzoic acid ethyl ester] is dissolved in 3 mL of dimethylformamide and 1-(3-Dimethylaminopropyl)-3-ethyl-carbodiimide hydrochloride (0.03 g, 0.157 mmol), and (S)-(+)-1-(2-Pyrrolidinyl-methyl)pyrrolidine (0.023 g, 0.150 mmol) are added and stirred for 18 hours at ambient temperature. The reaction is diluted with ethyl acetate and washed successively with sodium bicarbonate solution and brine. The organics are separated and dried over sodium sulfate, filtered, and concentrated to a crude residue. The residue is purified by reverse phase chromatography. The purified material is dissolved in 0.5 mL of methanol and 1M HCl in diethyl ether is added to provide the titled compound. MS (m/e) 462.5 (M+1)

Example 42

N-(1-Methyl-1-{2-[4-(2-pyrrolidin-1-ylmethyl-pyrrolidine-1-carbonyl)-phenyl]-thiazol-4-yl}-ethyl)-benzamide hydrochloride

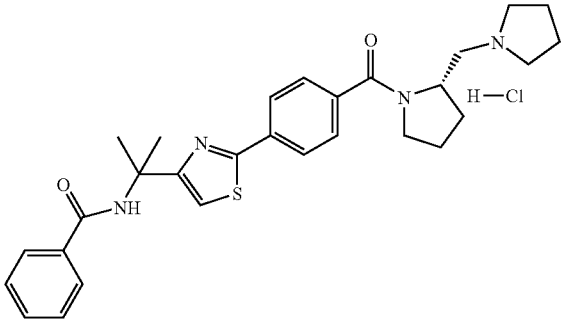

The titled compound is prepared substantially in accordance with the procedure found in Procedure T using sodium-4-[4-(1-Benzoylamino-1-methyl-ethyl)-thiazol-2-yl]-benzoic acid MS (m/e): 503.3 (M+1)

Example 43

[4-(5-Chloro-1H-benzoimidazol-2-yl)-phenyl]-(2-pyrrolidin-1-ylmethyl-pyrrolidin-1-yl)-methanone

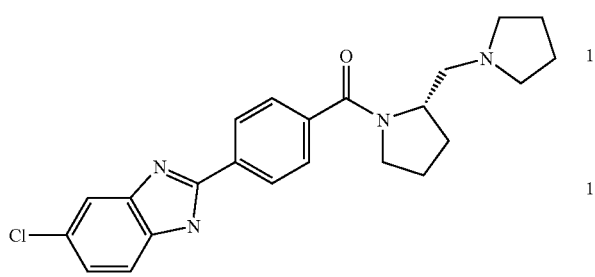

To a stirring solution of (S)-(+)-1-(2-pyrrolidinylmethyl) pyrrolidine (11.0 mmol) and n-methylmorpholine (1.0 mmol) in dichloromethane (0.10M), slowly add the product from 4-(5-Chloro-1H-benzoimidazol-2-yl)-benzoyl chloride (1.0 mmol) diluted in dichloromethane. Stir reaction at room temperature for two hours. After this time wash the reaction with saturated aqueous sodium bicarbonate while extracting with 10% isopropanol/dichloromethane. Concentrate the organics in vacuo. Purify via radial chromatography eluting with 2M ammonia in methanol and dichloromethane. MS (m/e): 409.3 (M+1)

Example 44

[4-(5-Chloro-1H-benzoimidazol-2-yl)-phenyl]-(2-pyrrolidin-1-ylmethyl-pyrrolidin-1-yl)-methanone dihydrochloride salt

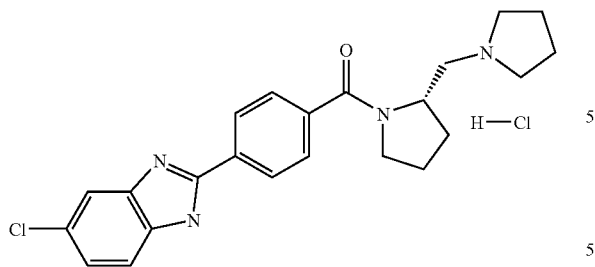

Dissolve [4-(5-chloro-1H-benzoimidazol-2-yl)-phenyl]-(2-pyrrolidin-1-ylmethyl-pyrrolidin-1-yl)-methanone dihydrochloride salt in minimal dichloromethane and add 1M hydrochloric acid in ether until the solution becomes cloudy. Add 1:1 ether/hexanes and concentrate in vacuo to yield the salt. MS (m/e): 409.3 (M+1)

Example 45

[2-(S)-(2-(R)-methyl-pyrrolidin-1-ylmethyl)-pyrrolidin-1-yl]-{4-[5-(pyrrolidine-1-carbonyl)-thiophen-2-yl]-phenyl}-methanone

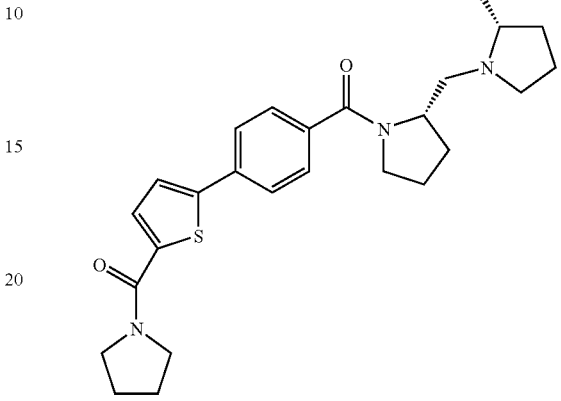

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (398 mg, 1.0 mmol) and (5-Bromo-thiophen-2-yl)-pyrrolidin-1-yl-methanone (CAS 326875-64-3) 261 mg, 1.0 mmol) to give 150 mg (34% yield). MS (ES+) 452.2 (M+H)$^+$

Example 46

{4-[5-(Azetidine-1-carbonyl)-thiophen-2-yl]-phenyl}-[2-(S)-(2-(R)-methyl-pyrrolidin-1-ylmethyl)-pyrrolidin-1-yl]-methanone

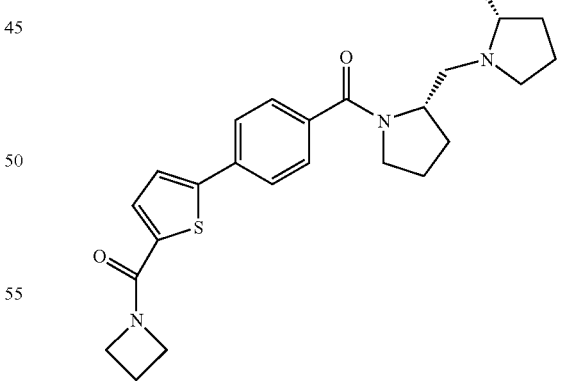

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (367 mg, 0.92 mmol) and azetidin-1-yl-(5-bromo-thiophen-2-yl)-methanone) (226 mg, 0.92 mmol) to give 80 mg (21% yield). MS (ES+) 438.3 (M+H)$^+$

Example 47

[2-(S)-(2-(R)-methyl-pyrrolidin-1-ylmethyl)-pyrrolidin-1-yl]-{4-[5-(piperidine-1-carbonyl)-thiophen-2-yl]-phenyl}-methanone

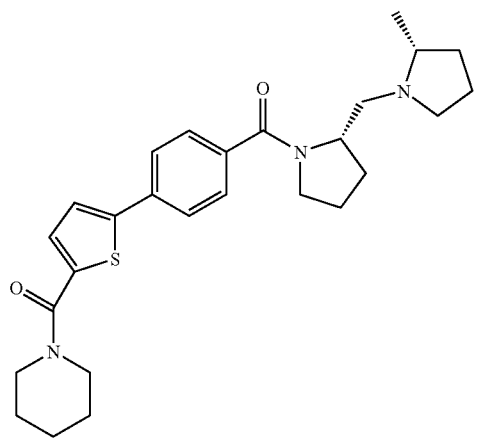

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (550 mg, 1.4 mmol) and (5-Bromo-thiophen-2-yl)-piperidin-1-yl-methanone (CAS 626242-11-3) (315 mg, 1.2 mmol) to give 260 mg (48% yield). MS (ES+) 466.2 (M+H)+

Example 48

[2-(S)-(2-(R)-methyl-pyrrolidin-1-ylmethyl)-pyrrolidin-1-yl]-{4-[5-(pyrrolidine-1-carbonyl)-thiazol-2-yl]-phenyl}-methanone

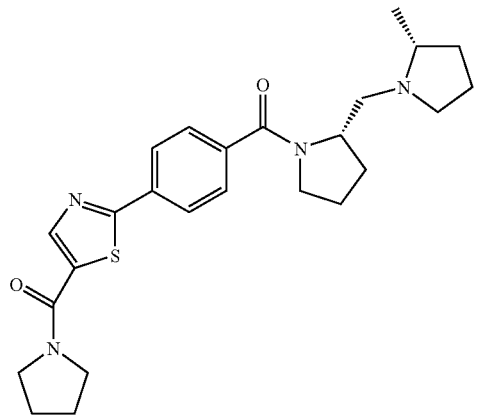

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (199 mg, 0.5 mmol) and (2-bromo-thiazol-5-yl)-pyrrolidin-1-yl-methanone (120 mg, 0.46 mmol) to give 30 mg (14% yield). MS (ES+) 453.3 (M+H)+

Example 49

{2-Fluoro-4-[5-(pyrrolidine-1-carbonyl)-thiophen-2-yl]-phenyl}-[2-(S)-(2-(R)-methyl-pyrrolidin-1-ylmethyl)-pyrrolidin-1-yl]-methanone

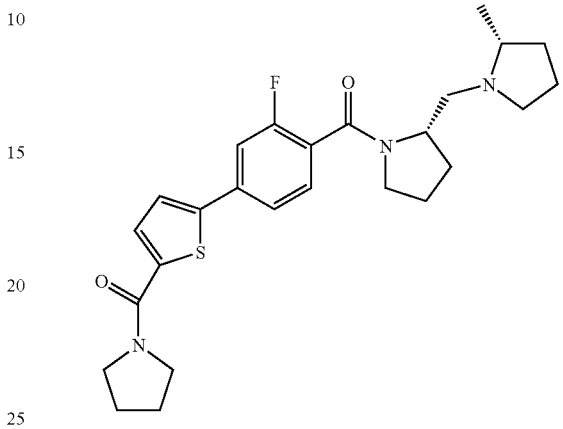

The title compound is prepared in a manner substantially analogous to General Procedure A using [2-Fluoro-4-(4,4,5,5-tetramethyl-[1,3,2]dioxaborolan-2-yl)-phenyl]-[2-(S)-(2-(R)-methyl-pyrrolidin-1-ylmethyl)-pyrrolidin-1-yl]-methanone (408 mg, 0.98 mmol) and (5-Bromo-thiophen-2-yl)-pyrrolidin-1-yl-methanone (CAS 326875) (256 mg) MS 470.2 (M+H)+

Example 50

[2-Fluoro-4-(5-methanesulfonyl-thiophen-2-yl)-phenyl]-[2-(S)-(2-(R)-methyl-pyrrolidin-1-ylmethyl)-pyrrolidin-1-yl]-methanone

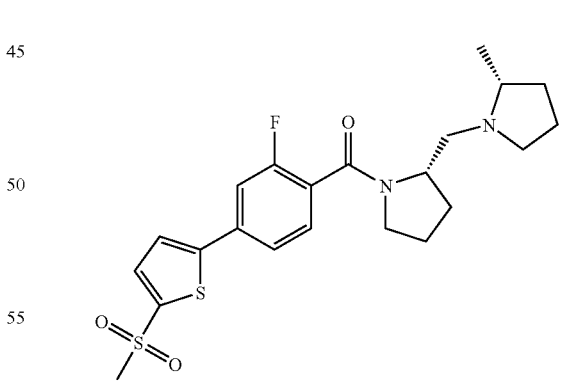

The title compound is prepared in a manner substantially analogous to General Procedure A using [2-Fluoro-4-(4,4,5,5-tetramethyl-[1,3,2]dioxaborolan-2-yl)-phenyl]-[2-(S)-(2-(R)-methyl-pyrrolidin-1-ylmethyl)-pyrrolidin-1-yl]-methanone (458 mg, 1.1 mmol) and 2-Bromo-5-methanesulfonyl-thiophene (CAS 2160-61-4) (255 mg, 1.0 mmol) to give 350 mg (78% yield). MS (ES+) 451.2 (M+H)+

Example 51
[4-(5-Ethanesulfonyl-thiophen-2-yl)-2-fluoro-phenyl]-[2-(S)-(2-(R)-methyl-pyrrolidin-1-ylmethyl)-pyrrolidin-1-yl]-methanone

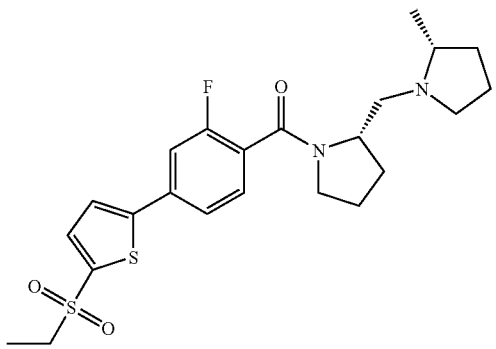

The title compound is prepared in a manner substantially analogous to General Procedure A using [2-Fluoro-4-(4,4,5,5-tetramethyl-[1,3,2]dioxaborolan-2-yl)-phenyl]-[2-(S)-(2-(R)-methyl-pyrrolidin-1-ylmethyl)-pyrrolidin-1-yl]-methanone (458 mg, 1.1 mmol) and 2-Bromo-5-ethanesulfonyl-thiophene (255 mg, 1.0 mmol) to give 165 mg (35% yield). MS (ES+) 465.2 (M+H)+

Example 52
5-{4-[2-(S)-(2-(R)-methyl-pyrrolidin-1-ylmethyl)-pyrrolidine-1-carbonyl]-phenyl}-thiophene-3-carbonitrile

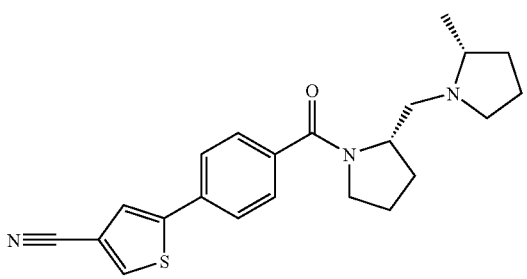

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (351 mg, 0.88 mmol) and 5-Iodo-thiophene-3-carbonitrile (CAS 18800-02-7) (165 mg, 0.88 mmol) to give 100 mg (30% yield). MS (ES+) 380.2 (M+H)+

Example 53
[4-(1-Methyl-1H-imidazol-2-yl)-phenyl]-[2-(S)-(2-(R)-methyl-pyrrolidin-1-ylmethyl)-pyrrolidin-1-yl]-methanone

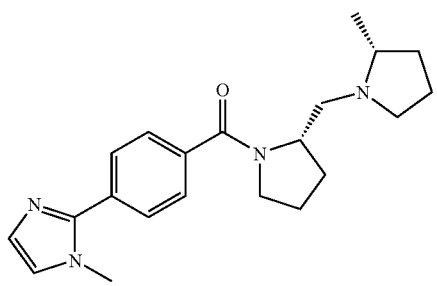

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (439 mg, 1.1 mmol) and 2-Bromo-1-methyl-1H-imidazole (CAS 16681-59-7) (161 mg, 1.0 mmol) to give 39 mg (11% yield). MS (ES+) 353.2 (M+H)+

Example 54
{2-Fluoro-4-[5-(pyrrolidine-1-carbonyl)-thiazol-2-yl]-phenyl}-[2-(S)-(2-(R)-methyl pyrrolidin-1-ylmethyl)-pyrrolidin-1-yl]-methanone

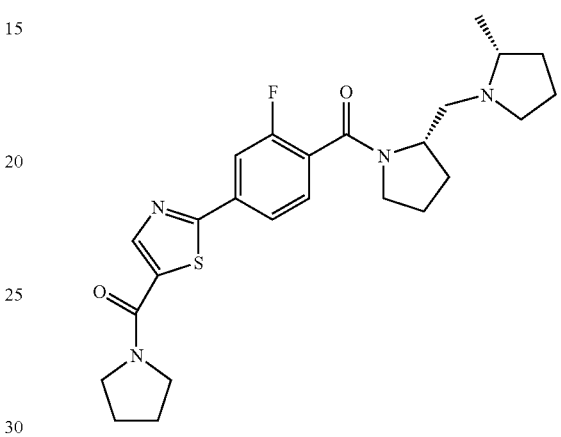

The title compound is prepared in a manner substantially analogous to General Procedure A using [2-Fluoro-4-(4,4,5,5-tetramethyl-[1,3,2]dioxaborolan-2-yl)-phenyl[2-(S)-(2-(R)-methyl-pyrrolidin-1-ylmethyl)-pyrrolidin-1-yl]-methanone (354 mg, 0.85 mmol) and (2-bromo-thiazol-5-yl)-pyrrolidin-1-yl-methanone (222 mg, 0.85 mmol) to give 130 mg (32% yield). MS (ES+) 471.3 (M+H)+

Example 55
5-{4-[2-(S)-(2-(R)-methyl-pyrrolidin-1-ylmethyl)-pyrrolidine-1-carbonyl]-phenyl}-thiophene-2-carbaldehyde O-methyl-oxime

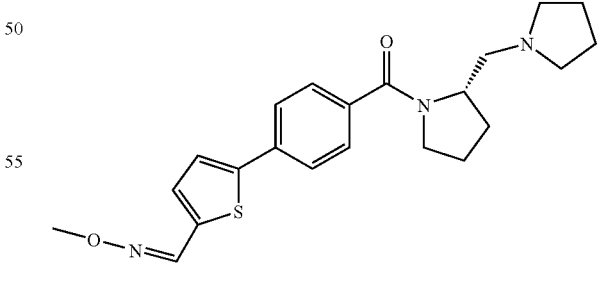

The title compound is prepared in a manner substantially analogous to General Procedure A using [2-(S)-(2-(R)-methyl-pyrrolidin-1-ylmethyl)-pyrrolidin-1-yl]-[4-(4,4,5,5-tetramethyl-[1,3,2]dioxaborolan-2-yl)-phenyl]-methanone (351 mg, 0.88 mmol) and 2-Bromo-thiazole-5-carbaldehyde O-methyl-oxime (176 mg, 0.80 mmol) to give 166 mg (59% yield). MS (ES+) 412.3 (M+H)+

Example 56

5-Methyl-1-[4-(2-(S)-pyrrolidin-1-ylmethyl-pyrrolidine-1-carbonyl)-phenyl]-1H-pyrazole-4-carboxylic acid ethyl ester L-tartrate

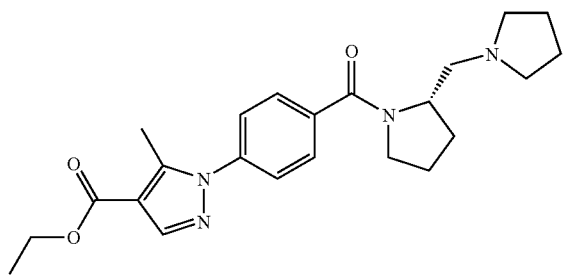

A mixture of ethyl 1-(4-carboxyphenyl)-5-methyl-pyrazole-4-carboxylate (548 mg, 2 mmole), (S)-(+)-1-(2-Pyrrolidinyl-methyl)pyrrolidine (308 mg, 2 mmole), TBTU (700 mg, 2.2 mmole) and triethylamine (300 mg, 3 mmole) in dimethylformamide (15 mL) is stirred at room temperature for 6 hours. Water is added and the product extracted with ethyl acetate. The solvent is washed with water, dried and evaporated in vacuo. The product is purified by chromatography on silica gel by elution with 10% methanol in dichloromethane. The product is converted to the title compound using L-tartaric acid in methanol. MS (m/e): 411.2 (M+1).

Example 57

{5-Methyl-1-[4-(2-(S)-pyrrolidin-1-ylmethyl-pyrrolidine-1-carbonyl)-phenyl]-1H-pyrazol-4-yl}-pyrrolidin-1-yl-methanone

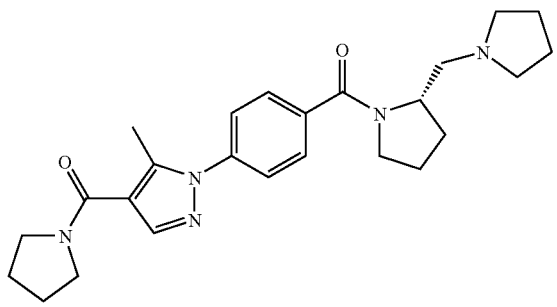

5-Methyl-1-[4-(2-(S)-pyrrolidin-1-ylmethyl-pyrrolidine-1-carbonyl)-phenyl]-1H-pyrazole-4-carboxylic acid ethyl ester from Example 56 (270 mg, 0.66 mmole) is hydrolysed using lithium hydroxide in aqueous methanol and the resulting lithium salt recovered by freeze drying. The lithium salt, pyrrolidine (140 mg, 2 mmole), TBTU (325 mg, 1 mmole) and triethylamine (212 mg, 2 mmole) are dissolved in dimethylformamide (10 mL) and the mixture is stirred for 18 hours. The reaction is diluted with water, extracted with ethyl acetate, washed with water, dried and evaporated to dryness. The product is purified by chromatography on silica gel using 10% methanol in dichloromethane and the title compound recovered by crystallization from ethyl acetate. MS (m/e): 436.3 (M+1).

The pharmaceutical salts of the invention are typically formed by reacting a compound of Formula I or Formula II with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or Formula II may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or Formula II is preferably formulated in a unit dosage form prior to administration. Therefore, yet another embodiment of the present invention is a pharmaceutical composition comprising a compound of Formula I or Formula II and one or more pharmaceutically acceptable carriers, diluents or excipients. The present pharmaceutical compositions are prepared by known procedures using well-known and readily available ingredients. Preferably the compound is administered orally. Preferably, the pharmaceutical composition is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Utility

Compounds of Formula I or Formula II are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I or Formula II are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels and possibly that of other monoamines resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (Preparation of Histamine Receptor Subtype Membranes) for the histamine receptor subtypes.

Membranes isolated as described in (Preparation of Histamine Receptor Subtype Membranes) were used in a [35S] GTPχS functional assay. Binding of [35S]GTPχS to membranes indicates agonist activity. Compounds of the invention of Formula I or Formula II were tested for their ability to inhibit binding in the presence of agonists. Alternately, the same transfected cell lines were used for a cAMP assay wherein H3R agonists inhibited forskolin-activated synthesis of cAMP. Compounds of Formula I or Formula II were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitogen) and transfected into HEK293 cells using the FuGENE Tranfection Reagent (Roche Diagnostics Corporation). Transfected cells were selected using G418 (500 µ/mL). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 µl). Astemizole (10M, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 mL assay buffer, mixed by vortexing, and centrifuged (40,000 g at 4° C.) for 10 minutes. The pellet resuspension, vortexing, and centrifugation was repeated 2 more times. The final cell pellet was resuspended in 30 mL and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 µl). Cimetidine (10M, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 µ/mL), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM ($^3$H)-n-alpha-methylhistamine (NEN, NET1027) (total volume per well=200 µl). Thioperimide was added to determine non-specific binding. Several clones were selected as positive for binding, and a single clone (H3R8) was used to prepare membranes for binding studies described above. Five micrograms of protein was used per well in the SPA receptor-binding assay.

D. Preparation of GPRv53 Membranes cDNA for the human GPRv53 receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/mL G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harvester. Filters were counted with melt-on scintillator sheets (Perkin Elmer) in a Wallac Trilux 1450 Microbeta Scintillation counter for 5 minutes.

Pharmacological Results cAMP ELISA

HEK293 H3R8 cells prepared as described above were seeded at a density of 50,000 cells/well and grown overnight in DMEM/F12 (Gibco) supplemented with 5% FBS and 500 ug/mL G418. The next day tissue culture medium was removed and replaced with 50 µl cell culture medium containing 4 mM 3-isobutyl-1-methylxanthine (Sigma) and incubated for 20 minutes at room temperature. Antagonist were added in 50 µl cell culture medium and incubated for 20 minutes at room temperature. Agonist R (−)α methylhistamine (RBI) at a dose response from $1\times10^{-10}$ to $1\times10^{-5}$ M was then added to the wells in 50 µl cell culture medium and incubated for 5 minutes at room temperature. Then 50 µl of cell culture medium containing 20 µM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTP γ [S] Binding Assay

Antagonist activity of selected compounds was tested for inhibition of [35S] GTP γ [S] binding to H3R membranes in the presence of agonists. Assays were run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 µl assay buffer. Antagonist was then added to the wells in a volume of 50 µl assay buffer and incubated for 15 minutes at room temperature. Agonist R(−) alpha methylhistamine (RBI) at either a dose response from $1\times10^{-10}$ to $1\times10^{-5}$ M or fixed concentration of 100 nM were then added to the wells in a volume of 50 µl assay buffer and incubated for 5 minutes at room temperature. GTP γ [35S] was added to each well in a volume of 50 µl assay buffer at a final concentration of 200 pM, followed by the addition of 50 µl of 20 mg/mL WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i](nM).

All compounds set forth in the examples exhibit affinity for the H3 receptor greater than 1 uM in the H3R binding assay. Preferred compounds of the invention exhibit affinity for the H3 receptor greater than 200 nM. Most preferred compounds of the invention exhibit affinity for the H3 receptor greater than 20 nM. The results are given below for the indicated compound.

TABLE 2

| Example | Ki (nM) |
|---|---|
| (structure) | 13.8 |
| (structure) | 3.1 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

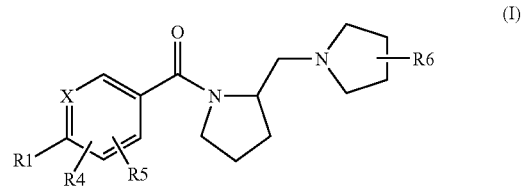

or a pharmaceutically acceptable salt thereof wherein;

X independently represents carbon (substituted with hydrogen or the optional substituents indicated herein), or nitrogen;

R1 is independently -HET (optionally substituted on carbon, independently, one to three times with R2, and optionally once substituted on nitrogen with R3), or -Benzofused heterocycle (optionally substituted on carbon, independently, one to three times with R2, and optionally once substituted on nitrogen with R3);

R2 is independently at each occurrence
—H, -halogen, —($C_1$-$C_7$) alkyl (optionally substituted with one to three halogens), —CN, —C(O)R7, —C(O)OR7, —C(O)($C_3$-$C_5$)cycloalkyl (optionally substituted with one to three halogens), —C(O)NR7R8, —OR7, —$NO_2$, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -phenyl-R9, —C(H)=NO—R7, -pyridinyl, -HET-R9, or —($C_1$-$C_7$)alkyl-NHC (O)R7 (provided that not more than one occurrence of R2 is -HET-R9 or -phenyl-R9);

R3 is independently at each occurrence
- —H, —($C_1$-$C_7$) alkyl (optionally substituted with one to three halogens), —$SO_2$R7, —C(O)R7, —C(O)NR7R8, or —C(O)OR7;

R4 and R5 are independently
- —H, —OH, -halogen, —($C_1$-$C_3$)alkyl (optionally substituted with one to three halogens), or —OR9, provided that when X is nitrogen, then R4 and R5 are not attached to X;

R6 is independently
- —H, -halogen, —($C_1$-$C_3$) alkyl (optionally substituted with one to three halogens), —$NH_2$, —NR7R8, —OH, or —OR7;

R7 and R8 are independently
- —H, -phenyl, —($C_1$-$C_7$) alkyl (optionally substituted with one to three halogens); or R7 and R8 combine with the atom to which they are attached to form a 4 to 7 membered ring;

R9 is
- —H, -halogen, —($C_1$-$C_3$) alkyl (optionally substituted with one to three halogens), or —OR7.

2. The compound or salt of claim 1 wherein X represents carbon (substituted with hydrogen or the optional substituents indicated herein).

3. The compound or salt of claim 1 wherein X represents nitrogen.

4. The compound or salt of claim 1 wherein R1 is independently

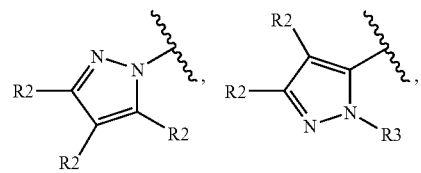

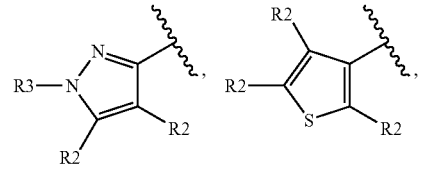

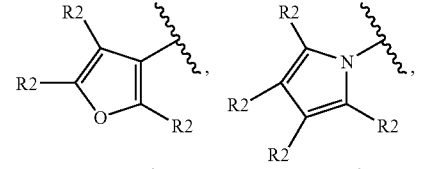

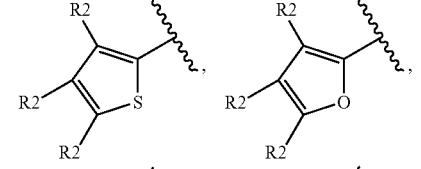

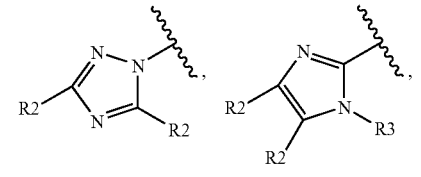

-continued

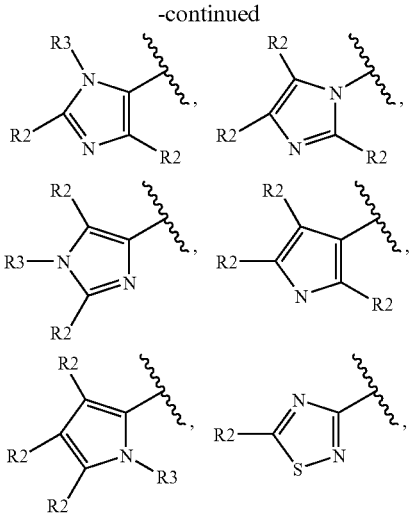

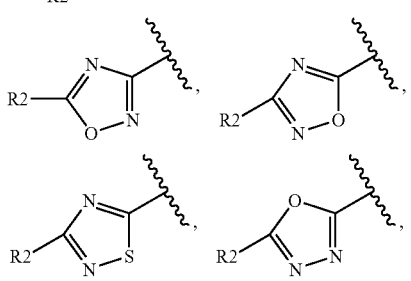

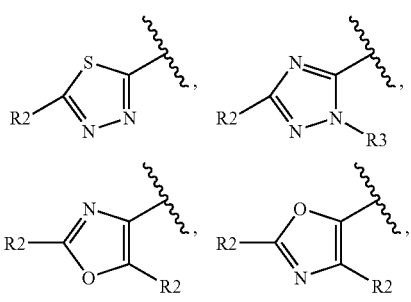

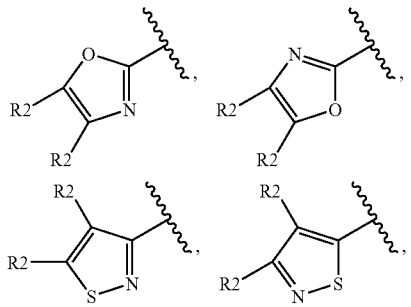

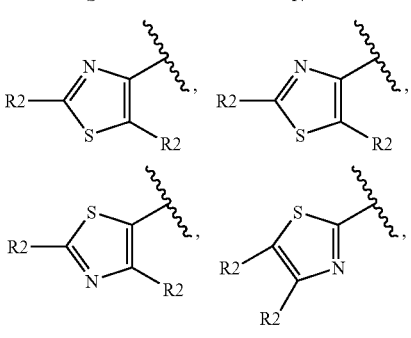

-continued

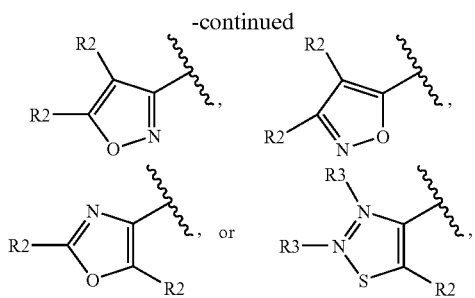

wherein the bond directed to the zig-zag lines indicates the point of attachment to the position indicated by R1 in Formula I.

5. The compound or salt of claim 1 wherein R1 is independently

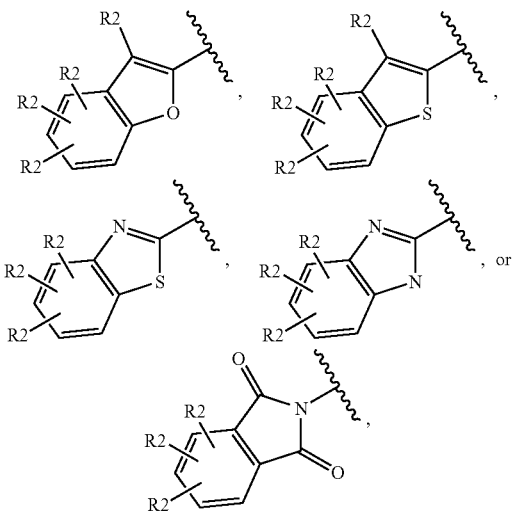

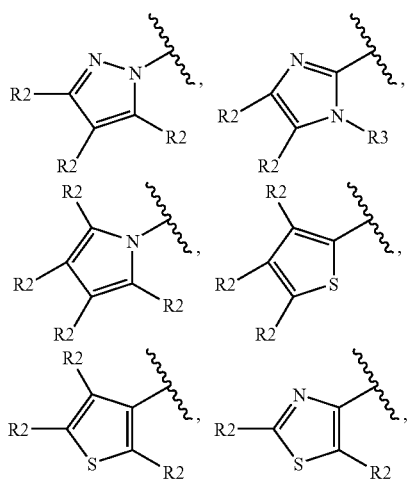

wherein the bond directed to the zig-zag lines indicates the point of attachment to the position indicated by R1 in Formula I.

6. The compound or salt of claim 1 wherein R1 is selected from the group consisting of

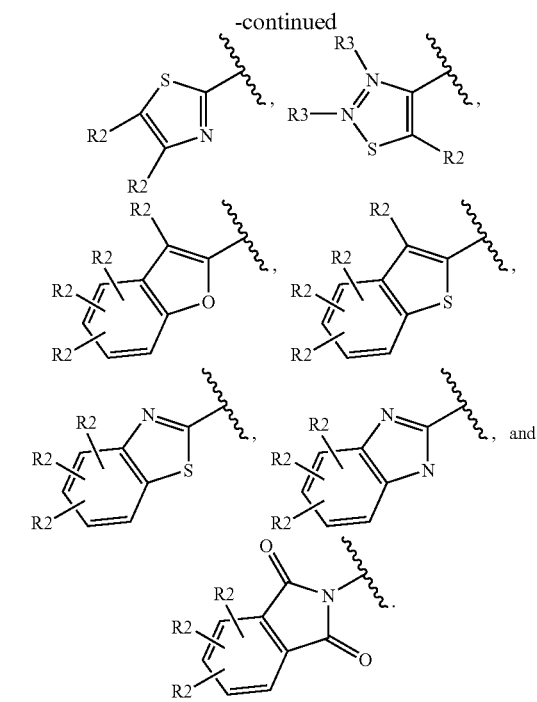

7. The compound or salt of claim 1 wherein R6 is —(C$_1$-C$_3$) alkyl (optionally substituted with one to three halogens).

8. The compound or salt of claim 6 wherein R6 is —CH$_3$.

9. The compound or salt of claim 1 wherein R2 is independently at each occurrence —H, -halogen, —(C$_1$-C$_7$) alkyl (optionally substituted with one to three halogens), —CN, —C(O)R7, —C(O)OR7, —C(O)(C$_3$-C$_5$)cycloalkyl, —C(O)NR7R8, —OR7, —NO$_2$, —NR7R8, —NR9SO$_2$R7, —NR9C(O)R7, —NR9CO$_2$R7, —NR9C(O)NR7R8, —SR7, —SO$_2$R7, —SO$_2$NR7R8, —S(O)R7, -phenyl-R9, —C(H)=NO—R7, -pyridinyl, -HET-R9, or —(C$_1$-C$_7$)alkyl-NHC(O)R7 (provided that not more than one occurrence of R2 is -HET-R9, -phenyl-R9, or -pyridinyl); R3 is independently at each occurrence —H, —(C$_1$-C$_3$) alkyl (optionally substituted with one to three halogens), —SO$_2$R7, —C(O)R7, —C(O)NR7R8, or —C(O)OR7; R4 and R5 are independently —H, —OH, -halogen, —CH$_3$, —CF$_2$H, —CF$_3$, or —OCH$_3$, provided that when X is nitrogen, then R4 and R5 are not attached to X; R6 is independently —H, -halogen, or —(C$_1$-C$_3$) alkyl (optionally substituted with one to three halogens); R7 and R8 are independently —H, —(C$_1$-C$_4$) alkyl (optionally substituted with one to three halogens); or R7 and R8 combine with the atom to which they are attached to form a 4 to 6 membered ring; and R9 is —H, -halogen, —(C$_1$-C$_3$) alkyl (optionally substituted with one to three halogens), or —OR7.

10. The compound or salt of claim 1 wherein X independently represents carbon (substituted with hydrogen or the optional substituents indicated herein), or nitrogen; R1 is

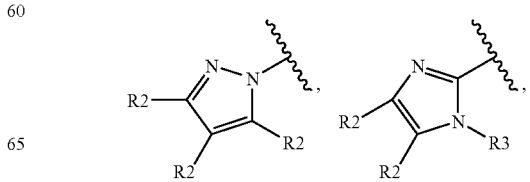

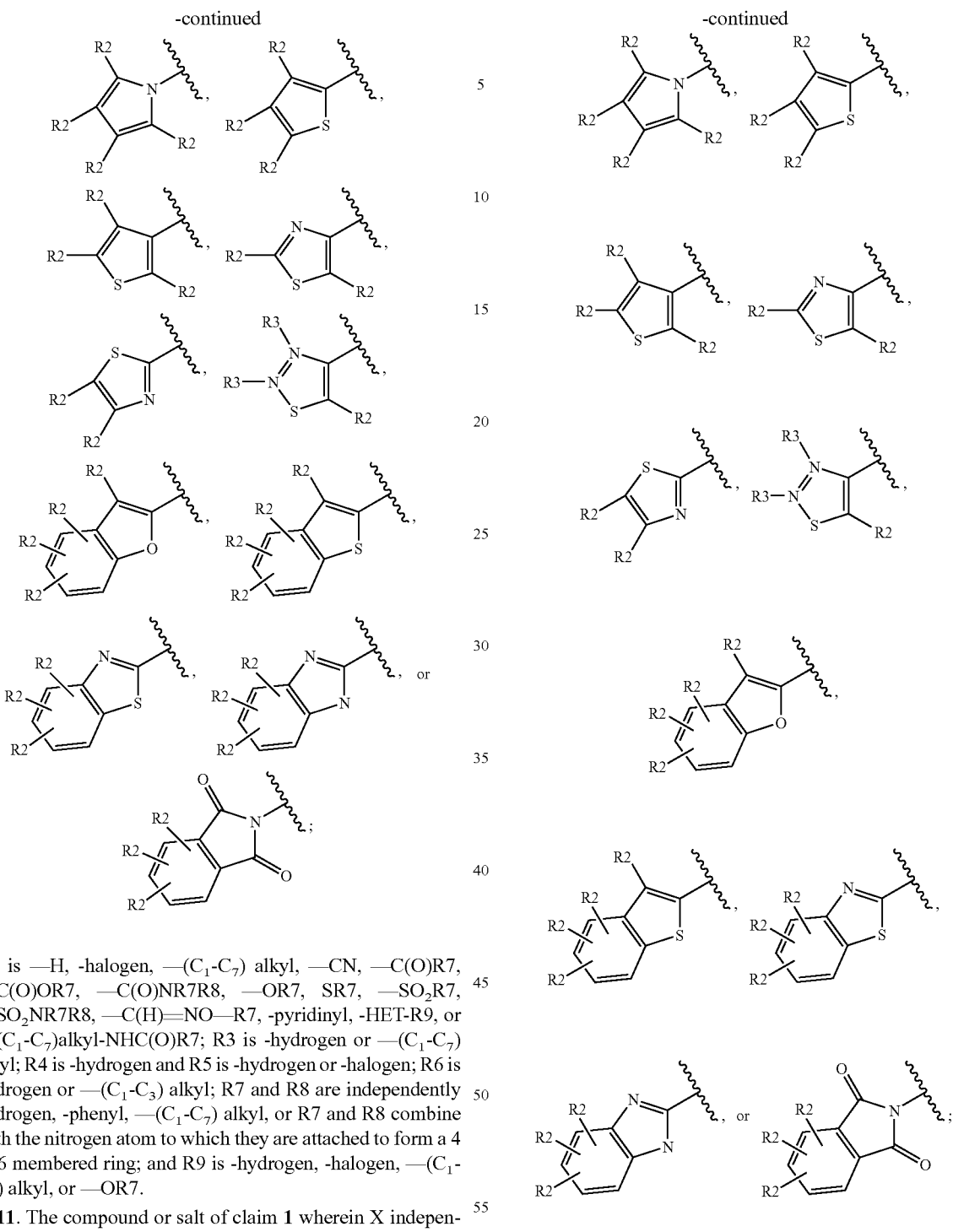

R2 is —H, -halogen, —(C₁-C₇) alkyl, —CN, —C(O)R7, —C(O)OR7, —C(O)NR7R8, —OR7, SR7, —SO₂R7, —SO₂NR7R8, —C(H)=NO—R7, -pyridinyl, -HET-R9, or —(C₁-C₇)alkyl-NHC(O)R7; R3 is -hydrogen or —(C₁-C₇) alkyl; R4 is -hydrogen and R5 is -hydrogen or -halogen; R6 is hydrogen or —(C₁-C₃) alkyl; R7 and R8 are independently hydrogen, -phenyl, —(C₁-C₇) alkyl, or R7 and R8 combine with the nitrogen atom to which they are attached to form a 4 to 6 membered ring; and R9 is -hydrogen, -halogen, —(C₁-C₃) alkyl, or —OR7.

11. The compound or salt of claim 1 wherein X independently represents carbon (substituted with hydrogen or the optional substituents indicated herein), or nitrogen; R1 is R2 is —H, —Br, —Cl, —CH₃, —CN, —C(O)CH₃, —C(O)CH(CH₃)₂, —C(O)OCH₂CH₃, —C(O)NH₂, —C(O)N(CH₃)₂, —C(O)-pyrrolidinyl, —C(O)N-azetidinyl, —C(O)N-piperidinyl, —OCH₃, —SCH₃, —SO₂CH₃, —SO₂CH₂CH₃, —SO₂NH₂, -oxazolyl, -phenyl, -3-ethoxyphenyl, -4-chlorophenyl, -4-pyridinyl, -3-pyridinyl, —N-isopropylacetamide, —N-isopropylbenzamide, or -2-carbaldehyde-O-methyl-oxime; R3 is -hydrogen or —CH₃; R4 is -hydrogen and R5 is hydrogen or —F; and R6 is hydrogen or —CH₃.

12. The compound of claim 1 selected from the group consisting of formula X1 to X43, X45 to X57:

| Formula Number | Structure |
|---|---|
| X1 | (structure) |
| X2 | (structure) |
| X3 | (structure) |
| X4 | (structure) |

-continued
| Formula Number | Structure |
|---|---|
| X5 | 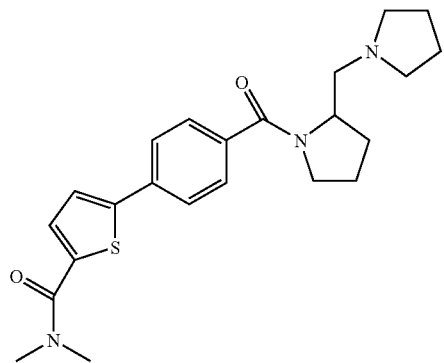 |
| X6 | 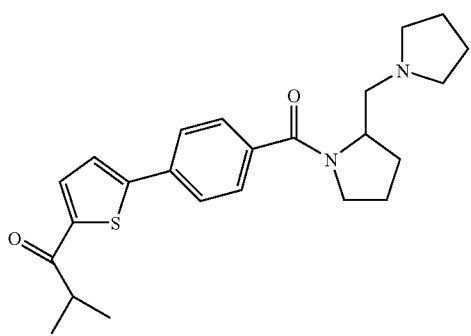 |
| X7 | 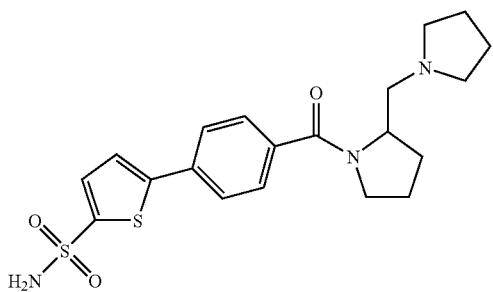 |
| X8 | 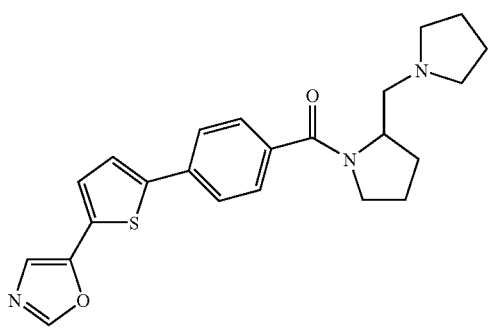 |

-continued
| Formula Number | Structure |
|---|---|
| X9 | 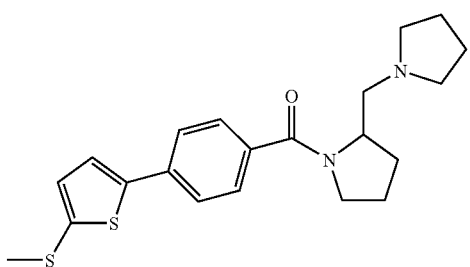 |
| X10 | 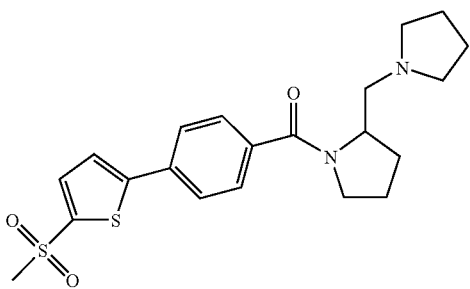 |
| X11 | 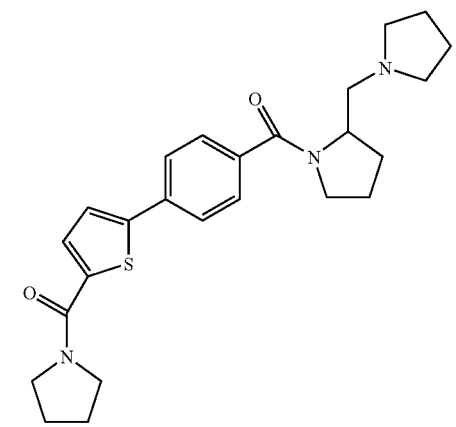 |
| X12 | 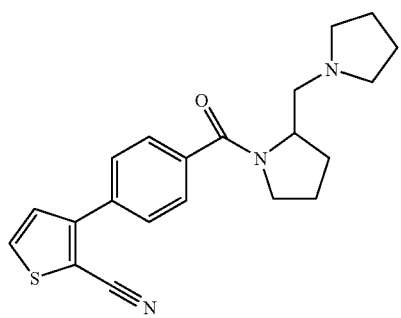 |

-continued
| Formula Number | Structure |
|---|---|
| X13 | 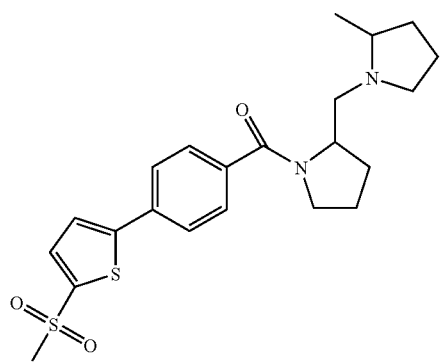 |
| X14 | 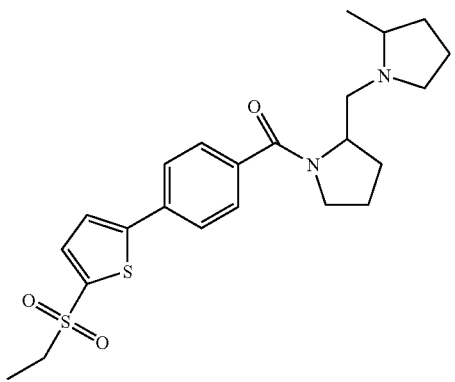 |
| X15 | 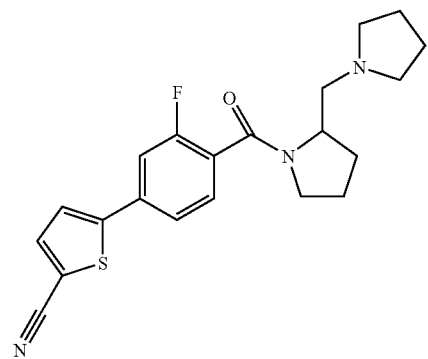 |
| X16 | 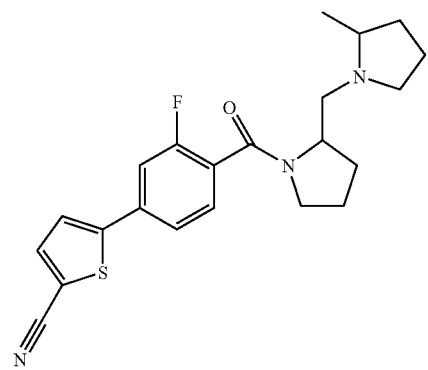 |

-continued
| Formula Number | Structure |
|---|---|
| X17 | 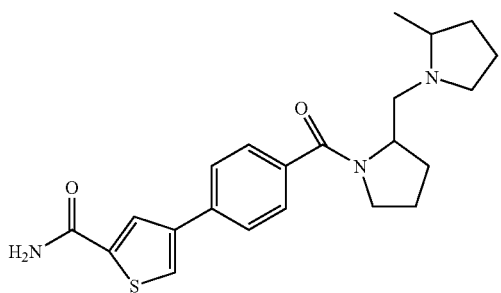 |
| X18 | 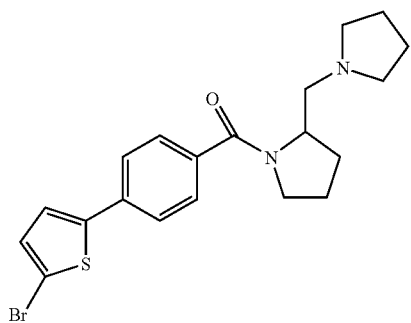 |
| X19 | 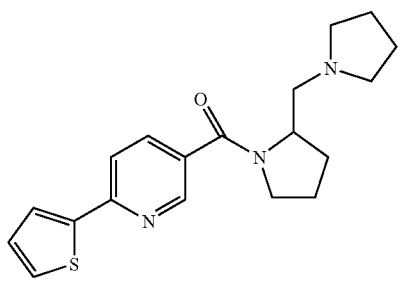 |
| X20 | 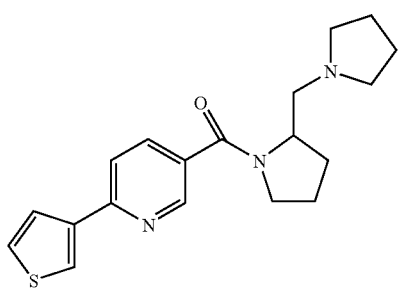 |
| X21 | 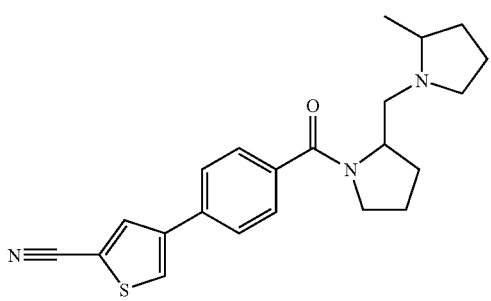 |

-continued
| Formula Number | Structure |
|---|---|
| X22 | 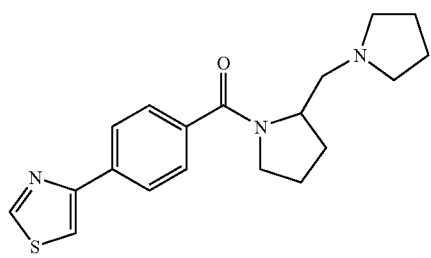 |
| X23 | 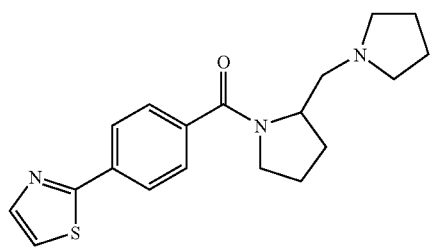 |
| X24 | 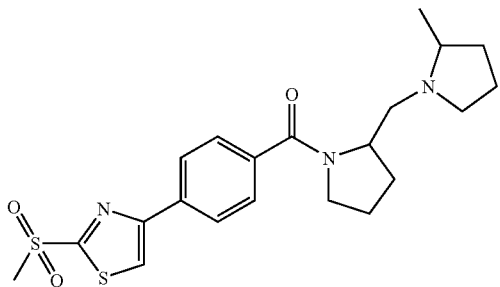 |
| X25 | 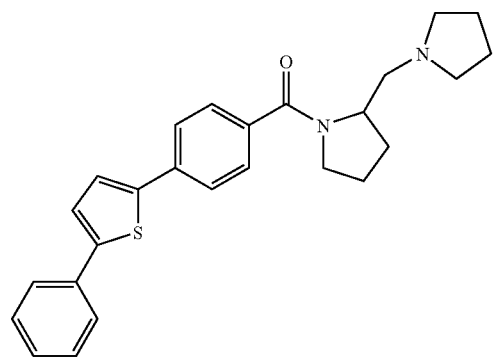 |
| X26 | 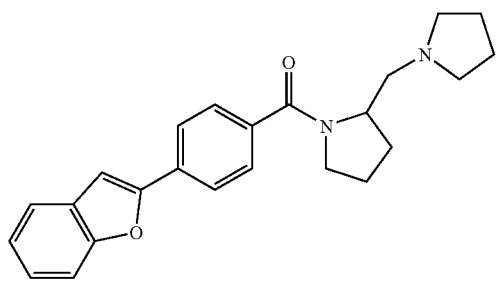 |

-continued
| Formula Number | Structure |
|---|---|
| X27 | 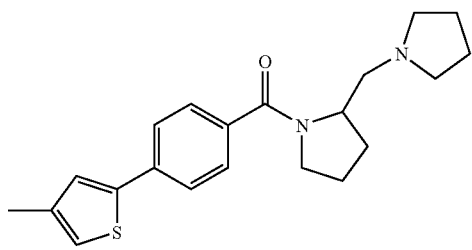 |
| X28 | 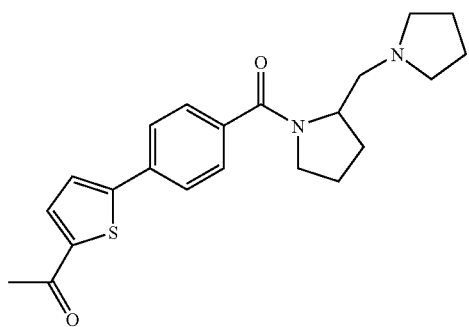 |
| X29 | 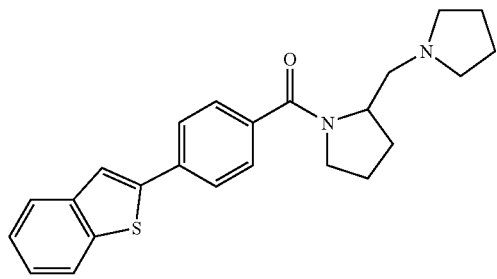 |
| X30 | 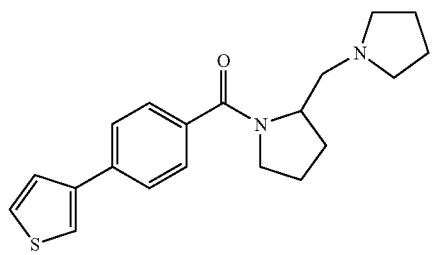 |
| X31 | 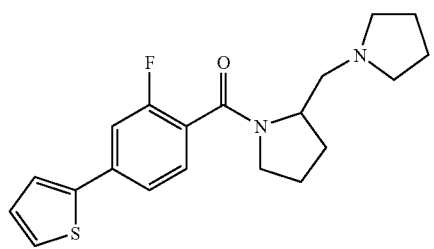 |

-continued
| Formula Number | Structure |
|---|---|
| X32 | 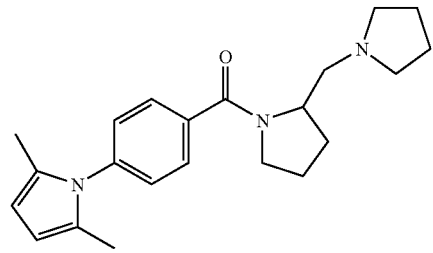 |
| X33 | 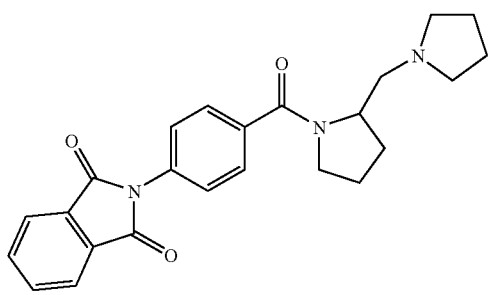 |
| X34 | 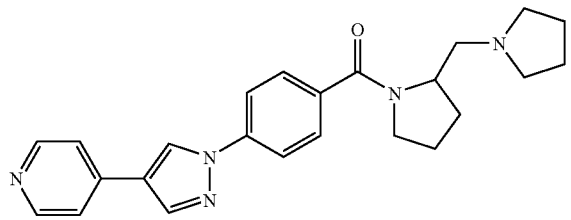 |
| X35 | 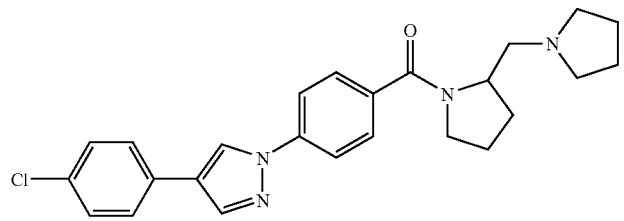 |
| X36 | 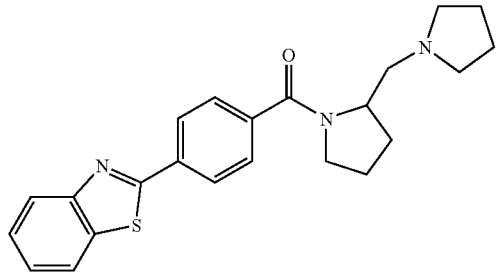 |
| X37 | 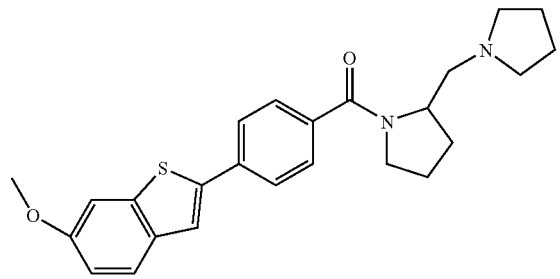 |

-continued
| Formula Number | Structure |
|---|---|
| X38 | 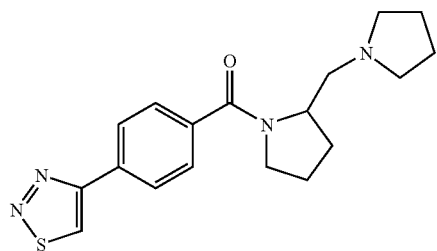 |
| X39 | 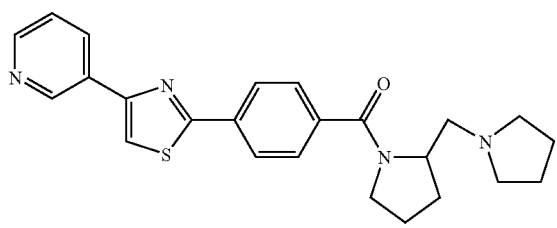 |
| X40 | 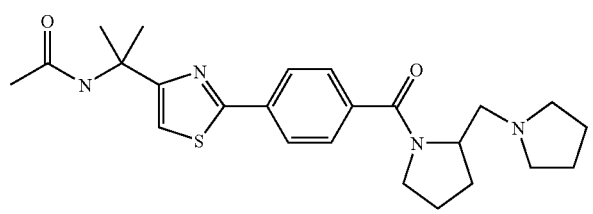 |
| X41 | 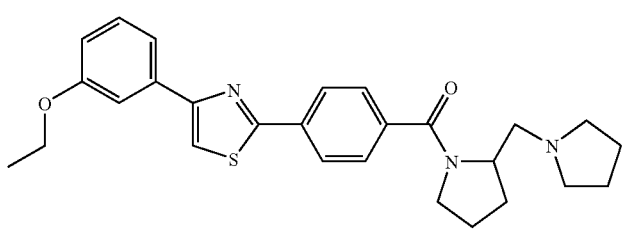 |
| X42 | 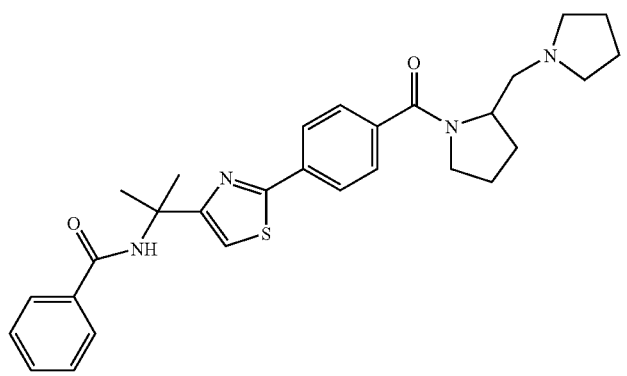 |

-continued
| Formula Number | Structure |
|---|---|
| X43 | 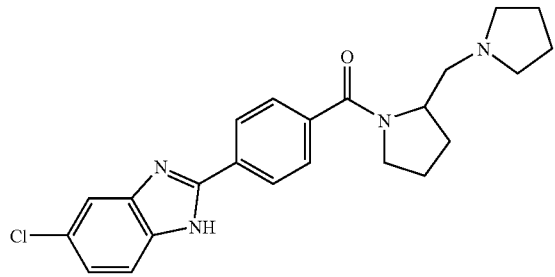 |
| X45 | 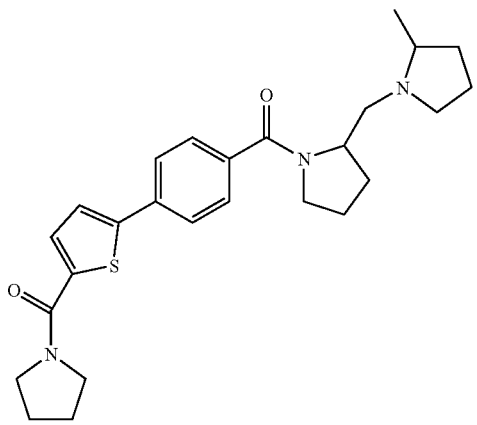 |
| X46 | 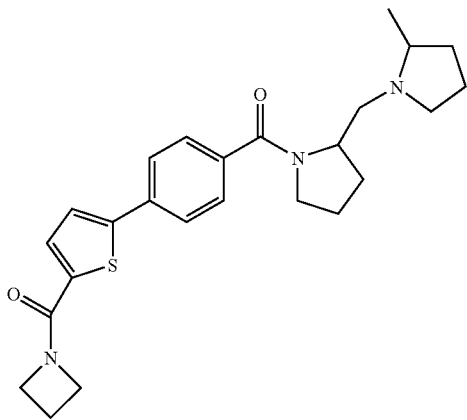 |
| X47 | 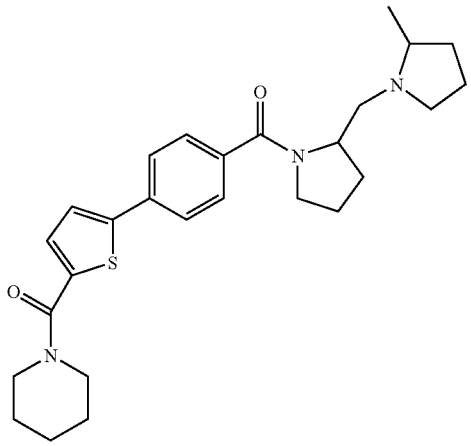 |

-continued
| Formula Number | Structure |
|---|---|
| X48 | 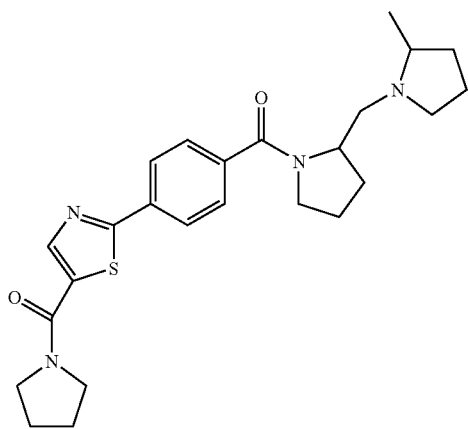 |
| X49 | 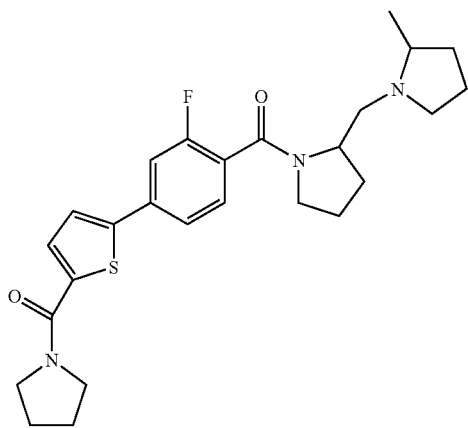 |
| X50 | 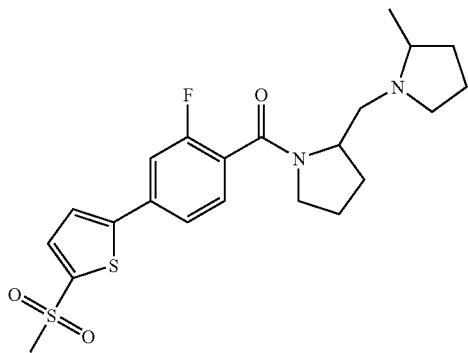 |

-continued
| Formula Number | Structure |
|---|---|
| X51 | 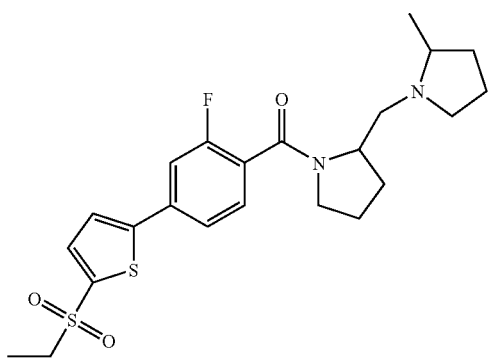 |
| X52 | 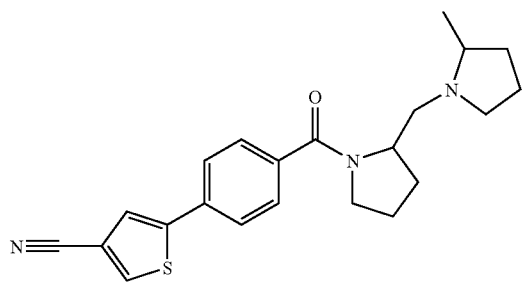 |
| X53 | 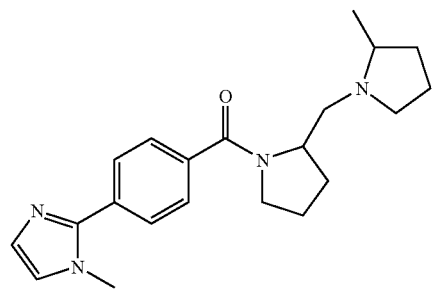 |
| X54 | 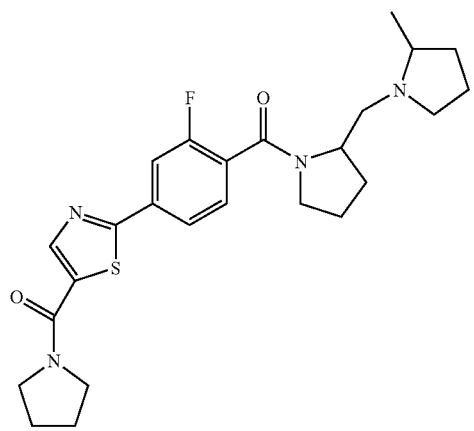 |

| Formula Number | Structure |
| --- | --- |
| X55 | 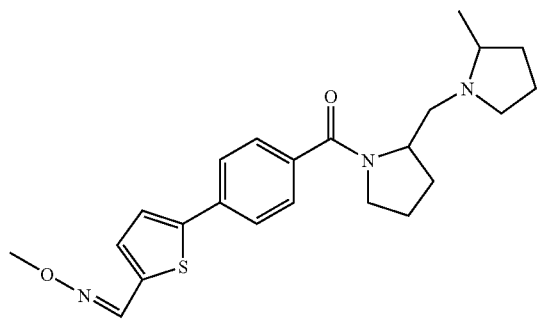 |
| X56 | 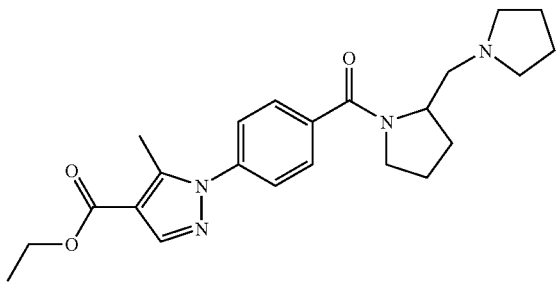 |
| X57 | 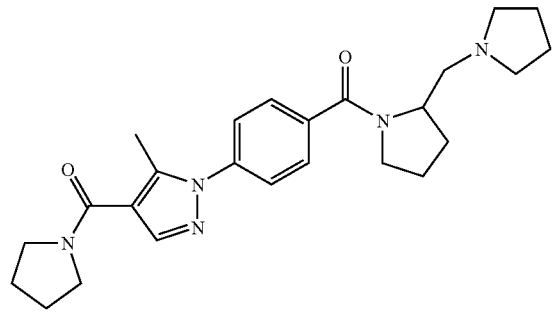 | or a pharmaceutically acceptable salt thereof.

13. The compound of claim 1, selected from the group consisting of:

5-[4-(2(S)-Pyrrolidin-1-ylmethyl-pyrrolidine-1-carbonyl)-phenyl]-thiophene-2-carbonitrile;

5-{4-[2-(2(S)-(2-(R)-methyl-pyrrolidin-1-ylmethyl)-pyrrolidine-1-carbonyl]-phenyl}-thiophene-2-carbonitrile;

5-[4-(2(S)-Pyrrolidin-1-ylmethyl-pyrrolidine-1-carbonyl)-phenyl]-thiophene-2-carboxylic acid amide;

(2(S)-Pyrrolidin-1-ylmethyl-pyrrolidin-1-yl)-(4-thiophen-2-yl-phenyl)-methanone;

5-[4-(2(S)-Pyrrolidin-1-ylmethyl-pyrrolidine-1-carbonyl)-phenyl]-thiophene-2-carboxylic acid dimethylamide;

2-Methyl-1-{5-[4-(2(S)-pyrrolidin-1-ylmethyl-pyrrolidine-1-carbonyl)-phenyl]-thiophen-2-yl}-propan-1-one;

5-[4-(2(S)-Pyrrolidin-1-ylmethyl-pyrrolidine-1-carbonyl)-phenyl]-thiophene-2-sulfonic acid amide;

[4-(5-Oxazol-5-yl-thiophen-2-yl)-phenyl]-(2(S)-pyrrolidin-1-ylmethyl-pyrrolidin-1-yl)-methanone;

[4-(5-Methylsulfanyl-thiophen-2-yl)-phenyl]-(2(S)-pyrrolidin-1-ylmethyl-pyrrolidin-1-yl)-methanone;

[4-(5-Methanesulfonyl-thiophen-2-yl)-phenyl]-(2(S)-pyrrolidin-1-ylmethyl-pyrrolidin-1-yl)-methanone;

{4-[5-(Pyrrolidine-1-carbonyl)-thiophen-2-yl]-phenyl}-(2(S)-pyrrolidin-1-ylmethyl-pyrrolidin-1-yl)-methanone;

3-[4-(2(S)-Pyrrolidin-1-ylmethyl-pyrrolidine-1-carbonyl)-phenyl]-thiophene-2-carbonitrile;

[4-(5-Methanesulfonyl-thiophen-2-yl)-phenyl]-[2-(S)-(2-(R)-methyl-pyrrolidin-1-ylmethyl)-pyrrolidin-1-yl]-methanone;

[4-(5-Ethanesulfonyl-thiophen-2-yl)-phenyl]-[2-(S)-(2-(R)-methyl-pyrrolidin-1-ylmethyl)-pyrrolidin-1-yl]-methanone;

5-[3-Fluoro-4-(2-pyrrolidin-1-ylmethyl-pyrrolidine-1-carbonyl)-phenyl]-thiophene-2-carbonitrile;

5-{3-fluoro-4-[2-(S)-(2-(R)-methyl-pyrrolidin-1-ylmethyl)-pyrrolidine-1-carbonyl]-phenyl}-thiophene-2-carbonitrile;

4-{4-[2-(S)-(2-(R)-Methyl-pyrrolidin-1-ylmethyl)-pyrrolidine-1-carbonyl]-phenyl}-thiophene-2-carboxylic acid amide;

[4-(5-Bromo-thiophen-2-yl)-phenyl]-(2(S)-pyrrolidin-1-ylmethyl-pyrrolidin-1-yl)-methanone;

(2(S)-Pyrrolidin-1-ylmethyl-pyrrolidin-1-yl)-(6-thiophen-2-yl-pyridin-3-yl)-methanone;
(2(S)-Pyrrolidin-1-ylmethyl-pyrrolidin-1-yl)-(6-thiophen-3-yl-pyridin-3-yl)-methanone;
4-{4-[2-(S)-(2-(R)-methyl-pyrrolidin-1-ylmethyl)-pyrrolidine-1-carbonyl]-phenyl}-thiophene-2-carbonitrile;
(2-(S)-Pyrrolidin-1-ylmethyl-pyrrolidin-1-yl)-(4-thiazol-4-yl-phenyl)-methanone;
(2-(S)-Pyrrolidin-1-ylmethyl-pyrrolidin-1-yl)-(4-thiazol-2-yl-phenyl)-methanone;
[4-(2-Methanesulfonyl-thiazol-4-yl)-phenyl]-[2-(S)-(2-(R)-methyl-pyrrolidin-1-ylmethyl)-pyrrolidin-1-yl]-methanone;
[4-(5-Phenyl-thiophen-2-yl)-phenyl]-((S)-2-pyrrolidin-1-ylmethyl-pyrrolidin-1-yl)-methanone;
(4-Benzofuran-2-yl-phenyl)-((S)-2-pyrrolidin-1-ylmethyl-pyrrolidin-1-yl)-methanone;
[4-(4-Methyl-thiophen-2-yl)-phenyl]-((S)-2-pyrrolidin-1-ylmethyl-pyrrolidin-1-yl)-methanone;
1-{5-[4-((S)-2-Pyrrolidin-1-ylmethyl-pyrrolidine-1-carbonyl)-phenyl]-thiophen-2-yl}-ethanone;
4-Benzo[b]thiophen-2-yl-phenyl)-((S)-2-pyrrolidin-1-ylmethyl-pyrrolidin-1-yl)-methanone;
((S)-2-Pyrrolidin-1-ylmethyl-pyrrolidin-1-yl)-(4-thiophen-3-yl-phenyl)-methanone;
(2-Fluoro-4-thiophen-2-yl-phenyl)-((S)-2-pyrrolidin-1-ylmethyl-pyrrolidin-1-yl)-methanone;
[4-(2,5-Dimethyl-pyrrol-1-yl)-phenyl]-(2-(S)-pyrrolidin-1-ylmethyl-pyrrolidin-1-yl)-methanone;
(S)-2-[4-(2-Pyrrolidin-1-ylmethyl-pyrrolidine-1-carbonyl)-phenyl]-isoindole-1,3-dione;
(S)-[4-(4-Pyridin-4-yl-pyrazol-1-yl)-phenyl]-(2-pyrrolidin-1-ylmethyl-pyrrolidin-1-yl)-methanone;
(S)-[4-[4-(4-Chloro-phenyl)-pyrazol-1-yl]-phenyl]-(2-pyrrolidin-1-ylmethyl-pyrrolidin-1-yl)-methanone;
(S)-(4-Benzothiazol-2-yl-phenyl)-(2-pyrrolidin-1-ylmethyl-pyrrolidin-1-yl)-methanone;
(S)-[4-(6-Methoxy-benzo[b]thiophen-2-yl)-phenyl]-(2-pyrrolidin-1-ylmethyl-pyrrolidin-1-yl)-methanone;
(S)-(2-Pyrrolidin-1-ylmethyl-pyrrolidin-1-yl)-(4-[1,2,3]thiadiazol-4-yl-phenyl)-methanone;
[4-(4-Pyridin-3-yl-thiazol-2-yl)-phenyl]-(2-pyrrolidin-1-ylmethyl-pyrrolidin-1-yl)-methanone;
N-(1-Methyl-1-{2-[4-(2-pyrrolidin-1-ylmethyl-pyrrolidine-1-carbonyl)-phenyl]-thiazol-4-yl}-ethyl)-acetamide;
{4-[4-(3-Ethoxy-phenyl)-thiazol-2-yl]-phenyl}-(2-pyrrolidin-1-ylmethyl-pyrrolidin-1-yl)-methanone;
N-(1-Methyl-1-{2-[4-(2-pyrrolidin-1-ylmethyl-pyrrolidine-1-carbonyl)-phenyl]-thiazol-4-yl}-ethyl)-benzamide;
[4-(5-Chloro-1H-benzoimidazol-2-yl)-phenyl]-(2-pyrrolidin-1-ylmethyl-pyrrolidin-1-yl)-methanone;
[4-(5-Chloro-1H-benzimidazol-2-yl)-phenyl]-(2-pyrrolidin-1-ylmethyl-pyrrolidin-1-yl)-methanone;
[2-(S)-(2-(R)-methyl-pyrrolidin-1-ylmethyl)-pyrrolidin-1-yl]-{4-[5-(pyrrolidine-1-carbonyl)-thiophen-2-yl]-phenyl}-methanone;
{4-[5-(Azetidine-1-carbonyl)-thiophen-2-yl]-phenyl}-[2-(S)-(2-(R)-methyl-pyrrolidin-1-ylmethyl)-pyrrolidin-1-yl]-methanone;
[2-(S)-(2-(R)-methyl-pyrrolidin-1-ylmethyl)-pyrrolidin-1-yl]-{4-[5-(piperidine-1-carbonyl)-thiophen-2-yl]-phenyl}-methanone;
[2-(S)-(2-(R)-methyl-pyrrolidin-1-ylmethyl)-pyrrolidin-1-yl]-{4-[5-(pyrrolidine-1-carbonyl)-thiazol-2-yl]-phenyl}-methanone;
{2-Fluoro-4-[5-(pyrrolidine-1-carbonyl)-thiophen-2-yl]-phenyl}-[2-(S)-(2-(R)-methyl-pyrrolidin-1-ylmethyl)-pyrrolidin-1-yl]-methanone;
[2-Fluoro-4-(5-methanesulfonyl-thiophen-2-yl)-phenyl]-[2-(S)-(2-(R)-methyl-pyrrolidin-1-ylmethyl)-pyrrolidin-1-yl]-methanone;
[4-(5-Ethanesulfonyl-thiophen-2-yl)-2-fluoro-phenyl]-[2-(S)-(2-(R)-methyl-pyrrolidin-1-ylmethyl)-pyrrolidin-1-yl]-methanone;
5-{4-[2-(S)-(2-(R)-methyl-pyrrolidin-1-ylmethyl)-pyrrolidine-1-carbonyl]-phenyl}-thiophene-3-carbonitrile;
[4-(1-Methyl-1H-imidazol-2-yl)-phenyl]-[2-(S)-(2-(R)-methyl-pyrrolidin-1-ylmethyl)-pyrrolidin-1-yl]-methanone;
{2-Fluoro-4-[5-(pyrrolidine-1-carbonyl)-thiazol-2-yl]-phenyl}-[2-(S)-(2-(R)-methyl pyrrolidin-1-ylmethyl)-pyrrolidin-1-yl]-methanone;
5-{4-[2-(S)-(2-(R)-methyl-pyrrolidin-1-ylmethyl)-pyrrolidine-1-carbonyl]-phenyl}-thiophene-2-carbaldehyde O-methyl-oxime;
5-Methyl-1-[4-(2-(S)-pyrrolidin-1-ylmethyl-pyrrolidine-1-carbonyl)-phenyl]-1H-pyrazole-4-carboxylic acid ethyl ester L-tartrate; and
{5-Methyl-1-[4-(2-(S)-pyrrolidin-1-ylmethyl-pyrrolidine-1-carbonyl)-phenyl]-1H-pyrazol-4-yl}-pyrrolidin-1-yl-methanone;
or a pharmaceutically acceptable salt thereof.

14. A pharmaceutical composition which comprises a compound or salt of claim 1 and a pharmaceutically acceptable carrier.

15. A compound structurally represented by the formula

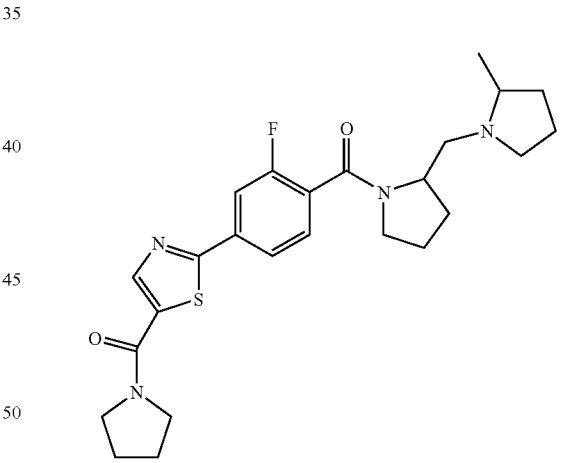

or a pharmaceutically acceptable salt thereof.

16. The compound {2-Fluoro-4-[5-(pyrrolidine-1-carbonyl)-thiazol-2-yl]-phenyl}-[2-(S)-(2-(R)-methylpyrrolidin-1-ylmethyl)-pyrrolidin-1-yl]-methanone, or a pharmaceutically acceptable salt thereof.

17. A pharmaceutical composition which comprises a compound or salt of claim 15 and a pharmaceutically acceptable carrier.

18. A pharmaceutical composition which comprises a compound or salt of claim 16 and a pharmaceutically acceptable carrier.

* * * * *

UNITED STATES PATENT AND TRADEMARK OFFICE
CERTIFICATE OF CORRECTION

Page 1 of 1

| | |
|---|---|
| PATENT NO. | : 7,705,025 B2 |
| APPLICATION NO. | : 11/574044 |
| DATED | : April 27, 2010 |
| INVENTOR(S) | : Finley et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this
Eleventh Day of January, 2011

David J. Kappos
*Director of the United States Patent and Trademark Office*